(12) United States Patent
Offner

(10) Patent No.: US 7,731,973 B2
(45) Date of Patent: *Jun. 8, 2010

(54) METHOD OF TREATING IMMUNE PATHOLOGIES WITH LOW DOSE ESTROGEN

(75) Inventor: Halina Offner, Portland, OR (US)

(73) Assignees: Oregon Health and Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/103,633

(22) Filed: Apr. 15, 2008

(65) Prior Publication Data

US 2008/0207580 A1 Aug. 28, 2008

Related U.S. Application Data

(63) Continuation of application No. 10/275,833, filed as application No. PCT/US01/40710 on May 11, 2001, now Pat. No. 7,371,385.

(60) Provisional application No. 60/203,980, filed on May 12, 2000.

(51) Int. Cl.
A61K 39/00 (2006.01)
A61K 45/00 (2006.01)
A61K 47/00 (2006.01)

(52) U.S. Cl. ............................. 424/198.1; 424/278.1

(58) Field of Classification Search ................... None
See application file for complete search history.

(56) References Cited

U.S. PATENT DOCUMENTS

| 5,194,425 | A | 3/1993 | Sharma et al. |
| 5,223,426 | A | 6/1993 | Skibbens et al. |
| 5,569,585 | A | 10/1996 | Goodwin et al. |
| 5,612,035 | A | 3/1997 | Howell et al. |
| 5,614,192 | A | 3/1997 | Vandenbark |
| 5,776,459 | A | 7/1998 | Vandenbark |
| 5,837,246 | A | 11/1998 | Howell et al. |
| 5,856,446 | A | 1/1999 | Weiner et al. |
| 5,858,968 | A | 1/1999 | Weiner et al. |
| 5,869,093 | A | 2/1999 | Weiner et al. |
| 5,939,281 | A | 8/1999 | Lehmann et al. |
| 5,939,400 | A | 8/1999 | Steinman et al. |
| 6,019,971 | A | 2/2000 | Weiner et al. |
| 6,039,947 | A | 3/2000 | Weiner et al. |
| 6,045,796 | A | 4/2000 | Sriram et al. |
| 6,090,387 | A | 7/2000 | Howell et al. |
| 6,113,903 | A | 9/2000 | Albertini et al. |
| 6,159,470 | A | 12/2000 | Howell et al. |
| 6,197,926 | B1 | 3/2001 | Gaur |
| 6,207,645 | B1 | 3/2001 | Howell et al. |
| 6,218,132 | B1 | 4/2001 | Spack et al. |
| 6,221,352 | B1 | 4/2001 | Howell et al. |
| 6,936,599 | B2 | 8/2005 | Voskuhl |
| 6,958,327 | B1 | 10/2005 | Hillisch et al. |
| 2002/0183299 | A1 | 12/2002 | Voskuhl |

FOREIGN PATENT DOCUMENTS

| EP | 0 159 739 A1 | 10/1985 |
| EP | 10175854 | 6/1998 |
| EP | 957359 | 11/1999 |
| WO | WO 94/25063 | 11/1994 |
| WO | WO 99/58977 | 11/1999 |
| WO | WO 01/32680 A2 | 5/2001 |

OTHER PUBLICATIONS van den Brink et al., 1993, Ann. Rheum. Dis. vol. 52: 862-865.*
Acha-Orbea et al., "Limited Heterogeneity of T Cell Receptors from Lymphocytes Mediating Autoimmune Encephalomyelitis Allows Specific Immune Intervention," Cell, 54(2):263-273 (1988).
Arden et al., Immunogenetics 42:355-500 (1995).
Bebo et al., J. Immunol. 162:35 (1998).
Bebo et al., J. Neurosci. Res. 52:420-429 (1998).
Bourdette et al., Cell Immunol. 112:351 (1988).
Brosterhaus et al., "Enrichment and detection of live antigen-specific CD4+ T cells based on cytokine secretion," Eur. J. Immunol. 29:4053-4059 (1999).
Bourdette et al., "A highly immunogenic trivalent T cell receptor peptide vaccine for multiple sclerosis," Multiple Sclerosis, 11:1-10, (Jul. 5, 2005).
Choi et al., Proc. Natl. Acad. Sci. USA 86:8941-8945 (1989).
Carlsten et al., Infamm Res. vol. 45:26-30, (1996).
Chou et al., "Immunity to TCR peptides in multiple sclerosis," J. Immunol 152:2520-2529 (1994).
Chou et al., "MCH-restriction, cytokine profile, and immunoregulatory effects of human T cells specific for TCR Vβ CDR2 peptides: comparison with myelin basic protein-specific T cells," J. Neuroscience Res. 45:838-851 (1996).
Cochlovius et al., J. Immunol. 165:4731-4741 (2000).
Concannon et al., Proc. Natl. Acad. Sci. USA 83:6598-6602 (1986).
Correale et al., J. Immunol. 161:3365-3374 (1998).
Dalton et al., Science 259:1739-1742 (1993).
English Translation of Japanese Patent Application No. JP101175854, dated Jun. 30, 1998, found at http://www4.jpdl.ncipi.go.jp/cgi-bin/tran, printed Sep. 14, 2006.
Evavold et al., Immunology Today 14:602-609 (1993).
Fairchild, Euro. J. Immunogenet. 24:155-167 (1997).
Genevee et al., Eur. J. Immunol. 22:1261-1269 (1992).
Gilmore et al., J. Immunol. 158:446-451 (1997).
Goverman et al., Cell 72:551-560 (1993).

(Continued)

Primary Examiner—Amy E Juedes
(74) Attorney, Agent, or Firm—Klarquist Sparkman, LLP

(57) ABSTRACT

The invention provides a method of ameliorating a Th1-mediated immune pathology in a mammal. The method is practiced by administering a low dose of estrogen to the mammal. Optionally, an immunotherapeutic agent can also be administered to the mammal. Also provided are kits containing a low dose of estrogen and an immunotherapeutic agent.

14 Claims, 20 Drawing Sheets

OTHER PUBLICATIONS

Hashim et al., *J. Immunol.* 144:4621-4627 (1990).
Jansson et al., *Journal of Neuroimmunology* 53:203-207 (1994).
International Search Report from the prior PCT Application No. PCT/US01/40710, 7 pages (Sep. 9, 2002).
Kimura et al., *Eur. J. Immunol.* 17:375-383 (1987).
Kumar et al., *J. Exp. Med.* 178:909-916 (1993).
Martin et al., *Nat. Immunol.* 2:785-788 (2001).
Offner et al., *J. Immunol.* 161:2178-2186 (1998).
Offner et al., *Journal of Clinical Investigation* 105(10):1465-1472 (2000).
Olsson et al., "Autoreactive T lymphocytes in multiple sclerosis determined by antigen-induced secretion of interferon-γ," *J. Clin. Invest.* 86:981-985 (1990).
Robinson et al., *J. Immunol.* 146:4392-4397 (1991).
Roselli et al., *Endocrine* 64:139 (1996).
Rovaris et al., *J. Neurol. Sci.* 186 Suppl. 1:S3-9 (2001).
Savoie et al., *Pac. Symp. Biocomput.* 1999:182-189 (1999).
Sicotte et al., *Ann. Neurol.* 52:421-428 (2002).
Soldan et al., "Immune Modulation in Multiple Sclerosis Patients Treated with the Pregnancy Hormone Estriol," *J. Immunology* 171:6267-6274 (2003).
Steinman et al., *Trends in Immunology* 26:565-571 (2005).
Thornton and Shevach, "CD4+CD25+ Immunoregulatory T Cells Suppress Polyclonal T Cell Activation In Vitro by Inhibiting Interleukin 2 Production," *J. Experimental Medicine* 188(2):287-296 (1998).
Van Epps, "Thomas Rivers and the EAE Model," *JEM* 202(1):4 (2005).
Vandenbark et al., "Treatment of multiple sclerosis with T-cell receptor peptides: Results of a double-blind pilot trail," *Nature Med.* 2:1109-1115 (1996).
Vandenbark, "TCR Peptide Vaccination in Multiple Sclerosis: Boosting a Deficient Natural Regulatory Network that may Involve TCR-Specific CD4+CD25+ Treg Cells," *Current Drug Targets* 4:217-229 (2005).
Vaniene et al., *J Neurosci. Res.* 45:475-486 (1996).
Venken et al., "Secondary Progressive in Contrast to Relapsing-Remitting Multiple Sclerosis Patients Show a Normal CD4+CD25+ Regulatory T-Cell Function and FOXP3 Expression," *J. Neuroscience Research* 83:1432-1446 (2006).
WPI Database, Derwent Publkications Ltd., London, GB, AN 1998-422294, XP0021 89653 and JP 10 175854A (Doctors Cosmetic YG) Abstract (1998).
Zipp et al., *Brain* 121:1395-1407 (1998).
Alonso et al., "Recent Use of Oral Contraceptives and the Risk of Multiple Sclerosis," *Arch Neurol*, 62:1362-1365, (2005).
"Progress in Autoimmune Disease Research," *National Institute of Allergy and Infectious Diseases*, pp. 1-126, (Mar. 2005).
Zheng et al., "Exacerbation of autoimmune arthritis by copolymer-I through promoting type 1 immune response and autoantibody production," *Autoimmunity*, 41(5):363-371, (Jul. 2008).

* cited by examiner

METHOD OF TREATING IMMUNE PATHOLOGIES WITH LOW DOSE ESTROGEN

CROSS REFERENCE TO RELATED APPLICATIONS

This is a continuation of U.S. patent application Ser. No. 10/275,833, filed Nov. 8, 2002 now U.S. Pat. No. 7,371,385, which is a §371 U.S. national stage of International Application No. PCT/US01/40710, filed May 11, 2001, which was published in English under PCT Article 21(2), and claims the benefit of U.S. Provisional Application No. 60/203,980 filed May 12, 2000. U.S. patent application Ser. No. 10/275,833 is herein incorporated by reference in its entirety.

BACKGROUND OF THE INVENTION

1. Field of the Invention

This invention relates generally to the fields of immunology and medicine and, more specifically, to the use of low dose estrogen to treat immune pathologies.

2. Background Information

The involvement of female sex hormones in immune pathologies has been proposed based on a number of clinical and experimental observations. First, a variety of autoimmune diseases, including multiple sclerosis, rheumatoid arthritis and Grave's disease, preferentially affect women, and first occur during the reproductive years. Second, during pregnancy, when levels of female sex hormones are high, clinical remissions of cell-mediated autoimmune diseases are common, with disease exacerbation often seen post-partum when sex hormone levels are low. Third, in animal models of autoimmune disease, administration of estrogen at levels equal to or greater than those found in pregnancy has been shown to suppress the clinical and histopathological symptoms of the disease. Fourth, in vitro, estrogen at the high concentrations found in pregnancy has been shown to inhibit production of inflammatory cytokines and to stimulate production of anti-inflammatory cytokines by autoantigen-specific CD4+ cells from multiple sclerosis patients. However, in the same study, low concentrations of estrogen had the opposite effect, stimulating production of inflammatory cytokines, with little or no effect on production of anti-inflammatory cytokines (Correale et al., *J. Immunol.* 161:3365-3374 (1998).

To explain these observations, it has been proposed that the response to estrogen is biphasic, with high levels associated with protection from autoimmune disease, and low levels associated with promotion of disease. However, because of the potential adverse effects of high levels of estrogen on the reproductive and circulatory systems, and because of the potential unwanted side effects in males, administration of high levels of estrogen is unlikely to be widely useful as a therapy.

The effect of administering low dose estrogen to an individual with an immune disease has not previously been tested, although, from the clinical and experimental observations described above, little or no beneficial effect on the course of the disease would be predicted.

There exists a need to design effective therapies that are applicable for treating a variety of immune pathologies, in both genders, with minimal side effects. The present invention satisfies this need and provides related advantages as well.

SUMMARY OF THE INVENTION

The invention provides a method of ameliorating a Th1-mediated immune pathology in a mammal. The method is practiced by administering a low dose of estrogen to the mammal. Optionally, an immunotherapeutic agent can also be administered to the mammal. Also provided are kits containing a low dose of estrogen and an immunotherapeutic agent.

BRIEF DESCRIPTION OF THE DRAWINGS

FIG. 7 shows the effect of administration of BV8S2 (Vβ8.2) protein in IFA on the development of EAE in male and female mice.

DETAILED DESCRIPTION OF THE INVENTION

Figure 1:
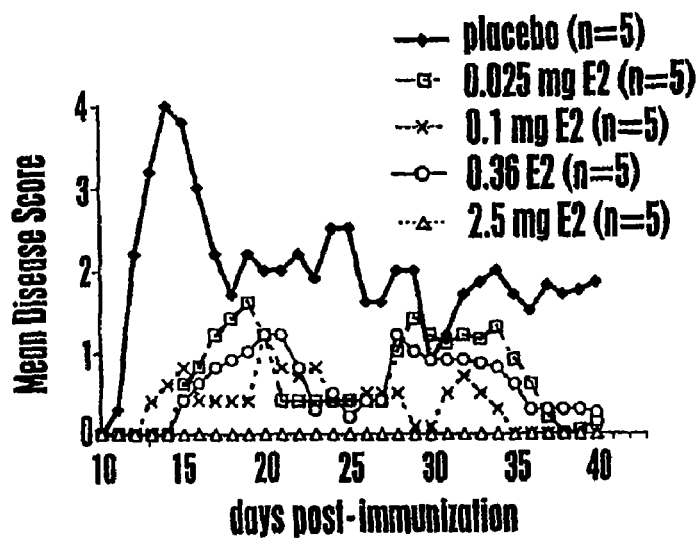
FIG. 1 shows the effect of various concentrations of 17β-estradiol (E2) on the severity of EAE in female SJL mice.

As disclosed herein, administration of a low dose of estrogen unexpectedly reduces the severity of Th1-mediated immune pathologies. Additionally, low dose estrogen and immunotherapeutic agents act synergistically in reducing the severity of Th1-mediated immune pathologies. These effects appear to be due, in part, to the effect of low dose estrogen on reducing the expression of pro-inflammatory cytokines and chemokines by T cells in the periphery and at the site of the pathology.

Therefore, the invention provides a novel method of preventing or ameliorating immune pathologies in a mammal by administering to the mammal a low dose of estrogen. Optionally, the method further comprises administering an immunotherapeutic agent. The methods are advantageous in that low doses of estrogen can be administered to both males and females to prevent or ameliorate immune pathologies. Side effects of high dose estrogen therapy, which are detrimental in females and preclude its use in males, are expected to significantly reduced by administering low dose estrogen. Additionally, the synergistic effects of low-dose estrogen and an immunotherapeutic agent in inhibiting pathogenic immune responses allow a lower dose of agent to be used than required using the agent alone, which reduces potential side effects and lowers the cost of therapy.

The methods of the invention can be practiced with respect to a variety of immune pathologies. As used herein, the term "immune pathology" refers to a pathology mediated by a detrimental immune response. Such pathologies are known in the art and include, but are not limited to, autoimmune pathologies, immune reactions by or against allografts, immune responses to infectious agents, chronic immune responses, allergic reactions and immunosuppressive responses and immunoproliferative pathologies. Prognostic indicators and clinical signs associated with particular immune pathologies are well known in the art. Additionally, as described below, immunotherapeutic agents useful in preventing or treating immune pathologies are well known in the art, which can effectively be used in combination with low dose estrogen therapy in the methods of the invention.

Those skilled in the art appreciate that many immune pathologies are mediated by a combination of Th1, Th2, antibody, B cell, phagocytic and complement responses. Preferably, the methods of the invention are practiced with respect to "Th1-mediated pathologies," which are pathologies in which the detrimental immune response is primarily or partially a T helper 1 (Th1) type immune response. A Th1 immune response is characterized by secretion of pro-inflammatory cytokines, which include IL-12, IFN-γ and TNF-α. Th1-mediated pathologies include most autoimmune diseases, many alloimmune disorders, certain allergic conditions, certain chronic inflammatory conditions, and certain infectious conditions.

An immune pathology can alternatively be mediated by a "Th2 immune response," which indicates that the detrimental immune response is partially or primarily of the T helper 2 (Th2) type. A Th2 response is characterized by secretion of anti-inflammatory cytokines, such as IL-4, IL-10, IL-13 and TGF-β.

In most autoimmune pathologies, T cells recognize a host component in one or more tissues as foreign, and attack that tissue. Exemplary autoimmune pathologies affecting mammals include rheumatoid arthritis (RA), juvenile oligoarthritis, collagen-induced arthritis, Sjogren's syndrome, multiple sclerosis (MS), experimental autoimmune encephalomyelitis (EAE), inflammatory bowel disease (e.g. Crohn's disease, ulceritive colitis), autoimmune gastric atrophy, pemphigus vulgaris, psoriasis, vitiligo, type I diabetes, myasthenia gravis, Grave's disease, Hashimoto's thyroiditis, sclerosing cholangitis, sclerosing sialadenitis, systemic lupus erythematosis, Addison's disease, systemic sclerosis, polymyositis, dermatomyositis, pernicious anemia, and the like.

Alloimmune pathologies occur when tissue is transplanted from a donor whose HLA antigens do not completely match the recipient antigens. The donor cells can be recognized by the recipient immune system as foreign, resulting in rejection of the transplanted tissue. Alternatively, donor immune cells can recognize the recipient tissues as foreign, and attack the recipient (graft versus host disease). Thus, a pathogenic alloimmune response can be a response by or against a transplanted organ (e.g. heart, blood vessel, valve, liver, lung, kidney, skin) or infused hematopoietic cells, such as an apheresis product or bone marrow.

Septic shock is a life-threatening response to infectious agents. High levels of bacterial toxins, including exotoxins and endotoxins, can inappropriately activate the host immune system to produce hypersensitivity reactions that rapidly leading to septic shock with associated organ failure and death. Septic shock is associated with both gram-negative bacteria, such as *Staphylococcus* species, *Streptococcus* species, as well as gram-positive bacteria, and often is associated with infection following surgery or trauma.

Chronic inflammatory responses are often initially responses to infectious agents, but can be of any etiology, including tissue trauma. Chronic inflammatory responses are associated with a variety of diseases, including cardiovascular disease, coronary disease, cirrhosis, arthritis, cholestasis, tuberculosis, leprosy, syphilis, periodontitis, fibrosis, glomerulonephritis, and certain cancers.

Infectious agents that cause chronic inflammatory immune responses include, for example, bacteria (e.g. *Helicobacteria; Mycobacteria; Spirochocae; Yersinia* and the like), viruses (e.g. HIV, hepatitis viruses, herpes simplex viruses, papovavirus, rabies virus), fungi, protozoa, helminths and prions.

Allergic reactions are hypersensitivity reactions to agents in the environment. Allergic reactions can be IgE/mast cell mediated, antibody mediated, Th1 or Th2 cell mediated, or a combination thereof. Allergic conditions and their etiology are well known in the art. Common allergic conditions include, for example, asthma, hay fever and food allergies.

Other immune pathologies that can be amenable to treatment with low dose estrogen include immune deficiency disorders, wherein a mammal mounts an inadequate immune response. Immune deficiencies can be caused, for example, by HIV, the causative agent of AIDS; by malignancy; by old age; by malnutrition; by metabolic disease; by drug therapy; or by splenectomy. Immune pathologies that can be amenable to treatment with low dose estrogen include further include T cell replicative pathologies, including T cell leukemias and lymphomas.

Low dose estrogen therapy, alone or in combination with immunotherapeutic agents or conventional therapies (e.g. antibiotics, antiviral agents, chemotherapy, radiation, as appropriate for the particular disease), can be used to reduce the severity of the immune pathologies described above. As described herein, because of the inhibitory effect of low dose estrogen on TNFα expression, chemokine expression and chemokine receptor expression, low dose estrogen therapy will be particularly useful in pathologies mediated by Th1 type inflammatory responses.

As used herein, the term "ameliorating," with reference to an immune pathology, refers to any observable beneficial effect of the treatment. The beneficial effect can be evidenced, for example, by a delayed onset of clinical symptoms in a susceptible mammal, a reduction in severity of some or all clinical symptoms of the disease, a slower progression of the disease, a reduction in the number of relapses of the disease, a reduction in the number or activity (e.g. Th1 type cytokine secretion) of pathogenic T cells at the site of pathology or in the circulation, an improvement in the overall health or well-being of the individual, or by other parameters well known in the art that are specific to the particular disease. Those skilled in the art can determine, based on knowledge of the expected course of the particular disease, whether there is a delayed onset of clinical symptoms. Those skilled in the art can also determine whether there is an amelioration of the clinical symptoms or reduction in the number or activity of pathogenic T cells following treatment as compared with before treatment or as compared to an untreated mammal.

A useful method of monitoring the effect of a treatment that potentially ameliorates multiple sclerosis is magnetic resonance imaging, or MRI. As used herein, the term "magnetic resonance imaging" refers to conventional MRI methods, as well as improved magnetic resonance (MR) techniques, such as cell-specific imaging, magnetization transfer imaging (MTI), gadolinium (Gd)-enhanced MRI, proton magnetic resonance spectroscopy (MRS), diffusion-weighted imaging (DWI), functional MR imaging (fMRI), and the other neuroimaging methods known in the art. MRI methods and their applications to MS are described, for example, in Rovaris et al, *J. Neurol. Sci.* 186 Suppl 1:S3-9 (2001). MRI techniques allow an assessment of the effects of treatment on amelioration of a variety of well-known indicia of MS, including edema, blood brain barrier break-down, demyelinisation, gliosis, cellular infiltration, axonal loss, T2 lesion load, T1 lesion load, gadolinium positive lesion load, and the like.

As used herein, the term "mammal" refers to a human, a non-human primate, canine, feline, bovine, ovine, porcine, murine or other veterinary or laboratory mammal. Those skilled in the art understand that the immune responses and immune pathologies of mammals share many common features, and that a therapy which reduces the severity of an immune pathology in one species of mammal is predictive of the effect of the therapy on another species of mammal. The skilled person also appreciates that credible animal models of many human immune pathologies are known. As described in the Example, EAE is a credible animal model of human multiple sclerosis.

As used herein, the term "estrogen" refers to the steroids commonly known as 17β-estradiol (E2), estrone (E1) and estriol (E3). Also included within the term "estrogen" are metabolites and derivatives of E1, E2 and E3. Such metabolites and derivatives act as agonists of the estrogen receptor (ERα or ERβ) and have a similar core steroid structure as E1, E2 or E3, but can have one or more different groups (e.g. hydroxyl, ketone, halide, etc.) at one or more ring positions. Those skilled in the art can readily determine whether such metabolites and derivatives are agonists of estrogen by in vitro assays that measure signaling through the estrogen receptor. Alternatively, the effects of metabolites and derivatives of estrogen can be assessed, and compared to the effects of known estrogens, using any of the in vivo and in vitro assays that report estrogen's effects, as described in the Examples, below.

The methods of the invention can also be practiced with a non-steroidal estrogen analog that acts as an agonist of the estrogen receptor. Methods of identifying receptor agonists from libraries of compounds are well known in the art, and include binding assays (e.g. competitive and non-competitive radioimmunoassays) and signaling assays (e.g. transcription-based assays using reporter genes driven by an estrogen response element). Libraries of naturally occurring and synthetic compounds, including inorganic compounds, peptides, lipids, saccharides, nucleic acids and small organic molecules, are commercially available, and can be screened in high-throughput assays to identify estrogen analogs.

In the methods of the invention, estrogen is administered at a low but sufficient dose to reduce the severity of the particular immune pathology exhibited by the mammal. The dose will depend, among other considerations, on the type of estrogen, its formulation and route of administration, the duration of therapy, the type and severity of the pathology, and on the weight and gender of the mammal.

As used herein, the term "low dose" refers to an amount sufficient to raise the serum concentration above basal levels, but below pregnancy levels. The diestrus, estrus and pregnancy serum concentrations of E2 and E3 in mice are shown in Table 1. Human female physiologic concentrations of E1 and E3 are roughly equivalent to those of E2, which circulates at 10 to 1,000 pg/ml during the normal menstrual cycle, and up to 35,000 pg/ml during pregnancy.

TABLE 1

|  | 17β-estradiol (pg/ml) | Estriol (pg/ml) |
| --- | --- | --- |
| Diestrus | 20-30 | <100 |
| Estrus | 100-200 | <100 |
| Pregnancy | 5,000-10,000 | 2,000-3,000 |

Thus, a low dose of estrogen can raise serum E1, E2 or E3 to at least 10 pg/ml, such as 20 pg/ml, 30 pg/ml, 40 pg/ml, 50 pg/ml, 75 pg/ml, 100 pg/ml, 150 pg/ml, 200 pg/ml, 300 pg/ml, 400 pg/ml, 500 pg/ml, 750 pg/ml, 1000 pg/ml, 1500 pg/ml, and generally will not raise serum E1, E2 or E3 beyond 2000 pg/ml. The amount of estrogen to administer to achieve desired hormone levels in the serum is known in the art, and will depend, for example, on the weight of the mammal, the half-life of the particular estrogen, and the route and form of administration. The efficacy of a particular dose of estrogen can be monitored and adjusted during therapy by examining standard disease parameters.

Those skilled in the art can determine an appropriate time and duration of therapy to achieve the desired preventative or ameliorative effects on the immune pathology. Thus, the methods of the invention can be practiced so as to maintain low levels of estrogen in the blood for several days, weeks, months or years, or over the course of the lifetime of the individual. For example, the therapy can be administered continuously to an individual at risk of developing an immune pathology, such as an individual with a genetic predisposition to a pathology, or with preclinical indications of the pathology. Likewise, estrogen can be administered continuously to an individual early or late in the course of the disease, or only administered during exacerbations of the disease until symptoms are controlled.

Low doses of estrogen can be prepared in any convenient form and administered by any convenient route known in the art. Preferably, for human therapy, estrogen will be administered orally, transdermally, subcutaneously, intravenously, intramuscularly, by a respiratory route (e.g. inhalation), intranasal, enteral, topical, sublingual, or rectal means. Estrogen can also be administered directly to the site of the pathology, such as skin lesions, inflamed joints, into the central nervous system, and the like. For continuous release of defined concentrations of estrogen, administration via micropumps, biopolymers, liposomes and other slow-release vehicles is advantageous.

Optionally, low dose estrogen therapy can be combined with administration of an immunotherapeutic agent. As used herein, the term "immunotherapeutic agent" refers to any compound used prophylactically or therapeutically to inhibit an immune response or to ameliorate an immune pathology. Preferably, the immunotherapeutic agent will be administered at a lower dose than that required for complete efficacy on its own, such that when combined with administration of a low dose of estrogen, there will be a pronounced effect on reduction of disease severity not achieved by the immunotherapy alone. Administering a lower dose of immunotherapeutic agent reduces the risk of adverse effects, as well as reduces the cost of therapy.

The immunotherapeutic agent can be administered in combination with estrogen or separately; either before, at the same time, or after estrogen administration; either by the same route or by a different route (e.g. any of the routes described above); and either at the same site or at a different site. Those skilled in the art can determine appropriate conditions for administering both a low dose of estrogen and an immunotherapeutic agent to a mammal.

The choice of immunotherapeutic agent to use and route and site of administration will depend on the particular immune pathology. A variety of agents with at least partial efficacy in treating immune pathologies are known in the art, and their mechanisms of action are often well understood. Other immunotherapeutic agents with similar mechanisms of action are in development.

The activation of a T cell immune response requires interaction between a T cell receptor on the surface of the pathogenic T cell, and an antigenic peptide bound to an HLA (MHC) molecule on the surface of an antigen presenting cell or target cell. Any agent which disrupts this trimolecular complex can be effective in combination with low dose estrogen therapy in reducing the T cell immune response. Agents which disrupt the trimolecular complex can be either immunomodulatory agents or immunoblocking agents, or act by both an immunomodulatory and a blocking mechanism.

As used herein, the term "immunomodulatory agent" is intended to refer to an agent that induces a host immune response, such as a tolerogenic response or an active immune response in a mammal.

Exemplary immunomodulatory agents that cause a tolerogenic response, which leads to immunological unresponsiveness, are autoantigens targeted by pathogenic T cells in an autoimmune response. Autoantigens and the administration of these autoantigens by a variety of routes (including oral and intravenous routes) so as to induce tolerance are known in the art and described, for example, in U.S. Pat. Nos. 6,039,947; 6,019,971; 5,869,093; 5,858,968 and 5,856,446.

Known or suspected autoantigens, with their associated diseases, include: myelin basic protein, proteolipid protein, major oligodendrocytic protein, myelin associated glycoprotein, and αB-crystallin (multiple sclerosis and EAE); collagen type II, heat shock proteins, aggrecans, proteoglycans, fillagrin and link (collagen-induced arthritis, adjuvant-induced arthritis, rheumatoid arthritis); desmin (psoriasis); S-antigen (uveitis); insulin, glutamic acid decarboxylase (NOD, type I diabetes); tropomyosin (inflammatory bowel disease); epidermal cadherin (pemphigus vulgaris); Sm, RNP, histones (systemic lupus erythematosus); thyroid stimulating hormone receptor (Grave's disease); thyroglobulin, peroxidase (Hashimoto's thyroiditis); collagen type IV (Goodpasture's syndrome); platelet integrin a IIb: IIIa (autoimmune thrombocytopenia purpura); Rh blood group 1 antigen (autoimmune hemolytic anemia); and acetylcholine receptor (myasthenia gravis). For allotransplation, allopeptides or allogeneic T cells can serve as tolerogens.

Immunomodulatory agents that induce an active immune response include vaccines that elicit an immune response that specifically or non-specifically targets pathogenic T cells. Non-specific vaccines include, for example, vaccines containing antigens present on all or most T cells (e.g. CD2, CD3, CD4, CD5, CD6, CD7, CD8, CD27, CD28, CD32, CD43, and T cell receptor constant regions).

T cells express on their surface a heterodimeric T cell receptor, composed of either α/β chains or γ/δ chains. There are now known to be at least 24β chain variable region gene families, some of which have multiple family members, and also a large number of α chain variable region gene families. It is well established that many autoimmune and infectious pathologies are mediated by T cells expressing a limited repertoire of T cell receptors, which are clonally expanded in response to antigen or superantigen stimulation. For example, EAE has been demonstrated to be associated with rodent Vβ8.2 (BV8S2) expressing T cells; psoriasis with human Vβ3, Vβ13.1 and Vβ17 expressing T cells; diabetes with human Vβ6.1, Vβ6.6/6.7 and Vβ14 expressing T cells; multiple sclerosis with Vβ2, Vβ5 (e.g. Vβ5.1 and Vβ5.2), Vβ6 (e.g. Vβ6.1, Vβ6.2, Vβ6.5, Vβ6.7), Vβ7 and Vβ13 expressing T cells; and rheumatoid arthritis and certain superantigen-mediated infectious diseases with Vβ3, Vβ14 and Vβ17 expressing T cells. Clonally expanded populations of T cells are also associated with T cell proliferative pathologies, such as T cell leukemia and T cell lymphoma.

Those skilled in the art can determine the T cell receptor or receptors present on the relevant pathogenic T cells for the particular pathology or particular individual using methods described, for example, in U.S. Pat. Nos. 5,612,035; 5,861, 164; 6,007,815; 5,837,246; 5,985,552; 5,614,192; 5,223,426; 6,113,903, and 5,776,459, and in PCT publications 95/21623; 93/06135; 94/25063; 99/27957 and 95/00658. Briefly, as described in these references, T cell receptor usage by the relevant T cells (such as CD25+ activated T cells, antigen-responsive T cells, or T cells from the site of the pathology) can be determined by the polymerase chain reaction using a panel of V-region specific primers, or by using anti-TCR antibodies.

Administration of T cell clones expressing T cell receptors associated with the particular pathology, or administration of the corresponding intact dimeric T cell receptors, full-length single T cell receptor chains or portions thereof, variable region peptides or portions thereof, or complementarity determining region peptides (e.g. the CDR1, CDR2, CDR3 or CDR4 region) or portions thereof, and analogs of these sequences, alone or in combination, have been shown to induce immune responses specific for the pathogenic T cells that reduce the activity or number of pathogenic T cells. Thus, such molecules can be used as immunomodulatory agents in combination with low dose estrogen administration to reduce the severity of immune pathologies.

The sequences of T cell receptor α, β, γ or δ variable and constant regions from a variety of species are well known in the art (see, for example, Genevee et al., *Eur J. Immunol.* 22:1261-1269 (1992); Arden et al., *Immunogenetics* 42:455-500 (1995); Choi et al., *Proc. Natl. Acad. Sci. USA* 86:8941-8945 (1989); Concannon et al., *Proc. Natl. Acad. Sci. USA* 83:6598-6602 (1986); Kimura et al., *Eur J. Immunol.* 17:375-383. (1987); Robinson, *J. Immunol.* 146: 4392-4397 (1991); and the EMBL alignment database under alignment accession number DS23485)). Methods of preparing and administering T cell receptors, single chains, and characteristic peptides therefrom, so as to stimulate an immune response specific for the corresponding pathogenic T cell, are described, for example, in Example II, below, as well as in the patents and PCT publications referenced above. Single chain peptides can contain, for example, from about 8 to about 100 amino acids, such as from about 10 to about 50 amino acids, including from about 15 to about 30 amino acids.

Advantageously, T cell receptor heterodimers, individual T cell receptor chains, T cell receptor variable regions, and fragments from any of these molecules can contain or consist of amino acid sequences from the CDR2 hypervariable region. The location of the CDR2 region for each variable chain is known in the art, and is generally at about amino acid residues 38-58 of most human Vβs and Vαs. Exemplary TCR peptides that include some or all of a Vβ (BV) or Vα (VA) CDR2 region are shown in Table 2:

TABLE 2

| TCR | Amino Acid Sequence | SEQ ID NO: |
|---|---|---|
| Vβ3 | LGLRLIYFSYDVKMKEKGDI | 1 |
| Vβ5.2 | ALGQGPQFIFQYYEEEERQRG | 2 |
| Vβ5.2 (Y49T) | ALGQGPQFIFQTYEEEERQRG | 3 |
| Vβ6.1 | LGQGPEFLIYFQGTGAADDSG | 4 |
| Vβ6.5 | LGQGPEFLTYFQNEAQLEKS | 5 |
| Vβ13 | GLRLIHYSVGAGITDQGEV | 6 |
| Vβ14 | SMNVEVTDKGDVPEGYK | 7 |
| Vβ17 | SQIVNDFQKGDIAEGYS | 8 |
| BV1S1A1N1 | SLDQGLQFLIQYYNGEERAKG | 9 |
| BV1S1A2 | SLDQGLQFLIHYYNGEERAKG | 10 |
| BV2S1A1 | FPKQSLMLMATSNEGSKATYE | 11 |
| BV2S1A3N1 | FPKKSLMLMATSNEGSKATYE | 12 |
| BV2S1A4T | FPKQSLMLMATSNEGCKATYE | 13 |
| BV2S1A5T | FPKKSLMQIATSNEGSKATYE | 14 |
| BV3S1 | DPGLGLRLIYFSYDVKMKEKG | 15 |
| BV4S1A1T | QPGQSLTLIATANQGSEATYE | 16 |
| BV5S1A1T | TPGQGLQFLFEYFSETQRNKG | 17 |

TABLE 2-continued

| TCR | Amino Acid Sequence | SEQ ID NO: |
|---|---|---|
| BV5S1A2T | TLGQGLQFLFEYFSETQRNKG | 18 |
| BV5S2 | ALGQGPQFIFQYYEEEERQRG | 19 |
| BV5S3A1T | VLGQGPQFIFQYYEKEERGRG | 20 |
| BV5S4A1T | ALGLGLQLLLWYDEGEERNRG | 21 |
| BV5S4A2T | ALGLGLQFLLWYDEGEERNRG | 22 |
| BV5S6A1T | ALGQGPQFIFQYYREEENGRG | 23 |
| BV6S1A1N1 | SLGQGPEFLIYFQGTGAADDS | 24 |
| BV6S1A3T | SLGQGPELLIYFQGTGAADDS | 25 |
| BV6S2A1N1T | ALGQGPEFLTYFQNEAQLDKS | 26 |
| BV6S3A1N1 | ALGQGPEFLTYFNYEAQQDKS | 27 |
| BV6S4A1 | TLGQGPEFLTYFQNEAQLEKS | 28 |
| BV6S4A4T | NPGQGPEFLTYFQNEAQLEKS | 29 |
| BV6S5A1N1 | SLGQGLEFIYFQGNSAPDKS | 30 |
| BV6S6A1T | ALGQGPEFLTYFNYEAQPDKS | 31 |
| BV6S8A2T | TLGQGSEVLTYSQSDAQRDKS | 32 |
| BV7S1A1N1T | KAKKPPELMFVYSYEKLSINE | 33 |
| BV7S2A1N1T | SAKKPLELMFVYSLEERVENN | 34 |
| BV7S3A1T | SAKKPLELMFVYNFKEQTENN | 35 |
| BV8S1 | TMMRGLELLIYFNNNVPIDDS | 36 |
| BV8S3 | TMMQGLELLAYFRNRAPLDDS | 37 |
| BV9S1A1T | DSKKFLKIMFSYNNKELIINE | 38 |
| BV10S1P | KLEEELKFLVYFQNEELIQKA | 39 |
| BV10S2O | TLEEELKFFIYFQNEEIIQKA | 40 |
| BV11S1A1T | DPGMELHLIHYSYGVNSTEKG | 41 |
| BV12S1A1N1 | DPGHGLRLIHYSYGVKDTDKG | 42 |
| BV12S2A1T | DLGHGLRLIHYSYGVQDTNKG | 43 |
| BV12S2A2T | DLGHGLRLIHYSYGVKDTNKG | 44 |
| BV12S2A3T | DLGHGLRLIHYSYGVHDTNKG | 45 |
| BV12S3 | DLGHGLRLIYYSAAADITDKG | 46 |
| BV13S1 | DPGMGLRLIHYSVGAGITDQG | 47 |
| BV13S2A1T | DPGMGLRLIHYSVGEGTTAKG | 48 |
| BV13S3 | DPGMGLRLIYYSASEGTTDKG | 49 |
| BV13S4 | DPGMGLRRIHYSVAAGITDKG | 50 |
| BV13S5 | DLGLGLRLIHYSNTAGTTGKG | 51 |
| BV13S6A1N1T | DPGMGLKLIYYSVGAGITDKG | 52 |
| BV13S7 | DPGMGLRLIYYSAAGTTDKE | 53 |
| BV14S1 | DPGLGLRQIYYSMNVEVTDKG | 54 |
| BV15S1 | DPGLGLRLIYYSFDVKDINKG | 55 |
| BV16S1A1N1 | VMGKEIKFLLHFVKESKQDES | 56 |

TABLE 2-continued

| TCR | Amino Acid Sequence | SEQ ID NO: |
|---|---|---|
| BV17S1A1T | DPGQGLRLIYYSQIVNDFQKG | 57 |
| BV17S1A2T | DPGQGLRLIYYSHIVNDFQKG | 58 |
| BV18S1 | LPEEGLKFMVYLQKENIIDES | 59 |
| BV19S1P | NQNKEFMLLISFQNEQVLQET | 60 |
| BV19S2O | NQNKEFMFLISFQNEQVLQEM | 61 |
| BV20S1A1N1 | AAGRGLQLLFYSVGIGQISSE | 62 |
| BV20S1A1N3T | AAGRGLQLLFYSIGIDQISSE | 63 |
| BV21S1 | ILGQGPELLVQFQDESVVDDS | 64 |
| BV21S2A1N2T | NLGQGPELLIRYENEEAVDDS | 65 |
| BV21S3A1T | ILGQGPKLLIQFQNNGVVDDS | 66 |
| BV22S1A1T | ILGQKVEFLVSFYNNEISEKS | 67 |
| BV23S1A1T | GPGQDPQFFISFYEKMQSDKG | 68 |
| BV23S1A2T | GPGQDPQFLISFYEKMQSDKG | 69 |
| BV24S1A1T | KSSQAPKLLFHYYNKDFNNEA | 70 |
| BV24S1A2T | KSSQAPKLLFHYYDKDFNNEA | 71 |
| BV25S1A1T | VLKNEFKFLISFQNENVFDET | 72 |
| BV25S1A3T | VLKNEFKFLVSFQNENVFDET | 73 |
| AV1S1 | YPGQHLQLLLKYFSGDPLVKG | 77 |
| AV1S2A1N1T | YPNQGLQLLLKYTSAATLVKG | 78 |
| AV1S2A4T | YPNQGLQLLLKYTTGATLVKG | 79 |
| AV1S2A5T | YPNQGLQLLLKYTSAATLVKG | 80 |
| AV1S3A1T | YPNQGLQLLLKYLSGSTLVES | 81 |
| AV1S3A2T | YPNQGLQLLLKYLSGSTLVKG | 82 |
| AV1S4A1N1T | SPGQGLQLLLKYFSGDTLVQG | 83 |
| AV1S5 | HPNKGLQLLLKYTSAATLVKG | 84 |
| AV2S1A1 | YSGKSPELIMFIYSNGDKEDG | 85 |
| AV2S1A2 | YSGKSPELIMSIYSNGDKEDG | 86 |
| AV2S2A1T | YSRKGPELLMYTYSSGNKEDG | 87 |
| AV2S2A2T | YSRIGPELLMYTYSSGNKEDG | 88 |
| AV2S3A1T | DCRKEPKLLMSVYSSGNEDGR | 89 |
| AV3S1 | NSGRGLVHLILIRSNEREKHS | 90 |
| AV4S1 | LPSQGPEYVIHGLTSNVNNRM | 91 |
| AV4S2A1T | IHSQGPQYIIHGLKNNETNEM | 92 |
| AV4S2A3T | IHSQGPQNIIHGLKNNETNEM | 93 |
| AV5S1 | DPGRGPVFLLLIRENEKEKRK | 94 |
| ADV6S1A1N1 | SSGEMIFLIYQGSYDQQNATE | 95 |
| AV6S1A2N1 | SSGEMIFLIYQGSYDEQNATE | 96 |
| AV7S1A1 | HDGGAPTFLSYNALDGLEETG | 97 |
| AV7S1A2 | HDGGAPTFLSYNGLDGLEETG | 98 |
| AV7S2 | HAGEAPTFLSYNVLDGLEEKG | 99 |
| AV8S1A1 | ELGKRPQLIIDIRSNVGEKKD | 100 |
| AV8S1A2 | ELGKGPQLIIDIRSNVGEKKD | 101 |
| AV8S2A1N1T | ESGKGPQFIIDIRSNMDKRQG | 102 |
| AV9S1 | YSRQRLQLLLRHISRESIKGF | 103 |
| AV10S1A1 | EPGEGPVLLVTVVTGGEVKKL | 104 |
| AV11S1A1T | FPGCAPRLLVKGSKPSQQGRY | 105 |
| AV12S1 | PPSGELVFLIRRNSFDEQNEI | 106 |
| AV13S1 | NPWGQLINLFYIPSGTKQNGR | 107 |
| ADV14S1 | PPSRQMILVIRQEAYKQQNAT | 108 |
| AV15S1 | EPGAGLQLLTYIFSNMDMKQD | 109 |
| AV16S1A1T | YPNRGLQFLLKYITGDNLVKG | 110 |
| ADV17S1A1T | FPGKGPALLIAIRPDVSEKKE | 111 |
| AV18S1 | ETAKTPEALFVMTLNGDEKKK | 112 |
| AV19S1 | HPGGGIVSLFMLSSGKKKHGR | 113 |
| AV20S1 | FPSQGPRFIIQGYKTKVTNEV | 114 |
| AV21S1A1N1 | YPAEGPTFLISISSIKDKNED | 115 |
| AV22S1A1N1T | YPGEGLQLLLKATKADDKGSN | 116 |
| AV23S1 | DPGKGLTSLLLIQSSQREQTS | 117 |
| AV24S1 | DTGRGPVSLTIMTFSENTKSN | 118 |
| AV25S1 | DPGEGPVLLIALYKAGELTSN | 119 |
| AV26S1 | KYGEGLIFLMMLQKGGEEKSH | 120 |
| AV27S1 | DPGKSLESLFVLLSNGAVKQE | 121 |
| AV28S1A1T | QEKKAPTFLFMLTSSGIEKKS | 122 |
| AV29S1A1T | KHGEAPVFLMILLKGGEQMRR | 123 |
| AV29S1A2T | KHGEAPVFLMILLKGGEQKGH | 124 |
| AV30S1A1T | DPGKGPEFLFTLYSAGEEKEK | 125 |
| AV31S1 | YPSKPLQLLQRETMENSKNFG | 126 |
| AV32S1 | RPGGHPVFLIQLVKSGEVKKQ | 127 |

Exemplary combinations of TCR peptides that can be used in combination with low dose estrogen for preventing or reducing the severity of autoimmune diseases include, for multiple sclerosis, Vβ5.2, Vβ6.5 and/or Vβ13 (e.g. SEQ ID NOS:2, 3, 5 and/or 6); for rheumatoid arthritis, Vβ3, Vβ14 and/or Vβ17 (e.g. SEQ ID NOS:1, 7 and/or 8); and for psoriasis, Vβ3 and/or Vβ33 (e.g. SEQ ID NOS:1 and/or 6). Other appropriate combinations of TCR peptides can be determined by the skilled person according to the pathogenic TCRs expressed by the particular individual.

Alternatively, analogs of the T cell receptors and peptides can be used in the methods of the invention. As used herein, the term "T cell receptor analog" refers to a sequence with minor modifications, so long as the analog retains the ability to induce a substantially similar cell mediated or humoral immune response against the T cell receptor as the receptor or portion having the native sequence. A T cell receptor analog can thus have one, two or several amino acid deletions, additions or substitutions, with respect to the native sequence. For example, a T cell receptor analog can have a single amino acid substitution, or substitutions at 2, 3, 4 or more positions with respect to the sequences listed in Table 2. Such analogs can advantageously have improved stability, bioavailability, bioactivity or immunogenicity as compared to the native sequence. An exemplary analog of a Vβ sequence is the (Y49T) BV5S2-3858 peptide having the amino acid sequence ALGQGPQFIFQTYEEEERQRG (SEQ ID NO:3), which is a singly substituted analog of the naturally occurring BV5S2-38-58 peptide.

A TCR analog can have, for example, at least 70%, such as at least 80%, 90%, 95%, 98% or greater identity with the naturally occurring sequence over the entirety of the sequence. A TCR analog can be encoded by a nucleic acid sequence having at least 70%, such as at least 80%, 90%, 95%, 98% or greater identity with the naturally occurring sequence over the entirety of the sequence. Those skilled in the art can readily make and test peptide analogs, by either in vitro or in vivo assays, to determine whether they retain the immunological activity of the naturally occurring sequence. Additionally, computer programs that predict sequences containing B and T cell epitopes are known in the art, and can be used to guide the choice of amino acid substitutions, additions or deletions (see, for example, Savoie et al., *Pac. Symp. Biocomput.* 1999:182-189 (1999); Cochlovius et al., *J. Immunol.* 165:4731-4741 (2000)).

As shown in Example II, below, the combination of low dose estrogen and a Vβ8.2 peptide acted synergistically to result in complete protection against the autoimmune disease EAE. Thus, T cell receptor peptide therapies, as described above, can advantageously be combined with low dose estrogen therapy to reduce the severity of immune pathologies mediated by T cells expressing a limited repertoire of T cell receptors, including both autoimmune pathologies and T cell malignancies.

Alternatively, an expressible nucleic acid construct encoding an intact dimeric T cell receptor, a full-length single T cell receptor chain, a variable region peptide or portion thereof, or hypervariable region peptide (e.g. the CDR2 region) or portion thereof, or analog of such sequences, can be administered to a mammal. The nucleic acid can be inserted into a plasmid vector, viral vector, or alternatively not be inserted into a vector. Those skilled in the art can determine the appropriate mammalian promoter and regulatory elements, route of administration and dose of nucleic acid required to induce an immune response against the pathogenic T cells. Preferred routes of administration of an expressible nucleic acid are intramuscular and intradermal. The use of expressible nucleic acid molecules encoding peptides to induce an immune response are described, for example, in U.S. Pat. No. 5,580,859. The use of expressible nucleic acid molecules encoding T cell receptor peptides to elicit an immune response against pathogenic T cells is described, for example, in U.S. Pat. Nos. 5,939,400, 6,113,903 and 6,207,645.

Similar immunotherapeutic methods as described above with respect to T cell receptors can be used to induce an immune response against an HLA molecule associated with an immune disease. For example, expression of HLA-DR1 and some subtypes of HLA-DR4 (e.g. Dw4) are strongly associated with rheumatoid arthritis (RA); expression of HLA-B27 is strongly associated with ankylosing spondylitis and reactive arthritis; expression of HLA-DR15, DQG and Dw2 with multiple sclerosis (MS); HLA-DR3 and HLA-DR4 with diabetes; and HLA-DR2 and HLA-DR3 with lupus. Thus, HLA molecules associated with immune pathologies and characteristic portions thereof, and nucleic acid molecules encoding such polypeptides, can be used as immunotherapeutic agents in combination with estrogen therapy to reduce the severity of immune pathologies. The association of HLA haplotypes with immune pathologies and methods of using HLA molecules as immunotherapeutic agents are described, for example, in U.S. Pat. No. 6,045,796.

Immunomodulatory agents can advantageously be administered in combination with an adjuvant suitable for administration to the particular mammal. For humans, exemplary adjuvants include Incomplete Freund's Adjuvant, alum, and Detox™. Optionally, immunomodulatory agents can be conjugated to carrier molecules. Suitable adjuvants and carriers are well known in the art.

As used herein, an "immunoblocking agent" refers to any molecule that interferes with the interaction of the trimolecular complex between a T cell receptor, an HLA and an antigen. For example, an immunoblocking agent can be an antibody directed against and specific for a T cell receptor chain, such as specific for a rodent Vβ8.2, or human Vβ2, Vβ3, Vβ5.1, Vβ5.2, Vβ6.1, Vβ6.2, Vβ6.5, Vβ6.7, Vβ7, Vβ13, Vβ14 or Vβ17 chain. Methods of using antibodies as T cell receptor immunoblocking agents are described, for example, in Acha-Orbea et al., *Cell* 54:263-273 (1988) and U.S. Pat. Nos. 5,223,426, 6,221,352 and 6,113,903.

Likewise, an immunoblocking agent can be an antibody directed against an antigen, such as the antigens associated with immune pathologies described above, or an antibody directed against an HLA antigen associated with an immune pathology, as described above.

As used herein, the term "antibody" refers to a polyclonal, monoclonal, chimeric or single chain antibody, or antigen-binding fragment therefrom (such as as a Fab or Fab2 fragment), that binds an antigen with high affinity (Kd<about $10^5$M) and high specificity. Methods of preparing antibodies specific for any given target molecule are well known in the art.

An immunoblocking agent can further by a complex of an antigenic peptide and an HLA molecule as described, for example, in U.S. Pat. No. 5,194,425.

An immunoblocking agent can also be a non-antibody agent that specifically binds a desired target molecule on a pathogenic T cell (e.g. T cell receptor, antigen or HLA). Libraries of naturally occurring and synthetic compounds, including inorganic compounds, peptides, lipids, saccharides, nucleic acids and small organic molecules, are commercially available, and can be screened in high-throughput assays to binding agents. Such agents can then be tested in in vitro or in vivo assays to determine their efficacy in blocking activation of pathogenic T cells.

For example, an immunoblocking agent can be an altered peptide ligand. As used herein, the term "altered peptide ligand" refers to an analog of an antigenic peptide (such as the autoantigenic peptides described above), in which the TCR contact residues have been altered, such that the peptide binds the HLA molecules with similar affinities as the wild-type peptide, but does not stimulate T cell proliferative responses. Methods of making and using altered peptide ligands of a variety of antigenic peptides are described, for example, in Evavold et al., *Immunology Today* 14:602-609 (1993), in Fairchild, Eur. J. Immunogenet. 24:155-167 (1997), and in U.S. Pat. No. 6,197,926.

Advantageously, an antibody or other immunoblocking agent can further be attached to a toxic moiety, such as a chemotherapeutic agent or radioisotope to kill or inhibit proliferation of target cells. Such moieties and methods of attaching them to immunoblocking agents are known in the art.

An immunotherapeutic agent can alternatively be an agent that acts by a mechanism that is not specific for the trimolecular T cell receptor-antigen-HLA complex. Such agents include, for example, agents that modulate levels, production or function of cytokines, chemokines or their receptors. Those skilled in the art understand which sorts of agents will be effective in relation to different immune pathologies. For example, for treatment of Th1-mediated pathologies, useful agents include those that decrease Th1-type and/or increase Th2-type cytokine levels or activity.

Binding domains from the TNFα receptor (e.g. Enbrel™), or antibodies or other agents that bind to or block the function of TNFα (e.g. etanercept; infliximab), are exemplary immunotherapeutic agents that inhibit Th1 immune responses. Other agents include the naturally occurring IL-1 receptor antagonist (IL-Ira). Additionally, useful immunotherapeutic agents include general immunosuppressive agents such as corticosteroids, cyclosporine and FK506; anti-inflammatory cytokines such as IL-4, IL-10, TGF-β and interferons (e.g. interferon (IFN)beta-1a (Avonex™); IFNbeta-1b (Betaseron™); Rebif™); agents that non-specifically interfere with TCR/HLA/antigen interactions (e.g. the basic four-amino acid copolymer known as glatiramer acetate (Copaxone™)); antineoplastic agents (e.g. mitoxantrone (Novantrone™); purine analogs (e.g. 2-chlorodeoxyadenosine (cladribine); 2'-deoxycorfomycin (pentostatin)) as well as methotrexate, Cox-2 inhibitors (e.g. etoricoxib), phosphodiesterase inhibitors, leflunomide and the like, and various combinations of the above agents.

The invention also provides kits containing a low dose of estrogen and an immunotherapeutic agent, wherein administration of the low dose of estrogen and the immunotherapeutic agent reduce the severity of a Th1-mediated immune pathology in a mammal. Appropriate kit components and immunotherapeutic agents for treatment of various pathologies have been described above.

As used herein, the term "kit" refers to components intended for use together, which may be in the same or separate containers. An indication that components of a kit are for use together can be, for example, packaging of containers containing the components in a single package, or labeling either or both of the components as being for use in combination, or both. Such kits can further contain written instructions for use of the low dose estrogen formulation and immunotherapeutic agent in combination to reduce the severity of an immune pathology. Written instructions can, for example, set forth the clinical indication, as well as the amount, frequency, and method of administration of the kit components.

It will be appreciated that the estrogen formulation and agent formulation need not be the same. For example, the agent can be formulated for administration by injection, or other appropriate route, whereas the estrogen can be formulated for implantation, oral administration, inhalation or administration by another appropriate route. Other formulations for the components of the kit can be determined by those skilled in the art, following the guidance provided above in relation to methods for reducing the severity of immune pathologies.

In addition to the active ingredients, the low dose estrogen and immunotherapeutic agent can be formulated with suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The kit components are provided in an effective amount to achieve the intended purpose. The determination of an effective dose is well within the capability of those skilled in the art. For any compound, the therapeutically effective dose can be estimated initially either in cell culture assays, or in animal models, usually mice, rats, rabbits, dogs, or pigs. The animal model may also be used to determine the appropriate concentration range and route of administration. Such information can then be used to determine useful doses and routes for administration in humans.

A therapeutically effective dose refers to that amount of active ingredient which ameliorates the symptoms or condition. Therapeutic efficacy and toxicity can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts of the immunotherapeutic agent may vary from 0.1 µg to 100 mg, up to a total dose of about 1 g, depending upon the route of administration. Guidance as to particular dosages and methods of delivery is provided in the literature and generally available to practitioners in the art.

The following examples are intended to illustrate but not limit the present invention.

EXAMPLE I

Effect of Low-Dose Estrogen Therapy on an Immune Pathology

This example shows that administration of a low dose of either of two forms of estrogen, to either males or females, in two distinct animal models of multiple sclerosis, effectively reduced the incidence and severity of the disease. The reduction in clinical disease was accompanied by a significant decline in the number of inflammatory and demyelinating foci in the central nervous system. T lymphocytes from estrogen treated mice demonstrated a modest reduction in proliferation and a shift in cytokine production. Thus, low dose estrogen therapy is an effective method of reducing the severity of immune pathologies in mammals.

Materials and Methods

Animals. Age matched SJL/J and B10.PL mice were purchased from Jackson Laboratory (Bar Harbor, Me.). Young adult (10 weeks old or less) mice were used for the experiments in this Example. The animals were housed in the Animal Resource Facility at the Portland Veterans Affairs Medical Center in accordance with institutional guidelines.

Antigens. Mouse proteolipid protein peptide 139-151 (HCLGKWLGHPDKF) (SEQ ID NO:74) and myelin basic protein peptide Acl-11 (Ac-ASQKRPSQRSK) (SEQ ID NO:75) were synthesized using solid phase chemistry on a Synergy 432A peptide synthesizer (Applied Biosystems, Foster City, Calif.), and purified prior to use.

Estrogen treatment and measurement of serum estrogen levels. Sixty-day release pellets of 17-β estradiol (E2), estriol (E3) and placebo pellets were implanted subcutaneously in the scapular region behind the neck using a 12 gauge trochar as described by the manufacturer (Innovative Research, Sarasota, Fla.). The mice were implanted one week prior to immunization with the appropriate myelin antigen. Representative animals were bled by cardiac puncture, and the blood was allowed to clot at 4° C. overnight. The samples were centrifuged, the sera collected, and stored at −80° C. until hormone analysis was performed. Serum levels of E2 and E3 were determined by radioimmunoassay (RIA) after Sephadex LH-20 column chromatography. All samples were analyzed in a single assay for each hormone.

Induction of EAE. SJL mice were inoculated subcutaneously in the flanks with 0.2 ml of an emulsion containing 150 μg of PLP 139-151 in saline and an equal volume of complete Freund's Adjuvant (CFA) containing 200 μg of *Mycobacterium tuberculosis* H37RA (Difco Laboratories, Detroit, Mich.). B10.PL mice were immunized with an emulsion containing 400 μg of MBP Acl-11 and 200 μg of *Mycobacterium tuberculosis*. Disease induction in B10.PL mice required treatment with pertussis toxin on the day of immunization (75 ng/mouse) and 2 days later (200 ng/mouse). The mice were examined daily for clinical signs of disease and scored according to the following scale: 0, normal; 1, minimal or mild hind limb weakness; 2, moderate hind limb weakness or mild ataxia; 3, moderately severe hind limb weakness; 4, severe hind limb weakness or moderate ataxia; 5, paraplegia with no more than moderate forelimb weakness; 6, paraplegia with severe forelimb weakness or severe ataxia.

Histopathology. The intact spinal column was removed from mice during the peak of clinical disease and fixed in 10% phosphate buffered formalin. The spinal cords were dissected after fixation, and embedded in paraffin prior to sectioning. The sections were stained with luxol fast blue-periodic acid schiff-hematoxylin and analyzed by light microscopy. Semi-quantitative analysis of inflammation and demyelination was determined by examining at least ten sections from each mouse.

Immunofluorescent staining for flow cytometry. Draining lymph node (DLN) cells were removed during the peak of clinical symptoms and analyzed for the expression of cell surface proteins by fluorescent staining ex vivo. The following fluorochrome conjugated antibodies obtained from Pharmingen Inc. (San Diego, Calif.) were used for the direct staining of DLN cells: anti-CD4, anti-CD25, anti-CD69, anti-CD95L, anti-CD44, anti-CD62L, anti-CD49d. Two-color immunofluorescent analysis was performed on a FACScan instrument (Becton Dickinson, Mountain View, Calif.) using Cellquest software. For each experiment the cells were stained with isotype control antibodies to establish background staining, and to set the quadrants prior to calculating the percent positive staining cells.

Proliferation Assays. DLN cells were recovered from immunized mice at peak of clinical EAE (days 12-16 post-immunization) as described in Bebo et al., *J. Immunol.* 162:35 (1998)). The in vitro proliferative response was determined using a standard microtiter assay (Bourdette et al., *Cell Immunol.* 112:351 (1988)). Briefly, DLN cells were cultured in 96 well, flat bottom tissue culture plates at $4\times10^5$ cells per well in stimulation medium alone (control), or with test antigens (i.e. PLP 139-151) and incubated for 3 days at 37° C. in 7% $CO_2$. Wells were pulsed for the final 18 hr with 0.5 mCi of [$^3$H] methylthymidine (Amersham, Arlington Heights, Ill.). The cells were harvested onto glass fiber filters and tritiated thymidine uptake measured by a liquid scintillation counter. Results were determined from the means of triplicate cultures. Stimulation indices were determined by calculating the ratio of antigen specific cpm to control cpm.

Cytokine detection by ELISA. DLN cells were cultured at $4\times10^6$/ml and stimulated with the appropriate antigen in 24 well culture plates. Cell culture supernatants were recovered between 48-72 hr and frozen at −70° C. until needed for the cytokine assay. Measurement of cytokines was performed by ELISA using cytokine specific capture and detection antibodies (Pharmingen). Standard curves for each assay were generated using recombinant mouse cytokines (Pharmingen), and the concentration of cytokines in the cell supernatants was determined by interpolation from the appropriate standard curve. IFN-γ, TNF-α and IL-12 were chosen as representative Th1 cytokines, while IL-4 and IL-10 were measured as representative Th2 cytokines.

PLP 139-151 specific antibody ELISA. Nunc-Immuno 96 well ELISA plates (Nunc, Inc, Denmark) were coated with PLP 139-151 at 4 μg/ml in phosphate buffered saline (PBS) overnight at 4° C. The plates were washed and blocked prior to the addition of serum at the indicated dilution in triplicates. The samples were incubated overnight at 4° C. and the plate was washed prior to the addition of an affinity purified, biotinylated goat anti-mouse Ig (diluted 1:10,000) detecting antibody (Accurate Antibodies, Westbury, N.Y.). The plates were incubated for one hour at room temperature before they were washed. A 1:400 dilution of avidin-peroxidase conjugate (Sigma, St. Louis, Mo.) was added to each well and the plates were incubated for an additional 45 mins. After the final wash, a peroxidase substrate (3,3',5,5-tetramethylbenzidine, Kirkgaard & Perry Laboratories, Gaithersburg, Md.) was added to the wells and the reaction was stopped by the addition of 0.18 M sulfuric acid. The plates were read in a Vmax kinetic microplate reader (Molecular Devices, Inc., Sunnyvale, Calif.) at 450 nm. Wells coated with an irrelevant peptide (myelin oligodendrocyte glycoprotein 35-55) acted as a negative control.

Statistics. Cumulative disease index (CDI) was defined as the mean of the sum of the daily scores. Significant differences in disease incidence between placebo and estrogen treated mice were determined by chi square analysis and significant differences in disease onset, severity at peak of disease and CDI were determined using the two-tailed student t test.

Results

Low dose 17β-estradiol (E2) treatment reduces the incidence and severity of EAE in SJL mice. The protective effect of estrogen on severity of EAE, an animal model of multiple sclerosis was determined. Female SJL mice were implanted with 60-day release tablets (Innovative Research, Sarasota, Fla.) containing 17-estradiol (E2) one week prior to the active induction of EAE by immunization with proteolipid protein peptide 139-151 (PLP 139-151). The dose of E2 chosen for these studies (Table 3) was intended to mimic the levels of E2 found during pregnancy, estrus or diestrus phases of the hormone cycle (Table 1). E2 levels were measured in representative animals and were determined to be equivalent to those reported by the manufacturer.

TABLE 3

| Pellet (mg) | 17β-estradiol (pg/ml) | Estriol (pg/ml) |
|---|---|---|
| 15 | 9,000-10,000 | 10,000-15,000 |
| 5 | 3,000-4,000 | 5,000-6,000 |
| 2.5 | 1,500-2,000 | 2,000-3,000 |
| 1.5 | 800-1,000 | 800-1,000 |
| 0.36 | 150-200 | 150-200 |
| 0.1 | 25-50 | 40-50 |
| 0.025 | 5-10 | 10-20 |

As shown in FIG. 1 and Table 4, pregnancy levels of E2 reduced the incidence and severity of clinical disease in a manner similar to that reported previously. Unexpectedly, low levels of E2 also profoundly reduced the clinical manifestations of disease. Pellets releasing as little as 25-50 pg of E2 per ml of serum lowered the incidence, delayed the onset, and significantly diminished the severity of paralysis when compared to placebo controls (FIG. 1 and Table 4). In addition, pathological examination revealed a dramatic reduction in mononuclear cell infiltration and demyelination in the spinal cords of E2 protected mice when compared to placebo treated mice (Table 5).

Figure 2:
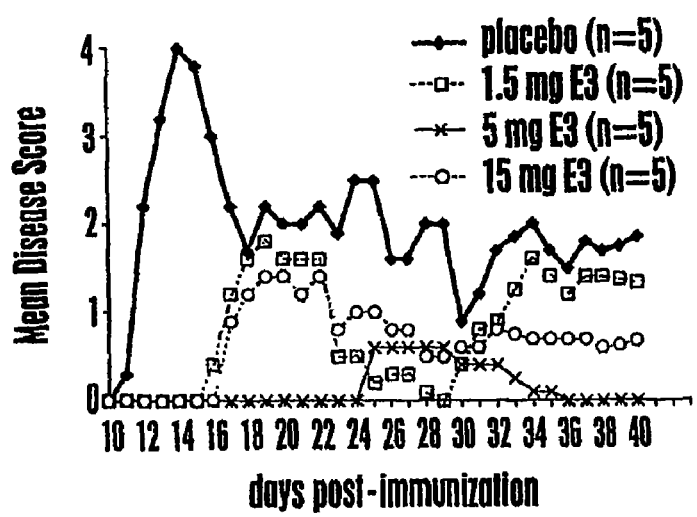
FIG. 2 shows the effect of various concentrations of estriol (E3) on the severity of EAE in female SJL mice.

Low dose estriol (E3) treatment reduces the incidence and severity of EAE in SJL mice. Estriol (E3) is a hormone produced by the placenta, and is at its highest levels during the third trimester. The effects of various doses of ES in the SJL EAE model was determined. As shown in FIG. 2 and Table 6, high dose E3 therapy effectively reduced the incidence and severity of EAE induced by active immunization of female SJL mice with PLP 139-151. Unexpectedly, low dose E3 treatment was also effective. Treatment of female mice with 1.5 mg E3 pellets resulted in serum hormone levels that were half to a third of that known to result from pregnancy (Tables 1 and 3). These mice had a lower incidence, delayed onset, and a significant reduction in the mean peak disease score and cumulative disease index (FIG. 2 and Table 6). The diminution in clinical disease score was accompanied by a substantial reduction in inflammation and demyelination upon pathological examination (Table 5). The direct comparison of E2 and E3 in the same animal model also allowed determination of whether one form of estrogen was more or less potent than the other form. No statistically significant differences (as determined by the Fisher exact test) in the incidence or severity of EAE were found, indicating that E2 and E3 were equally protective.

TABLE 4

| 17β-estradiol (mg/pellet) | Incidence | Onset (days) | Relapse | Peak | CDI |
|---|---|---|---|---|---|
| Placebo | 19/19 (100%) | 12.3 ± 0.4 | 5/10 (50%) | 4.4 ± 0.2 | 30.5 ± 1.2 |
| 0.025 (diestrus) | 15/18 (83%) $p = 0.201^T$ | 15.8 ± 3.5 $p = 0.09$ | 5/9 (56%) $p = 0.843$ | 3.6 ± 1.3 $p = 0.27$ | 19.2 ± 10.0 $p = 0.07$ |
| 0.1 (diestrus) | 12/19 (63%) $p = 0.012$ | 14.5 ± 2.0 $P = 0.07$ | 2/9 (22%) $p = 0.431$ | 2.0 ± 0.9 $P = 0.0002$ | 8.9 ± 3.4 $P < 0.0001$ |
| 0.36 (estrus) | 15/19 (79%) $p = 0.114$ | 15.1 ± 1.3 $P = 0.006$ | 2/9 (22%) $p = 0.431$ | 2.5 ± 0.6 $P < 0.0001$ | 9.8 ± 1.9 $P = 0.0001$ |
| 2.5 (pregnancy) | 4/10 (40%) $p < 0.0001$ | 13.8 ± 0.5 $P = 0.02$ | 0/4 (0%) $p = 0.252$ | 2.0 ± 2.1 $P = 0.06$ | 7.5 ± 7.9 $P = 0.003$ |

TABLE 5

| | Inflammatory foci/section | Demyelinated foci/section |
|---|---|---|
| Placebo | 7.2 ± 3.4 | 4.4 ± 1.8 |
| 0.36 mg E2 | 1.3 ± 0.8* | 0.5 ± 0.3 |
| 2.5 mg E2 | 0.6 ± 0.8 | 0.5 ± 0.4 |
| 2.5 mg E3 | 1.2 ± 0.6 | 0.8 ± 0.2 |
| 5.0 mg E3 | 0.9 ± 0.5 | 0.3 ± 0.2 |

TABLE 6

| Estriol (mg/pellet) | Incidence | Onset (days) | Relapse | Peak | CDI |
|---|---|---|---|---|---|
| Placebo | 10/10 (100%) | 12.7 ± 0.3 | 2/5 (40%) | 4.2 ± 0.2 | 30.2 ± 1.5 |
| 1.5 (low) | 6/10 (60%) $p = 0.094$ | 16.4 ± 0.7 $P = 0.02$ | 0/3 (0%) $p = 0.673$ | 2.0 ± 0.0 $P = 0.004$ | 9.3 ± 2.6 $P = 0.008$ |
| 5.0 (pregnancy) | 2/5 (40%) $p = 0.040$ | 33.5 ± 5.0 $P = 0.03$ | 0/2 (0%) $p = 0.895$ | 1.4 ± 2.2 $P = 0.31$ | 6.5 ± 9 $p = 0.07$ |
| 15.0 (high) | 5/10 (50%) $p = 0.039$ | 23.8 ± 9 $p = 0.22$ | 0/1 (0%) NA | 1.4 ± 1.1 $P = 0.07$ | 4.4 ± 3.5 $P = 0.01$ |

Low dose estrogen therapy reduces the incidence and severity of RAE in B10.PL mice. The effect of E2 and E3 on EAE was examined in B10.PL mice, which are genetically distinct from SJL mice and respond to a different dominant myelin antigen, myelin basic protein peptide Acl-11 (MBP Acl-11). The sensitivity of these mice to estrogen therapy was tested by treating the mice with estrogen containing pellets prior to immunization with MBP Acl-11. Low level E2 treatment reduced the incidence, delayed the onset, and diminished the severity of EAE as reflected by significant differences in mean peak disease score and the cumulative disease index (Table 7).

TABLE 7

| 17β-estradiol (mg/pellet) | Incidence | Onset (days) | Peak | CDT |
|---|---|---|---|---|
| Placebo | 26/30 (87%) | 13.6 ± 0.6 | 4.6 ± 0.34 | 39.3 ± 7.3 |
| 0.18 (diestrus) | 3/6 (50%) p = 0.125 | 25.7 ± 1.2 P < 0.0001 | 1.7 ± 0.92 P < 0.000 | 5.8 ± 2.9 P < 0.0001 |
| 0.36 (estrus) | 15/26 (58%) p = 0.030 | 26.5 ± 1.3 P < 0.0001 | 2.61 ± 0.60 P < 0.0001 | 13.5 ± 6.2 P < 0.0001 |
| 2.50 (pregnancy) | 0/15 (0%) p < 0.0001 | 0 ± 0 NA | 0 ± 0 NA | 0 ± 0 NA |
| 15.0 (high) | 2/8 (25%) p = 0.002 | 29 ± 1.4 P < 0.0001 | 2.0 ± 1.0 P < 0.0001 | 1.4 ± 3.8 P < 0.0001 |

When the cumulative disease indices and peak disease scores were compared (Fisher exact test), no significant differences in E2 sensitivity between SJL and B10.PL mice at low E2 levels were found. However B10.PL mice appeared to be more sensitive to high dose E2 treatment. Strain differences in peak disease score and cumulative disease index were significant in mice receiving 2.5 mg E2 pellets (p=0.005).

E3 also reduced the incidence and severity of disease in B10.PL mice (Table 8), but no differences in sensitivity to E3 were detected between these mice and SJL mice as determined by the Fisher exact test.

TABLE 8

| Estriol (mg/pellet) | Incidence | Onset (days) | Peak | CDI |
|---|---|---|---|---|
| Placebo | 3/4 (75%) | 9.7 ± 0.43 | 4.3 ± 1.4 | 30.5 ± 30.5 |
| 1.5 (low) | 5/8 (38%) p = 0.551$^T$ | 30.3 ± 0.9 P < 0.0001 | 1.38 ± 0.8 P < 0.0001 | 1.9 ± 1.7 P <0.0001 |
| 5 (pregnancy) | 3/8 (38%) p = 0.551 | 31.3 ± 0.7 P < 0.0001 | 0.71 ± 0.4 P < 0.0001 | 1.0 ± 0.5 P <0.0001 |

Figure 3:
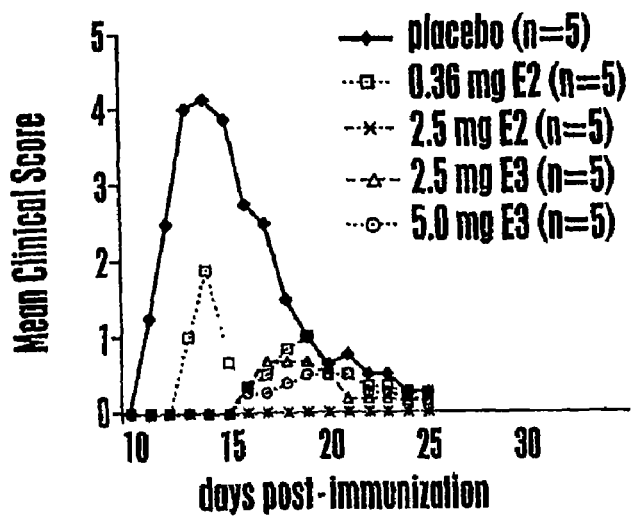
FIG. 3 shows the effect of E2 and E3 on the severity of EAE in male SJL mice.

Male SJL mice are sensitive to estrogen. Estrogen receptors (ER) are expressed both by female and male immunocompetent cells. Because male cells are potentially sensitive to estrogens, estrogen therapy was performed on male SJL mice. Male mice were treated with E2 and E3 containing pellets as described above and one week later they were immunized with PLP 139-151. Treatment with either E2 or E3 delayed the onset and reduced the severity of clinical disease, even at doses equivalent to estrus levels (150-200 pg/ml) in females (FIG. 3 and Table 9). No significant differences in estrogen sensitivity (as determined by the Fisher exact test) were detected between males and females.

TABLE 9

| Treatment (mg/pellet) | Incidence | Onset (days) | Peak | CDI |
|---|---|---|---|---|
| Placebo | 4/4 (100%) | 11.3 ± 0.5 | 4.4 ± 0.8 | 25.4 ± 6.5 |
| 0.36 E2 | 3/4 (75%) p = 1.00$^T$ | 15.3 ± 3.2 P = 0.052 | 2.1 ± 2.4 P = 0.119 | 6.4 ± 5.1 P = 0.004 |
| 2.5 E2 | 0/4 (0%) p = 0.034 | NA | NA | NA |
| 2.5 E3 | 2/3 (67%) p = 0.885 | 16.5 ± 0.7 P < 0.0001 | 0.67 ± 0.6 P = <0.0001 | 3.2 ± 2.5 P = 0.003 |
| 5.0 E3 | 1/4 (25%) p = 0.144 | 16.0 ± 0 p < 0.0001 | 0.50 ± 1.0 P = <0.0001 | 2.6 ± 5.3 P = 0.002 |

Mechanisms governing estrogen mediated regulation of EAE. Alterations in the expression of adhesion or activation markers on T cells are often indicative of functional changes in the cell. Monoclonal antibodies specific for a number of these markers were used to assess whether estrogen therapy altered their expression. Draining lymph node (DLN) cells were recovered from mice during the peak of clinical EAE, incubated with the indicated fluorochrome conjugated monoclonal antibodies, and surface expression measured by fluorescent activated cell analyzer. As shown in Table 10, there were no apparent differences in the number of CD4+ T cells in the DLN from placebo and estrogen treated mice.

TABLE 10

| | % of Total | % of CD4+ T cells | | | | | |
|---|---|---|---|---|---|---|---|
| | CD4 | CD25 | CD69 | FASL | CD44 | CD62L* | CD49d |
| Placebo | 42* | 5.0 | 7.2 | 2.8 | 38 | 7.2 | 36 |
| 0.36 E2 | 49 | 5.9 | 6.6 | 2.7 | 43 | 7.0 | 45 |
| 2.5 E2 | 49 | 6.3 | 6.5 | 4.2 | 41 | 6.7 | 43 |
| 2.5 E3 | 45 | 5.5 | 7.5 | 3.1 | 36 | 12 | 36 |
| 5.0 E3 | 47 | 6.4 | 8.3 | 2.7 | 38 | 8.8 | 37 |

*Representative of two different experiments.

Approximately 5% of the T cells in the DLN presented with an activated phenotype (CD25+, CD69+, FASL+), but no differences between placebo and estrogen treated mice was noted. In addition, no differences in adhesion molecule expression (CD44, CD62L, CD49d) were observed. These data indicate that estrogen therapy had no apparent effect on the phenotype of T lymphocytes in the lymph nodes draining the site of immunization.

Figure 4:
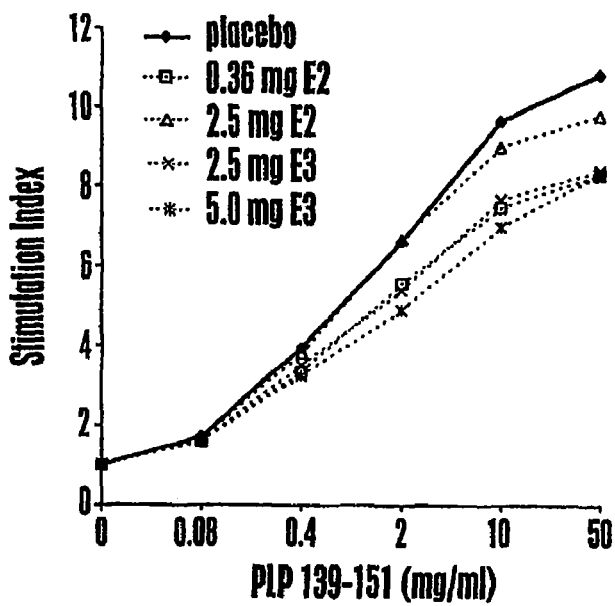
FIG. 4 shows the effect of low dose estrogen therapy on the PLP 139-151 induced proliferation of draining lymph node (DLN) cells from female SJL mice with EAE.

Proliferation of draining lymph node (DLN) T cells from placebo and estrogen treated mice was measured to determine if estrogen therapy adhered the ability of these cells to respond to antigen. DLN T cells were removed from representative animals during the peak of clinical EAE, stimulated with antigen in vitro, and proliferation measured using a standard $^3$H-thymidine incorporation assay. A modest decrease in proliferation to PLP 139-151 was consistently observed in DLN cells isolated from estrogen treated mice (FIG. 4). However, in all cases the reduction in antigen specific proliferation failed to achieve statistical significance. No consistent differences in background, or mitogen-induced proliferation were observed. A similar modest but insignificant reduction in antigen specific proliferation was also observed in the B10.PL model.

Figure 5A:
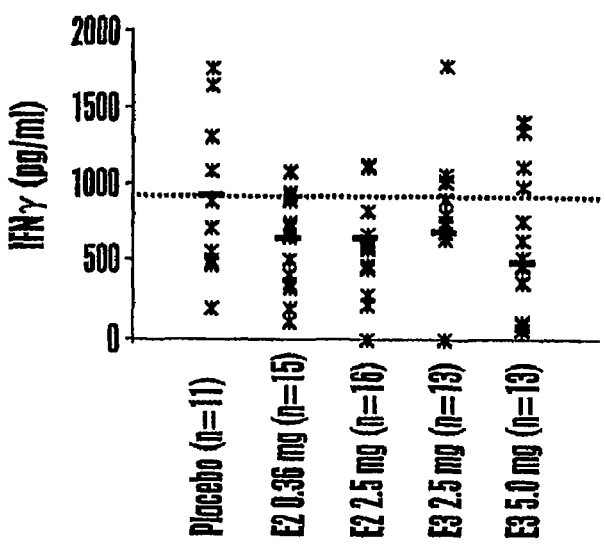
FIG. 5 shows the effect of low dose estrogen therapy on PLP 139-151 induced cytokine production by DLN cells from female SJL mice with EAE.
Figure 5B:
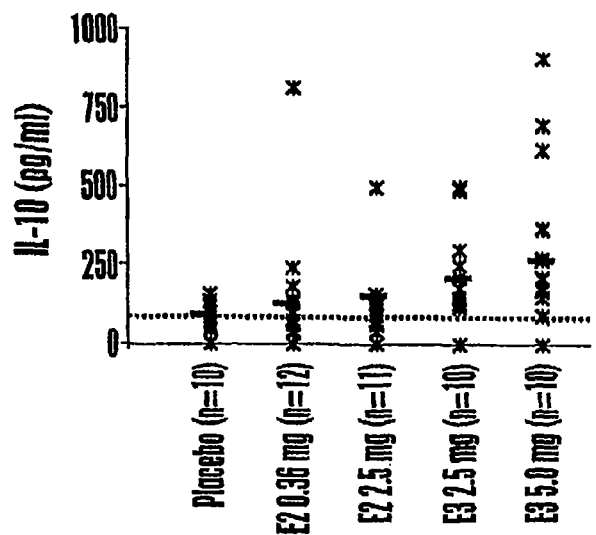
Figure 5C:
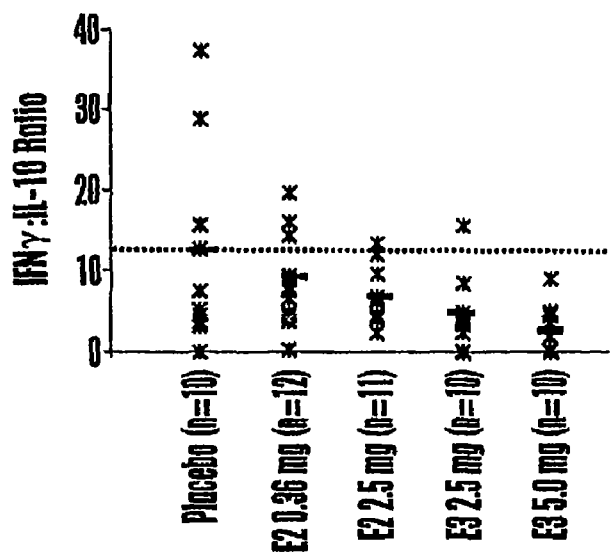
Figure 5D:
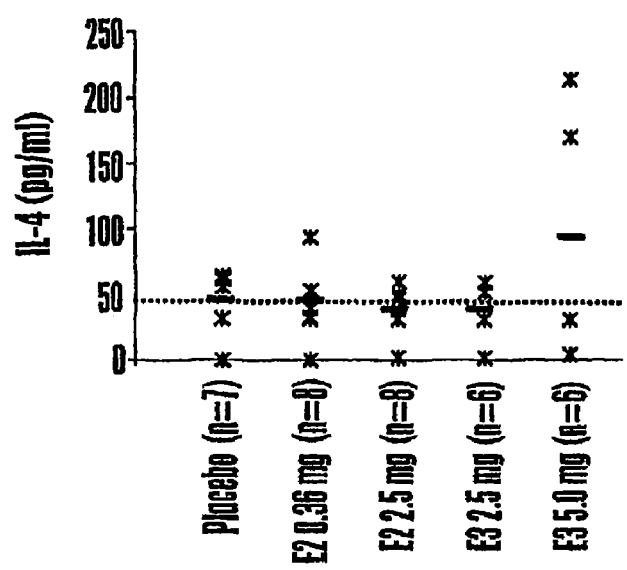
Figure 5E:
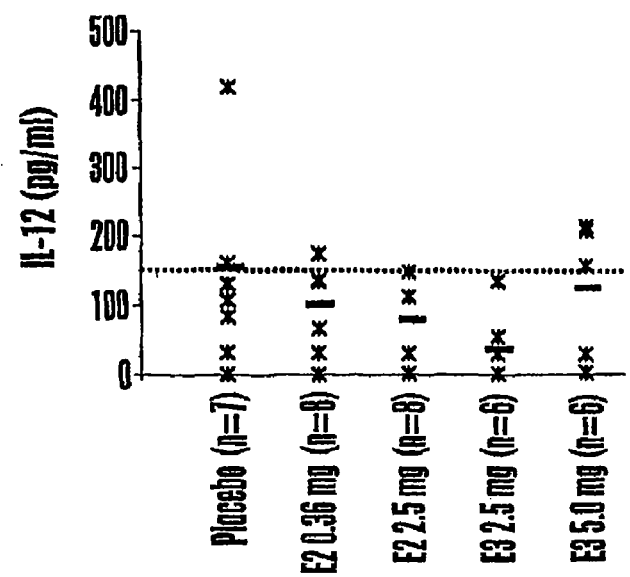

To determine if low dose estrogen therapy altered cytokine secretion patterns, DLN cells were prepared from individual mice at the peak of clinical EAE and cytokine levels were measured 48-72 hours after in vitro stimulation with PLP 139-151. IFN-γ, IL-12, and TNF-α were used as representative Th1 cytokines while IL-4, and IL-10 were used as representative Th2 cytokines. Even though the secretion of IFN-γ was consistently lower in E2 and E3 treated groups of mice (FIG. 5A), the reduction in IFN-levels fell short of being statistically significant (p>0.10). The decrease in IFN-secretion was accompanied by a modest increase in IL-10 (FIG. 5B) and a small decrease in IL-12 (FIG. 5E). Despite the lack of statistical significance, the trend towards higher Th1 and lower Th2 cytokines points towards a subtle shift in the Th1/Th2 balance. The shift can be seen more clearly when the cytokine response of each individual mouse is plotted as a ratio of IFN-γ to IL-10 (FIG. 5C). There was a marked decrease in the frequency of high Th1 responder mice in the E2 and E3 treated groups when compared to placebo animals that approached significance (p=0.09 for the 5.0 mg E3 treated mice). Additionally, no informative trends were detected in IL-4 secretion (FIG. 5D), and TNF-α secretion was very often below the limits of detection for the assay (<31.25 pg/ml). Modest changes in cytokine responses induced by low dose estrogen therapy were also observed in the B10.PL model and were consistent with the data described for the SJL model.

Figure 6:
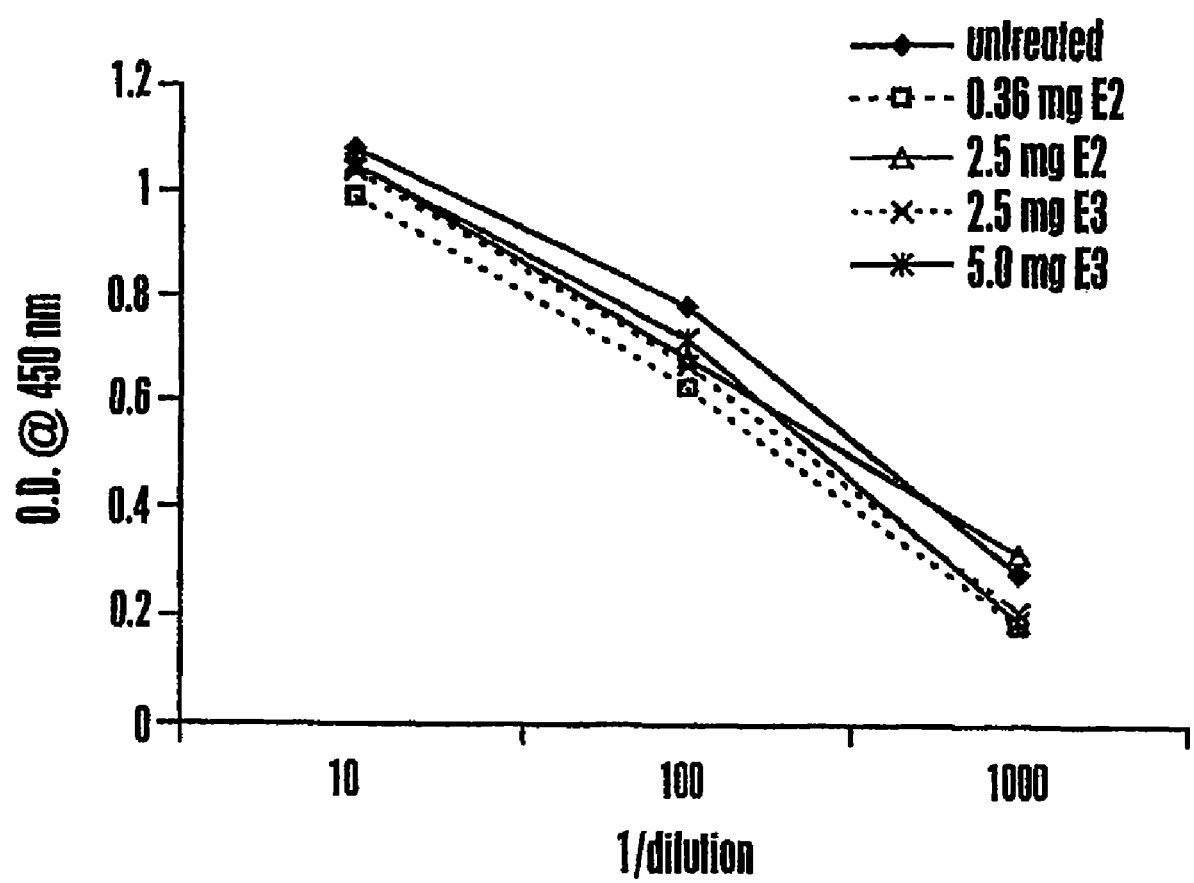
FIG. 6 shows the effect of estrogen therapy on PLP 139-151 specific immunoglobulin production in female SJL mice with EAE.

The humoral immune response in low dose estrogen treated animals was compared to placebo controls. Serum was collected from individual mice at the peak of clinical disease and PLP 139-151 specific immunoglobulin levels were measured using a standard ELISA assay. No significant difference (p>/=0.180) in PLP 139-151 specific antibody production was observed between placebo and estrogen treated groups (FIG. 6). These data suggest that the modest shift towards Th2 cytokine production in estrogen treated mice was insufficient to enhance humoral immunity.

EXAMPLE II

Effect of the Combination of Low-Dose Estrogen and Immunotherapy on an Immune Pathology This example shows that the combination of vaccination with a BV8S2 (Vβ8.2) peptide and low-dose estrogen therapy resulted in full protection against disease in an animal model of multiple sclerosis, whereas only partial protection was observed with either therapy alone. Additionally, the combined effects of immunotherapy and low-dose estrogen therapy potentiated IL-10 production by regulatory T cells, and synergistically enhanced IL-10 and TGF production by antigen-specific T cells. Thus, low dose estrogen therapy is an effective method of enhancing the efficacy of immunotherapeutic agents in reducing the severity of immune pathologies in humans.

Materials and Methods

Animals. Tg mice bearing the functionally rearranged BV8S2 gene specific for MBP-NAcl-11 on the B10.PL background were provided by Dr. Joan Goverman (Seattle, Wash.). Male Tg mice were bred with B10.PL females, and the offspring tested for expression of the transgene by FACS analysis of blood cells stained for BV8S2 (Vβ8.2) as described in Goverman et al., Cell 72:551-560 (1993). Approximately half of each litter expressed the BV8S2 transgene, with approximately half of these transgenic littermates of each sex. For some experiments, mice expressing the BVBS2 transgene were compared to litter mates that did not express the transgene. The colony was housed and cared for at the Animal Resource Facility (Portland VAMC) according to institutional guidelines.

Antigens. N-acetylated MBP-1-11 peptide (Ac-ASQKRPSQRSK) (SEQ ID NO:75) was synthesized using solid phase techniques and was purified by high performance liquid chromatography (HPLC) at the Beckman Institute, Stanford University (Stanford, Calif.). Glutathione S-transferase (GST) and GST-BV8S2 proteins were expressed and purified as described in Vaniene et al., J. Neurosci. Res. 45:475-486 (1996). The GST-BV8S2 fusion protein contains the complete BV, BD, and BJ regions and the first 19 residues of the BC region from the TCR of an encephalitogenic rat T cell clone fused to the C-terminal end of GST. To control for the GST-BV8S2 protein, the GST protein was produced and purified using the same expression system. The GST protein was included as a control in all tissue culture experiments utilizing the GST-BV8S2 protein.

Induction of active EAE and protection with BV8S2 protein. EAE was induced in Tg male or female mice by injecting 400 g MBP-Acl-11/CFA containing 200 g *Mycobacterium tuberculosis* s.c. over four sites on the flank. For TCR protection experiments, mice were injected with 12.5 µg recombinant rat BVBS2 protein/IFA (experimental) or saline/IFA or GST/IFA (sham controls) intraperitoneally (i.p.) on days −7 and +3 relative to injection of the MBP-NAcl-11, according to the protocol described in Kumar et al., J. Exp. Med. 178: 909-916 (1993). In an alternative protocol, mice were given the initial two injections and then boosted weekly with 12.5 µg BVBS2 protein or saline given s.c. Groups of male and female mice that were treated with TCR protein (FIG. 7) were litter mates.

Estrogen therapy. For estrogen hormone therapy or combined estrogen plus TCR therapy, 3 mm pellets containing varying amounts of 17β-estradiol or estriol (Innovative Research of America, Sarasota, Fla.) were implanted subcutaneously on the animal's back seven days prior to induction of EAE. Control mice were sham operated but received no pellet. The estrogen pellets provide continuous controlled release of a constant level of hormone over a period of 60 days. The concentration of 17β-estradiol in pellets used in these experiments and the expected serum concentration of secreted hormone maintained in the mice are listed in Table 11, along with the established range of physiological serum hormone levels during the estrus cycle and pregnancy. Serum concentrations of estrogen monitored prior to and during the course of EAE in representative control and implanted mice consistently fell within the expected ranges.

TABLE 11

| Pellet (mg) | 17β-estradiol (pg/ml) | Physiological Equivalent |
|---|---|---|
| 15 | 9,000-10,000 | Pregnancy (5,000-10,000 pg/ml) |
| 5 | 3,000-4,000 | |
| 2.5 | 1,500-2,000 | |
| 1.5 | 800-1,000 | |
| 0.36 | 150-200 | Estrus (100-200 pg/ml) |
| 0.10 | 25-50 | Diestrus (20-30 pg/ml) |
| 0.025 | 5-10 | |

Disease assessment. Mice were assessed daily for clinical signs of EAE according to the 7-point scale described in Example I. The cumulative disease index (CDI) was determined for each mouse by summing the daily clinical scores, and the mean CDI±SEM was calculated for the control and experimental groups. The mean clinical score (MCS) was calculated for each mouse by dividing the CDI by the duration (days) of disease, and the mean±SEM calculated for the control and experimental groups.

Proliferation assay. Spleens (SPL) were removed surgically, and single cell suspensions were prepared. Proliferative responses of T cells were determined in 96-well microtiter plates by incubating 4×10⁵ spleen cells plus antigen at an optimal concentration of 20 μg/well. Cultures were incubated for 72 hr at 37° C. and 7% CO, the last 18 hr in the presence of 0.5 μCi ³H-thymidine. Cells were harvested onto glass fiber filters, and thymidine uptake was determined by liquid scintillation. Mean cpm±SEM were calculated from triplicate wells. The stimulation index (SI) was obtained by dividing cpm from antigen-stimulated wells by cpm from wells with no antigen. SI in cultures stimulated with GST alone was subtracted from the SI induced with GST-BV8S2 protein.

Figures 7A, 7B, 7C, 7D:
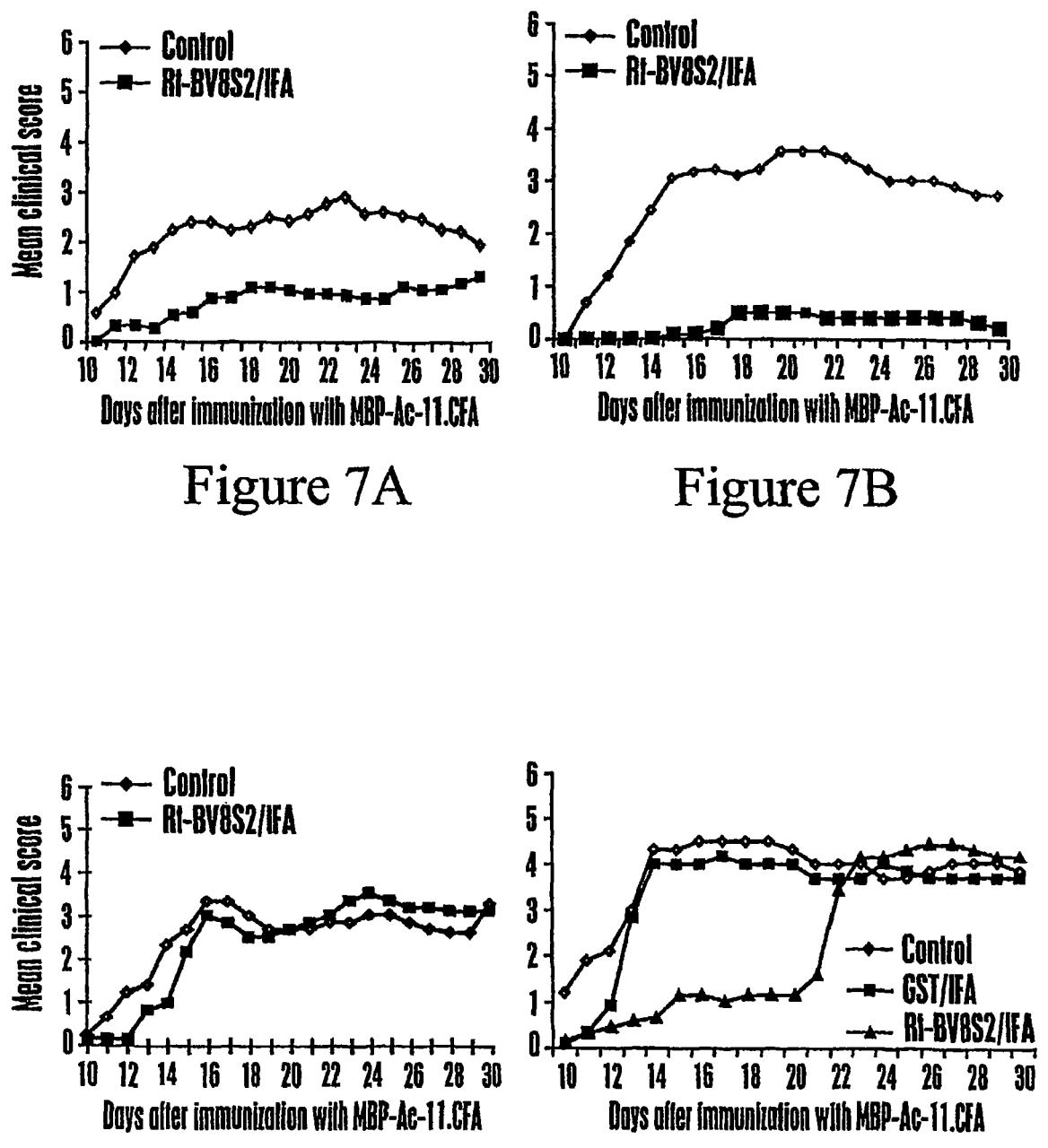

Measurement of cytokine secretion. Spleen cells were suspended at 4×10⁶ cells/ml in stimulation medium with and without specific antigens. Cell culture supernatants were recovered at 72 hr and frozen at −70° C. until needed for the cytokine assay. Measurement of cytokines was performed by ELISA (Bebo et al., supra (1998)) using cytokine specific capture and detection antibodies (PharMingen, San Diego, DA). Capture antibodies for IFN-γ, IL-10, and TGF-β were diluted to 2 μg/ml in bicarbonate coating buffer (0.1M NaHCO₃, pH 8.2). Standard curves for each assay were generated using recombinant mouse cytokines (PharMingen), Results Gender difference in treatment of EAE with BV8S2 protein. Responses to vaccination with BV8S2 protein were compared in male versus female Tg mouse littermates, using two different protocols. As is shown in FIG. 7A and quantified in Table 12, males injected i.p. with BV8S2 protein/IFA on days −7 and +3 relative to EAE induction were significantly protected from EAE, with lower incidence and cumulative disease scores (CDI) than sham treated males. In contrast, females vaccinated using the same protocol were not protected from EAE (FIG. 7C and Table 12). As illustrated in FIGS. 7B and 7E, the protective effect in males could be enhanced by boosting weekly with additional s.c. injections of BV8S2 protein. These boosting injections had an early effect on littermate females as well, producing a significant delay in onset of clinical disease (FIG. 7D and Table 12). However, this temporary suppression of clinical disease was lost abruptly (FIG. 7D), and there was no significant amelioration of subsequent disease assessed during days 18-30 (Table 12).

TABLE 12

| Group | Figure | Treatment Group | Incidence | Day of Onset | CDI | |
|---|---|---|---|---|---|---|
| Males | 1A | Controls | 13/16 | 15 ± 1 | 49 ± 10 | |
|  |  | BV8S2 | 6/16* | 14 ± 1 | 17 ± 7* | |
| Males | 1B | Controls | 10/10 | 13 ± 1 | 63 ± 9 | |
|  |  | BV8S2, B | 1/9*** | 15 | 7 ± 7*** | |
| Females | 1C | Controls | 5/5 | 15 ± 4 | 75 ± 12 | |
|  |  | BV8S2 | 6/6 | 13 ± 1 | 82 ± 23 | |
|  |  |  |  |  | Day 1-21 | Day 22-30 |
| Females | 1D | Controls | 6/6 | 11 ± 1 | 43 ± 5 | 35 ± 5 |
|  |  | GST | 6/6 | 12 ± 1 | 36 ± 4 | 34 ± 3 |
|  |  | BV8S2, B | 7/7 | 19 ± 5 | 10 ± 7 | 37 ± 3 | and the concentration of cytokines in the cell supernatants was determined by interpolation from the appropriate standard curve.

Assessment of antibody responses. Antibody reactivity to MBP-Acl-11 peptide and GST-BV8S2 protein was determined by indirect ELISA as described in Hashim et al., *J. Immunol.* 144:4621-4627 (1990). Briefly, mouse antisera from treated and control Tg mice with EAE were incubated in antigen coated wells, and bound antibody was detected spectrophotometrically with peroxidase-labeled rabbit anti-mouse antibody and o-phenylene-diamine as a substrate. Differences between groups were determined using Student's t-test.

Ovariectomy. The ovaries were removed by making two bilateral incisions (5 mm) halfway between the base of the tail and the middle of the back, followed by small incisions (2.5 mm) through the peritoneal wall. The ovaries were pulled through the incisions by grasping the periovarian fat, the blood vessels ligated, and the ovaries removed. The incision was closed by surgical skin clips. The animals were allowed to recover for at least 1 week before initiation of experiments.

Androgen and estrogen detection. Mice were bled by cardiac puncture and the blood was allowed to clot at 4° C. overnight. The samples were centrifuged, and the sera collected and stored at −80° C. until hormone analysis was performed. Serum levels of estrogen were determined by radioimmunoassay (RIA) after Sephadex LH-20 column chromatography, as described in Roselli et al., *Endocrine* 64:139 (1996). All samples were analyzed in a single assay.

Figure 8A:
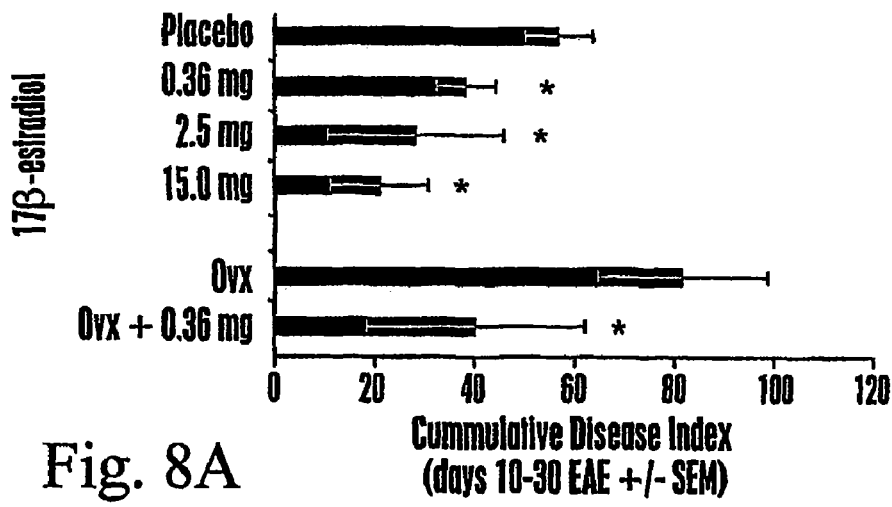
FIG. 8 shows the effect of 17β-estradiol and estriol on cumulative EAE disease index in intact and ovariectomized female mice.

Effects of estrogen on EAE. The effects of sex hormones, including 17β-estradiol and estriol, were evaluated on the clinical course of EAE by hormone depletion or addition experiments. As shown in FIG. 8A, female Tg mice unable to produce detectable levels of estrogen (<1 pg/ml) or other sex hormones after ovariectomy developed significantly more severe EAE than sham ovariectomized females (CDI=81 versus 56, p<0.001). These data demonstrate that even basal levels of ovarian factors, possibly including estrogen, provide some regulation of EAE.

Figure 8B:
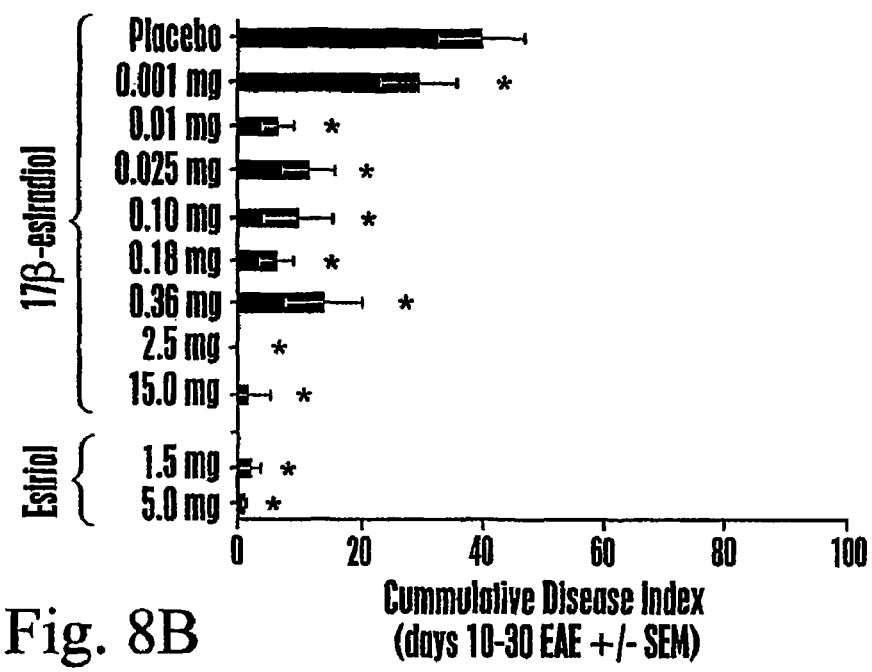

Treatment of sham or non-ovariectomized females with 17β-estradiol pellets produced a dose-dependent inhibition of EAE in both Tg females (FIG. 8A) and B10.PL littermate females (FIG. 8B). Notably, added estrogen had a less pronounced effect on the Tg versus non-Tg females. In B10.PL females, essentially complete inhibition of EAE was produced with 15 mg pellets secreting pregnancy levels of 17β-estradiol (9,000-10,000 pg/ml serum) over a 60 day period or with 2.5 mg pellets (1,500-2,000 pg/ml serum), and substantial inhibition was produced over a wide range of estrogen concentrations from estrus (0.36 mg pellets secreting 150-200 pg/ml serum) to diestrus levels (0.10 mg pellets secreting 25-50 pg/ml serum, FIG. 8B). By comparison, in Tg females, pregnancy levels of hormone (15 mg pellets) produced a marked but incomplete inhibition of EAE, with estrus levels (0.36 mg pellets) producing only moderate inhibition (FIG. 8A).

Estriol, which is normally elevated only during pregnancy, had an equivalent inhibitory effect on EAE in B10.PL females as 17β-estradiol (FIG. 9B). The partial resistance to estrogen therapy in Tg females may be due to the higher native frequency of Acl-11 specific T cells afforded by the transgene (Offner et al. supra (1998)) that likely accounts for an increased severity of EAE (CDI=56 in Tg vs 39 in non-Tg females, p<0.001. Consistent with this notion, estrogen treatment of ovariectomized female Tg mice reduced the severity of EAE to about the same level as sham ovariectomized Tg mice treated with estrogen (FIG. 8A). However, the inability of estrogen to fully inhibit EAE in Tg females at very high levels approximating pregnancy suggests that a portion of the encephalitogenic cascade is estrogen insensitive.

Figure 9:
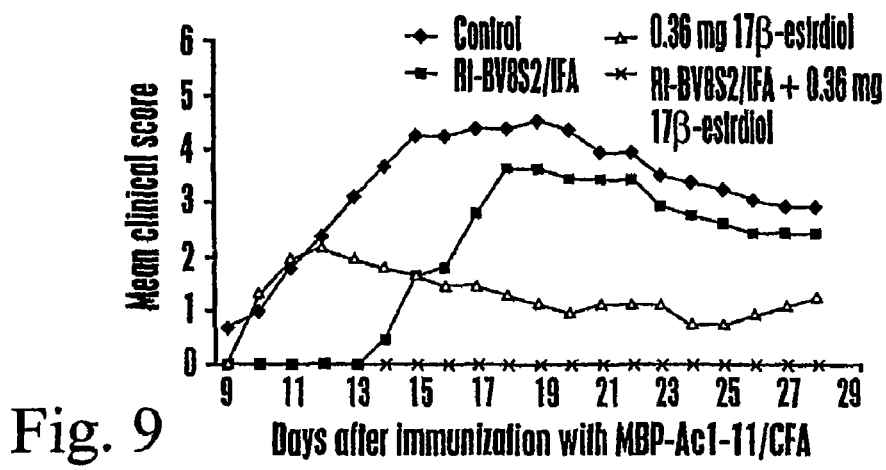
FIG. 9 shows the effect of administration of BV8S2 protein, 17β-estradiol and the combination of BV8S2 vaccination plus estrus levels of 17β-estradiol on EAE in Tg females.
Figure 10A:
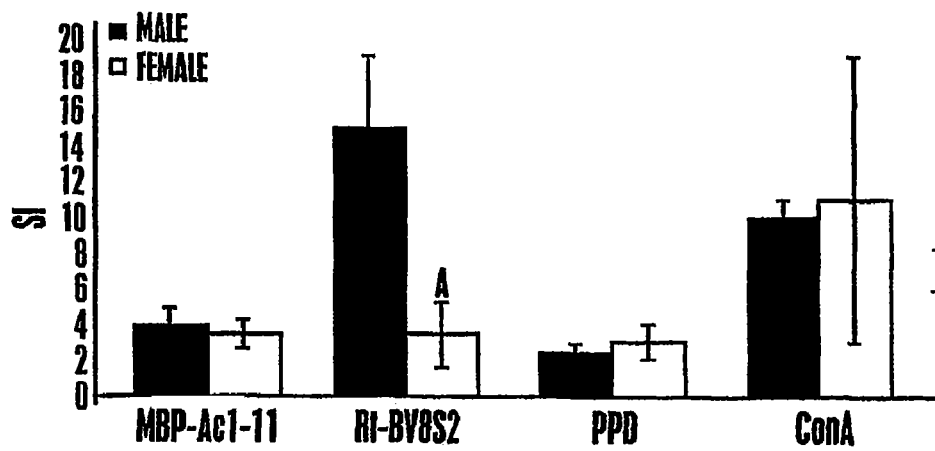
FIG. 10 shows T cell proliferative (A-C) and antibody (D) responses in BVBS2 and/or E2 treated and control Tg mice challenged to develop EAE.
Figure 10B:
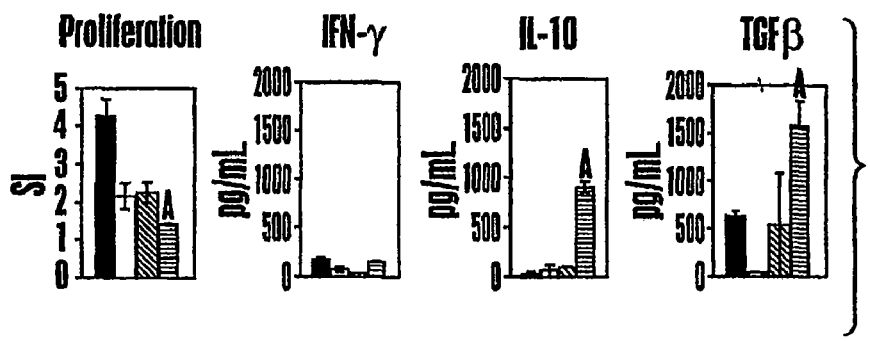

Combined TCR and estrogen therapy. Because TCR and estrogen therapy were both partially effective for preventing EAE in Tg females, the effects of single versus combined therapy were directly compared. Consistent with the results described above, Tg females vaccinated with BV8S2 protein (with weekly boosting) had delayed onset but eventually developed severe EAE, whereas mice treated with estrus levels of E2 (0.36 mg pellets secreting 150-200 pg/ml serum over 60 days) had normal onset but generally less severe disease (FIG. 9). However, combined treatment with both TCR protein and estrus levels of E2 produced almost complete protection against EAE (FIG. 9), with only 3 of 16 mice developing very mild disease (Table 13). A similar degree of protection was provided in ovariectomized Tg females treated with BV8S2 protein and estrogen (Table 13), demonstrating that the enhanced therapeutic effect was dependent on E2 rather than a combination of estrogen and other gonadally produced sex hormones.

observed previously (Offner et al. supra (1998)). Treatment with either BV8S2 protein or estrogen alone reduced proliferation and marginally affected cytokine responses to Acl-11. However, combined treatment with both BVBS2 protein and estrogen markedly reduced proliferation and dramatically enhanced production of IL-10 and TGF-β, but not IFN-γ in response to Acl-11 peptide (FIG. 10B).

Figure 10C:
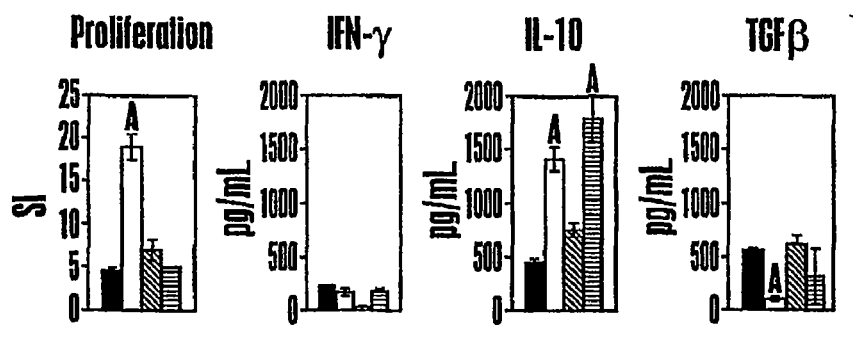
Figure 10D:
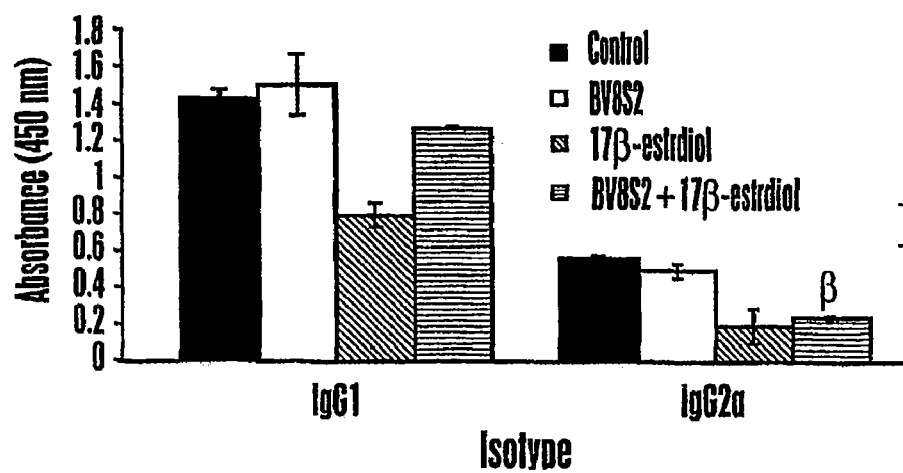

In contrast, splenic proliferation and IL-10 responses to BV8S2 protein were enhanced by both treatments individually, and further potentiated with combination therapy, with no significant effects of treatment on IFN- and TGF-secretion (FIG. 10C). Additionally, combination therapy reduced circulating levels of Acl-11 specific IgG2a antibody associated with Th1 response, with no effect on IgG1 response (FIG. 10D).

EXAMPLE III

17β-Estradiol Inhibits Chemokines and Receptors in EAE

This example shows that the protective effect of low dose estrogen on animals with a Th1 immune pathology is mediated, in part, by inhibition of mRNA expression of chemokines, chemokine receptors, and inflammatory cytokines by recruited inflammatory T cells.

Materials and Methods

Mice. Transgenic mice were obtained, bred and housed essentially as described in Example II. Mice were used at 8-12 weeks of age.

TABLE 13

| Total | Incidence | Onset | Peak | Mortality | Average CDI (10-30) |
|---|---|---|---|---|---|
| Control | 60/64 | 11.8 ± 1.1 | 4.7 ± 0.1 | 12/49 | 56.4 ± 7.0 |
| BV8S2 | 45/49 | 17.4 ± 2.2[A] | 3.9 ± 1.1[A] | 1/49 | 32.0 ± 13.2[A] |
| 17β-estradiol | 25/33 | 15.1 ± 2.1[A] | 3.6 ± 0.7[A] | 1/33 | 37.3 ± 6.2[A] |
| BV8S2-17β-estradiol | 3/16 | 18.8 ± 8.0[A] | 0.5 ± 0.4[A] | 1/16 | 3.1 ± 4.0[A] |
| Ovx | 27/27 | 10.6 ± 0.9 | 5.3 ± 0.7 | 7/27 | 81.2 ± 17.3[A,C] |
| BV8S2 | 23/26 | 18.0 ± 1.9 | 3.9 ± 1.3 | 4/26 | 40.1 ± 20.9[B] |
| 17β-estradiol | 11/15 | 13.6 ± 1.5 | 3.5 ± 0.8 | 4/15 | 40.0 ± 22.1[B] |
| BV8S2 + 17β-estradiol | 3/16 | 20.8 ± 6.0 | 0.9 ± 0.9 | 0/16 | 7.4 ± 6.7[A,B] |

Data are combined from a total of 10 separate experiments.
[A]Significant difference between control and experimental (P < 0.0001).
[B]Significant difference between Ovx control and Ovx experimental (P < 0.0001).
[C]Significant difference between Ovx and non-Ovx control (P < 0.001).
Ovx, ovarectomized.

Estrogen skews response to Acl-11 and potentiates response to BV8S2 protein. To investigate the mechanism(s) involved with individual and combined therapies, proliferation and cytokine responses of immune T cells from naive and treated mice were evaluated. As shown in FIG. 10A, BV8S2 naive Tg males and females had equivalent proliferation responses to Acl-11 peptide, PPD, and ConA, but naive Tg females had a strikingly reduced reactivity to the BVBS2 protein. This finding suggests that Tg females have a diminished native capacity to regulate an encephalitogenic response.

During development of EAE, splenic T cell responses to Acl-11 peptide were characterized by moderate proliferation and production of TGF-β, and essentially absent secretion of IL-10 (FIG. 10B). Secretion of IFN-γ in response to Acl-11 peptide was modest, reflecting preferential migration of inflammatory T cells to draining lymph nodes and the CNS as Induction of active EAE. EAE was induced, and disease assessed, essentially as described in Example II. Disease onset was defined as the first day of clinical signs, peak—acute phase of EAE—as maximum severity of clinical signs (day 16-17 after immunization with encephalitogenic peptide) and recovery as day 28 post-immunization, when clinical severity of EAE was diminished. The cumulative disease index (CDI) was determined for each mouse by summing the daily clinical scores. Mice selected from control, ovariectomized, and 17β-estradiol treated groups were sacrificed and spinal cords were isolated by insufflation and frozen at −70 C or mononuclear cells were isolated over a Percoll step gradient and counted as described in Offner et al., J. Immunol. 161:2178-2186 (1998). Lymph nodes (LN) or spleens (SPL) were removed surgically and passed through a wire mesh screen to obtain a single-cell suspension. Frozen spinal cords were subsequently thawed and evaluated for expression of chemokines, chemokine receptors and cytokines by the RNase protection assay.

17β-estradiol treatment. For 17β-estradiol hormone therapy, 3-mm pellets containing 0.36 mg of 17β-estradiol (Innovative Research of America, Sarasota, Fla.), expected to provide physiological equivalence of the estrus cycle (150-200 pg/ml in serum) over 60 days, were implanted s.c. on the animal's back 7 days before induction of EAE. Control mice were sham operated and implanted with a pellet containing saline (which did not affect the course of EAE) or no pellet. The 17β-estradiol pellets provide continuous controlled release of a constant level of hormone over a period of 60 days. Serum concentrations of 17β-estradiol were evaluated in representative mice from each group. Sham treated mice had variable levels of 17β-estradiol that reflected both estrus and diestrus mice (ranging from about 20 to 200 pg/ml, on average about 50 pg/ml). In contrast, OVX mice did not have any detectable estradiol (<1 pg/ml). E2-treated intact mice were also variable (about 200-400 pg/ml), reflecting the combination of native estrus/diestrus levels plus the exogenous estradiol from the pellet, whereas the E2-treated OVX mice were somewhat lower (about 150-200 pg/ml).

RNase protection assay. Total RNA was extracted from frozen spinal cords or lymph node cells using the STAT-60 reagent (Tel-Test, Inc., Friendswood, Tex.). Chemokine expression was determined by using the RiboQuant RPA kit (PharMingen) according to the manufacturer's instructions. A multiprobe set detected the following chemokine transcripts: C-X-C chemokines: MIP-2 and IP-10; C-C chemokines: RANTES, MIP-1α, MCP-1, and TCA-3; and C chemokine: Ltn. The chemokine receptor set detected the following transcripts: CCR1, CCR1b, CCR2, CCR3, CCR4, CCR5. Using RPA multiprobe it was possible to detect the following cytokines: IL-4, IL-10, TNF-α, LTβ, IFN-γ. The sample loading was normalized by the housekeeping gene, L32, included in each template set. RPA analysis was performed on 10 μg total RNA hybridized with probes labeled with [$^{32}$P]UTP. After digestion of ssRNA, the RNA pellet was solubilized and resolved on a 5% sequencing gel. Controls included the probe set hybridized to transfer RNA only, appropriate control RNA which serves as integrity control for the RNA sample, and yeast tRNA as a background control. For quantification, gels were exposed by phosphorimaging (Bio-Rad Laboratories, Hercules, Calif.) and radioactivity in individual bands (after background subtraction) in comparison with L32 was assessed with Quantity One software (Bio-Rad Laboratories, Hercules, Calif.)

Proliferation assay. Proliferation responses of splenic T cells were determined essentially as described in Example II, except that antigen was used at an optimal concentration of 50 μg/ml.

Flow cytometry. Lymph node cells from sham and 17β-estradiol treated animals with EAE were washed with PBS/2% FCS/0.2% NaN$_3$ and first incubated on ice for 30 min with Fcγ III/II receptor blocking monoclonal antibody (PharMingen), then stained with PE-conjugated anti-CD3 (PharMingen). After 20 min of incubation with anti-CD3, the cells were fixed and permeabilized using Cytofix/Cytoperm (PharMingen). Subsequently, cells were incubated with anti-CCR1, anti-CCR2, anti-CCR3, anti-CCR4 and anti-CCR5 goat anti-mouse polyclonal antibodies (Santa Cruz Biotechnology Inc.; USA) for 30 min on ice. After washing, cells were stained with FITC-conjugated anti-goat monoclonal antibodies (Sigma) for an additional 30 min on ice. Cells were analyzed using a FACS-Scan (Becton Dickinson). Propidium iodide and forward/side scatter gating were used to exclude dead cells.

Measurement of cytokine secretion. Lymph nodes of naïve BV8S2 TCR transgenic females were suspended at 4×10$^6$ cells/ml in stimulation medium with antigen and with or without 2000 pg/ml of 17β-estradiol. Cell culture supernatants were recovered at 72 hours and frozen at −70 C until used. Measurement of cytokines was performed by ELISA essentially as described in Example II.

Ovariectomxy. Ovariectomy was performed essentially as described in Example II.

Statistics. Non-parametric clinical EAE data (peak disease scores and cumulative disease index) were evaluated between groups using the Mann-Whitney test; the day of onset among the various groups was evaluated using the t-test or ANOVA; the incidence and mortality rates were compared using the 2 test (Fisher's exact test in some instances). Comparison of RPA values, cytokine values, and CPMs were evaluated by the t-test or ANOVA. The accepted level of significance was p<0.05.

Results

Figure 11A:
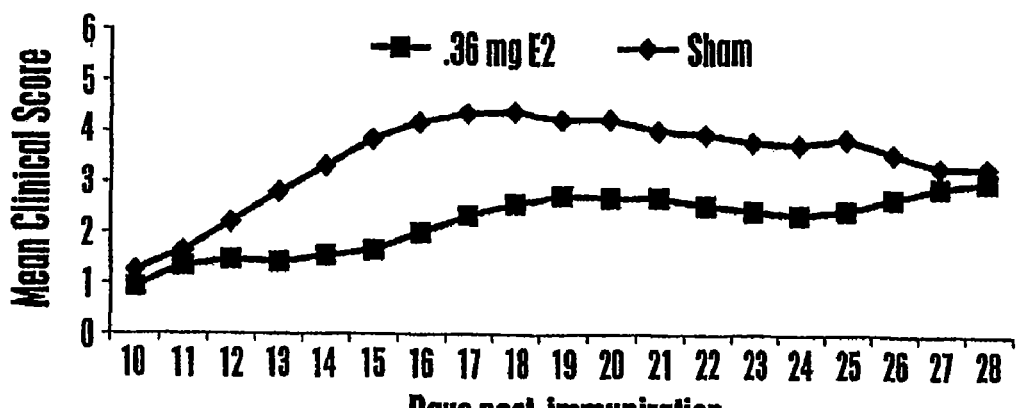
FIG. 11 shows the effect of ovariectomy (OVX) and treatment with estrus levels of 17β-estradiol (E2) on the course of EAE in Tg female mice.
Figure 11B:
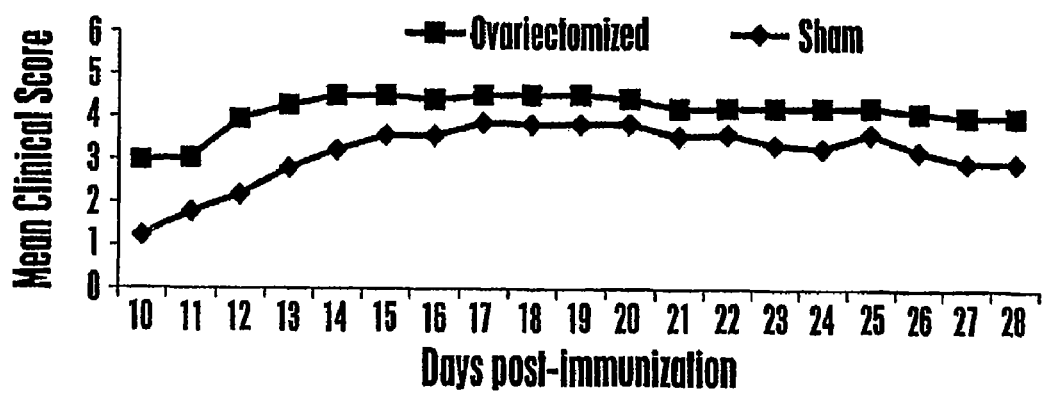

Effects of 17β-estradiol on EAE. 17β-estradiol (E2) or estriol released from implanted pellets was shown in Example I to partially inhibit EAE in a dose dependent manner in BVBS2 transgenic mice. Clinical EAE data for groups of these mice used in the current study are graphed in FIG. 11 and summarized in Table 14. Mice implanted with 0.36 mg pellets of 17β-estradiol, which in combination with native hormone (20-200 pg/ml in sham mice) provided 150-400 pg/ml E2 in serum (estrus levels), developed significantly later onset and less severe EAE (lower peak score and CDI) than sham operated control mice (FIG. 11A and Table 14). In addition to reducing disease severity, 17β-estradiol treatment inhibited proliferation of MBP-Acl-11 specific T cells by an average of about 47%, and prevented infiltration of mononuclear cells into spinal cords by approximately 60% (Table 15).

Figure 11C:
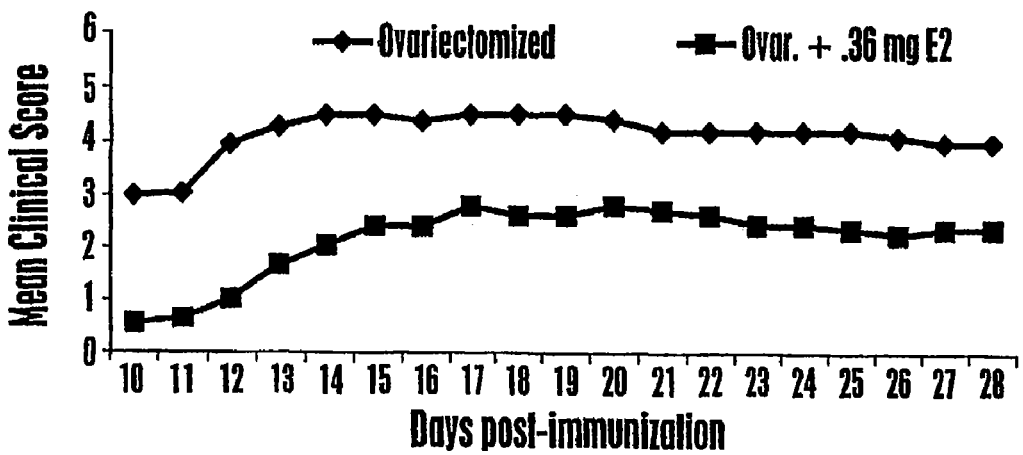

In contrast, ovariectomized mice, in which endogenous 17β-estradiol was not detectable (<1 pg/ml), developed significantly earlier onset and more severe signs of EAE than sham operated mice (FIG. 11B and Table 14). 17β-estradiol treatment of ovariectomized mice with implanted 0.36 mg pellets provided about 100-200 pg/ml E2 in serum, and inhibited EAE to approximately the same degree as E2-treated non-ovariectomized mice (FIG. 11C and Table 14).

TABLE 14

| Group of mice | Incidence | Onset | Peak | CDI |
|---|---|---|---|---|
| Sham | 19/19 | 11.4 ± 0.5 | 4.3 ± 0.3 | 64.9 ± 4.7 |
| 17β-estradiol treated | 15/18 | 17.4 ± 1.8* | 2.5 ± 0.5** | 40.4 ± 7.1** |
| Sham | 12/12 | 11.3 ± 0.7 | 3.8 ± 0.5 | 59.4 ± 4.9 |
| OVX | 12/12 | 9.8 ± 0.6* | 4.8 ± 0.4* | 85.3 ± 7.3** |
| OVX | 12/12 | 9.8 ± 0.6 | 4.8 ± 0.4 | 85.3 ± 7.3 |
| OVX + 17β-estradiol$^a$ | 8/11 | 16.5 ± 2.3** | 2.6 ± 0.6** | 40.0 ± 8.5** |

*p < 0.05
**p < 0.01
$^a$EAE severity also significantly less than in Sham group

TABLE 15

| Group of mice | Mean clinical score* | Number of cells/cord |
|---|---|---|
| Sham | 2.4 | 27000 |
| 17β-estradiol treated | 1.3 | 10000 |

*mean clinical score at time of cord removal

17β-estradiol treatment results in downregulation of chemokine mRNA expression in spinal cords. To optimize detection of clinically-related changes, chemokine expression was compared in 17β-estradiol protected versus sham pellet implanted mice during the peak acute phase of disease (16-17 days after immunization with MBP-Acl-11 peptide/CFA) and during the chronic phase (28 days after immunization). At the earlier time point, spinal cord (SC) tissue was sampled from sham-treated mice exhibiting paralytic EAE (scores of 4-5) and compared to SC tissue from 17β-estradiol treated mice which had not yet developed any clinical signs (EAE scores of 0). A quantitative method—the RNase protection assay—was employed to examine RNA synthesis for the following chemokines: RANTES, MIP-1α, MCP-1, and TCA-3 (C-C-subfamily); and MIP-2 and IP-10 (C-X-C-subfamily). The tissue sample for RPA was prepared by homogenization of whole spinal cord and total cellular RNA was extracted.

Figure 12:
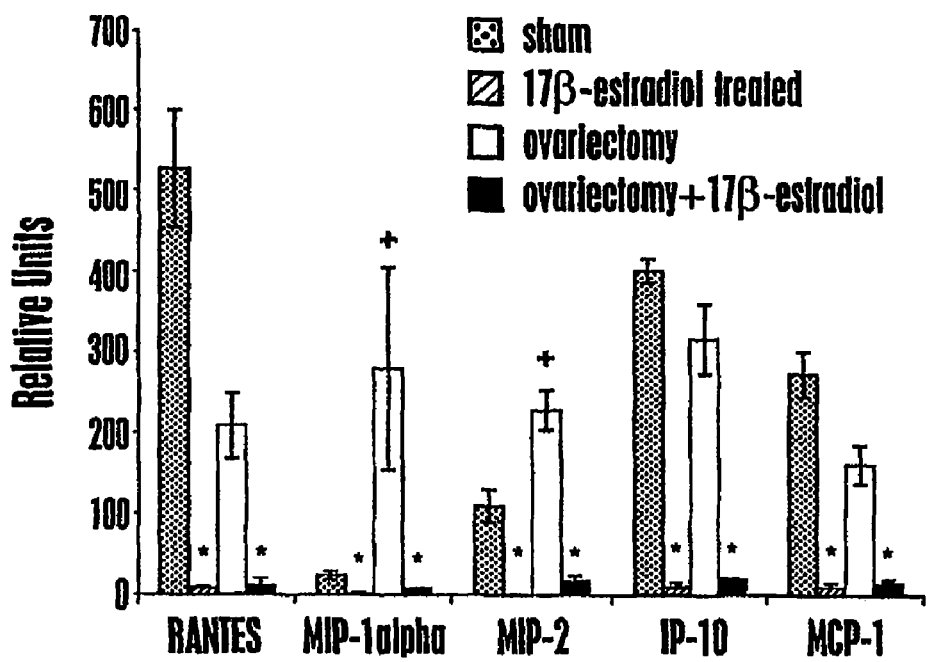
FIG. 12 shows data obtained from RPA analysis of chemokine mRNA expression in spinal cords of intact and ovariectomized 17β-estradiol treated and control TCR BV8S2 transgenic female mice.

As quantified in FIG. 12, transcripts for RANTES, MIP-1α, MIP-2, IP-10 and MCP-1, but not TCA-3 were detected in SC from Tg females at the peak and chronic phases of disease. Paraplegic mice (sham group) had abundant RNA expression of RANTES, IP-10, and MCP-1, with lesser mRNA levels of MIP-1α and MIP-2 (FIG. 12). 17β-estradiol protected mice had profoundly lower levels of mRNA expression of all detectable chemokines. At the peak of disease, the difference between groups reached p<0.001 (FIG. 12). Differences in chemokine expression between sham and E2-treated groups were still present but less pronounced during the chronic phase of EAE, reflecting the clinical status of the donors (sham, EAE scores of 3; E2, EAE scores of 0-1).

Ovariectomy increases mRNA expression of MIP-1α and MIP-2. Ovariectomy resulted in loss of detectable 17β-estradiol, as well as other ovarian hormones, and significantly enhanced the clinical severity of EAE (FIG. 11A and Table 14), implicating basal levels of these factors in natural regulation. To evaluate effects of hormone depletion on chemokine levels during EAE, an RPA analysis was carried out of SC from ovariectomized female mice on day 16 after induction of EAE. SC were sampled from sham-treated mice with EAE scores of 4-5, and from ovariectomized mice with EAE scores of 5-6). Surprisingly, ovariectomized mice that displayed the most severe signs of EAE had lower mRNA levels than sham treated mice of the normally predominant chemokines RANTES, IP-10 and MCP-1, but significantly enhanced expression of MIP-1α and MIP-2 (FIG. 12). 17β-estradiol treatment of ovariectomized females (that inhibited EAE to a comparable degree as E2-treatment of intact mice), strongly inhibited expression of all detectable chemokines (FIG. 12), again reflective of the sampling of SC from mice that had not yet developed overt clinical disease (EAE scores of 0). These results demonstrate the capacity of supplemental 17β-estradiol to profoundly inhibit chemokine expression, and implicate ovarian factors, including 17β-estradiol, as natural regulators of MIP-1α and MIP-2.

Figure 13:
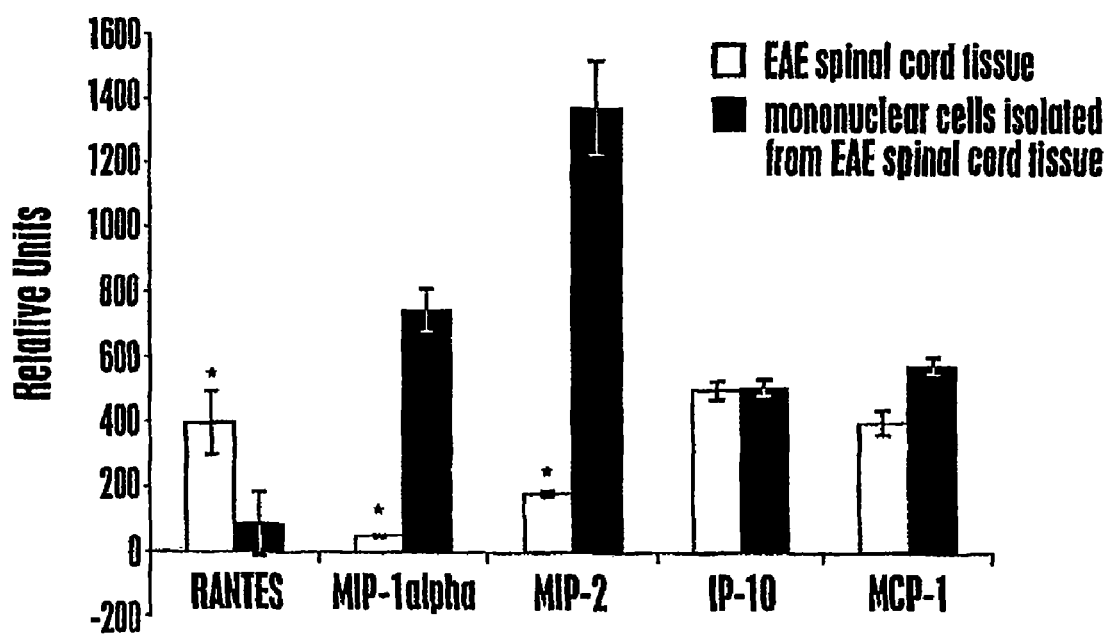
FIG. 13 shows data obtained from RPA analysis of chemokine expression in spinal cord (SC) tissue and mononuclear cells from SC of BV8S2 transgenic mice with EAE.

MIP-1α and MIP-2 are produced by infiltrating mononuclear cells in CNS. To discern which chemokines were produced by infiltrating cells within the CNS, expression of chemokines in whole CNS tissue versus isolated CNS mononuclear cells in Sham treated mice at the peak of EAE were compared. As quantified in FIG. 13, message for MIP-1α and MIP-2, but not RANTES, IP-10 and MCP-1, was enriched in the CNS mononuclear cell fraction, whereas message for RANTES was reduced in the mononuclear cell fraction.

Figure 14:
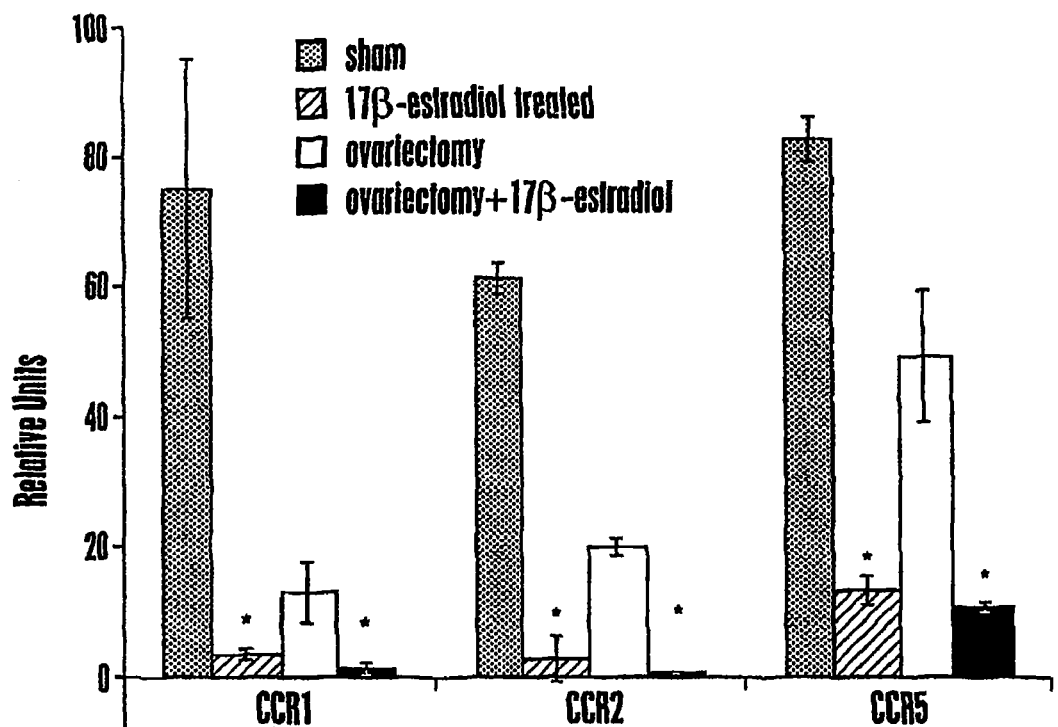
FIG. 14 shows data obtained from RPA analysis of chemokine receptor expression in SC of 17β-estradiol treated, ovariectomized and control TCR BV8S2 transgenic female mice with EAE.

17β-estradiol therapy reduces chemokine receptor mRNA expression in CNS. In addition to chemokines, expression of chemokine receptors in spinal cords of 17β-estradiol treated and control BV8S2 transgenic mice during EAE was assessed. As quantified in FIG. 14, message for CCR1, CCR2 and CCR5 was clearly enhanced in SC samples during both peak and chronic phases of EAE, whereas message for CCR1b, CCR3 and CCR4 was not detectable at either time point. 17β-estradiol treatment that prevented EAE strongly inhibited the elevated mRNA levels for CCR1, CCR2 and CCR5 observed in sham treated mice with EAE (p<0.001). Ovariectomized mice had reduced levels of message for CCR1 and CCR2, with a lesser effect on CCR5 compared to sham-implanted control mice, and supplemental 17β-estradiol treatment again inhibited expression of all of these chemokine receptors (FIG. 14).

Down-regulation of CCR1 and CCR5 in lymphocytes isolated from peripheral lymph nodes of females treated with 17β-estradiol. The reduction of chemokine receptors in of 17β-estradiol treated mice raised the possibility that there might be a systemic effect of 17β-estradiol therapy on chemokine receptor expression by lymphocytes. Thus, chemokine receptors on lymph node cells from 17β-estradiol versus sham treated mice with EAE were quantified using specific antibody staining and FACS analysis. Lymph node CD3+ T cells from 17β-estradiol treated mice had reduced mean channel fluorescence and a significantly lower percentage of positive cells when stained with antibodies to CCR1 (77+2 vs 91+6%, p=0.02) and CCR5 (27+2 vs 35+4, p=0.03) compared to T cells from sham treated mice. No difference was observed in CCR2 staining, and CCR3 and CCR4 were not detectable.

Figure 15:
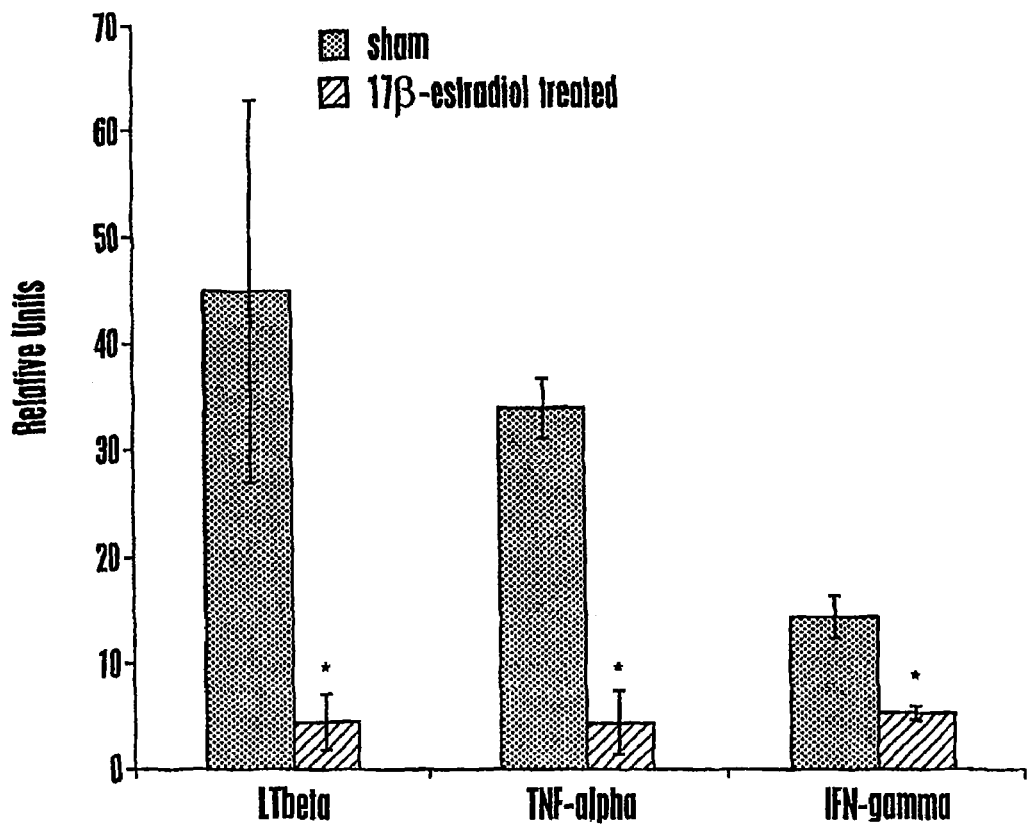
FIG. 15 shows data obtained from RPA analysis of cytokine mRNA expression in SC of 17β-estradiol treated and control TCR BV8S2 transgenic female mice with EAE.

17β-estradiol down-regulates Th1 cytokines but does not cause Th2 cytokine switch. Two possible effects of 17β-estradiol therapy are 1) direct inhibition of inflammatory cytokines or 2) enhancement of Th2 cells and cytokines (Th2 switch) that could locally inhibit Th1 cells. RPA analysis of cytokine message revealed predominant expression of LT-β, TNF-α, and IFN-γ in the of mice at the peak of EAE that was significantly inhibited in 17β-estradiol treated mice (LT-β, p<0.02; TNF-α, p<0.0001; IFN-γ, p<0.01, FIG. 15). In contrast, message for IL-4 and IL-10 was not detectable in SC of mice with EAE, nor were these cytokines induced by 17β-estradiol treatment, indicating no Th2 switch in CNS. No changes in cytokine expression were noted in lymph node cells from E2-treated versus sham control groups.

Figure 16A:
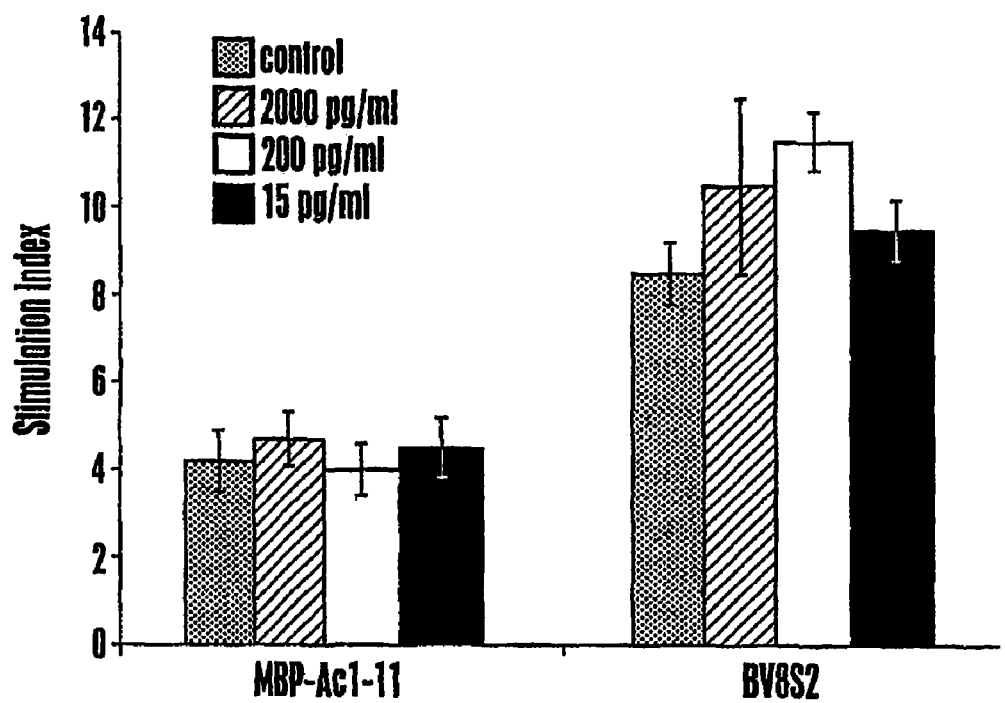
FIG. 16 shows the effect of 17β-estradiol on in vitro proliferative (A) and cytokine (B) responses of lymphokine (LN) T cells from naïve TCR BV8S2 transgenic female mice.
Figure 16B:
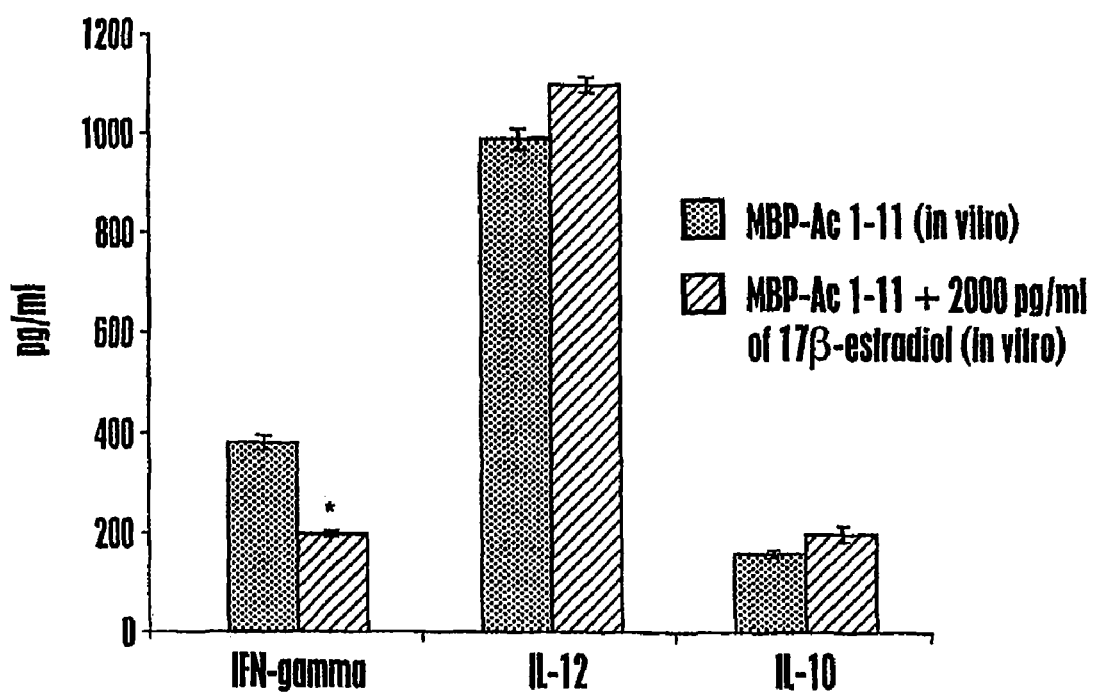

17β-estradiol exerts little effect on T cells cultured in vitro. To evaluate 17β-estradiol effects on antigen specific T cells, splenocytes from naïve BV8S2 single transgenic female mice were stimulated with MBP-Acl-11 peptide or BV8S2 protein in the presence or absence of a range of 17β-estradiol concentrations. As is shown in FIG. 16A, 15-2,000 pg/ml 17β-estradiol had no significant effect on native T cell proliferation response to the encephalitogenic MBP-Acl-11 peptide, and a modest enhancing effect on the native response to the BVBS2 protein. A relatively high dose (2,000 pg/ml) of 17β- estradiol mediated a 50% reduction of secreted IFN-γ protein, with no effects on IL-12 or IL-10 secretion, by MBP-Acl-11 stimulated LN cells from naïve BV8S2 transgenic mice (p<0.005, FIG. 16B). However, lower doses of 17β-estradiol comparable to serum levels in the mice studied above (150-400 pg/ml) had no inhibitory effects on IFN-γ or other cytokine secretion in vitro.

EXAMPLE IV

Low Dose Estrogen Down-Regulates TNFα Production

This example shows that the protective effect of low dose estrogen on animals with a Th1 immune pathology is mediated, in part, by down-regulation of TNF-α secretion at the site of the pathology.

Materials and Methods

Mice. Female C57BL/6, IL-4 KO (B6.129P2-Il4$^{tm1Cgn}$), IL-10 KO (C57BL/6-Il10$^{tm1Cgn}$), and IFN-γ KO (B6.129S7-Ifng$^{tm1Ts}$) mice were obtained from The Jackson Laboratory (Bar Harbor, Me.). The mice were housed in the Animal Resource Facility at the Portland Veterans Affairs Medical Center in accordance with institutional guidelines.

Antigens. Mouse myelin oligodendrocyte glycoprotein (MOG) 35-55 (MEVGWYRSPFSRVVHLYRNGK (SEQ ID NO:76)) was synthesized using solid phase techniques and purified by high performance liquid chromatography (HPLC) at the Beckman Institute, Stanford University (Palo Alto, Calif.).

Estrogen treatment. Sixty-day release pellets containing 2.5 mg of 17β-estradiol (E2) or vehicle were implanted subcutaneously (s.c) in the scapular region behind the neck using a 12-gauge trochar as described by the manufacturer (Innovative Research of America, Sarasota, Fla.). The mice were implanted one week prior to immunization with MOG 35-55. The concentration of E2 expected in the serum is between 1,500-2,000 pg/ml, which is approximately 5 times less than the levels found during pregnancy. E2 levels measured previously as described in Example I were found to be equivalent to those reported by the manufacturer.

Induction of EAE. C57BL/6 and cytokine deficient mice were inoculated s.c in the flanks with 0.2 ml of an emulsion containing 200 μg of MOG 35-55 in saline and an equal volume of complete Freund's Adjuvant (CFA) containing 400 μg of *Mycobacterium tuberculosis* H37RA (Difco Laboratories, Detroit, Mich.). Disease induction required i.v. administration of pertussis toxin on the day of immunization (25 ng/mouse) and 2 days later (67 ng/mouse). The mice were assessed daily for clinical signs of EAE according to the 7 point scale described in Example I.

Histopathology. Histopathologic assessment of spinal column section was performed essentially as described in Example I, except that sections were stained with either luxol fast blue-periodic acid schiff-hematoxylin or silver nitrate prior to analysis.

RNAse protection assay. Chemokine, chemokine receptor and cytokine mRNAs were detected by RPA essentially as described in Example III, except that analysis was performed on 20 μg total RNA.

Proliferation assay. Proliferation assays were performed on draining lymph node (DLN) and spleen (SP) cells essentially as described in Examples I and II, using MOG 35-55 as the test antigen.

Intracellular staining for cytokines. Single cell suspensions from spleen were prepared from immunized mice and cultured at 10×10$^6$ cells/ml in stimulation media containing 50 μg/ml of MOG 35-55. The cells were stimulated for 24 hrs, the last 5 hrs in the presence of Brefeldin A. The cells were then stained with anti-Vβ8.1/8.2 TCR FITC for 30 min at 4° C. prior to fixation and permeabilization with cytofix/cytoperm solution (Pharmingen, Inc.). The cells were then stained with anti-cytokine antibodies labeled with phycoerythrin (anti-mouse IFN-γ, TNF-α, IL-4, IL-10, and IL-12 from Pharmingen Inc.) for 30 min at 4° C. The cells were washed twice in perm/wash buffer (Pharmingen, Inc.) and once in FACS staining buffer (PBS, 1% BSA, 0.05% NaN$_3$) prior to two-color FACS analysis on a FACScan instrument (Beckton-Dickenson, Inc., Sunnyvale, Calif.) using Cell Quest software (Beckton-Dickenson, Inc.). For each experiment the cells were stained with isotype control antibodies to establish background staining and to set the quadrants prior to calculating the percent positive cells.

CNS mononuclear cells were isolated from perfused brain and spinal cord by percol gradient centrifugation as described in Bebo et al., *J. Neurosci. Res.* 52:420-429 (1998). The cells were stimulated with MOG-35-55 peptide for 24 hrs, the last 5 hrs in the presence of Brefeldin A. The cells were then stained with anti-CD4 cychrome labeled antibodies prior to fixation and permeabilization. The cells were subsequently stained with Vβ8.1/8.2 TCR-FITC and the indicated cytokine specific antibody coupled to PE and analyzed by three-color flow cytometry. For each experiment the cells were stained with isotype control antibodies to establish background staining and to set the quadrants prior to calculating the percent positive cells.

Statistical analysis. Significant differences in incidence and mortality between untreated and E2 treated mice were assessed by Chi-square analysis, Difference in onset was determined using the two-tailed Student t test. Differences in peak score and cumulative disease index (CDI) were assessed by the Mann-Whitney test. Statistical significance of the frequency of cytokine secreting cells was analyzed using Student's t test for comparisons of two means. Differences in the expression of chemokine and cytokine mRNA were also determined using the Student t test. Values of p<0.05 were considered significant.

Results

Figure 17A:
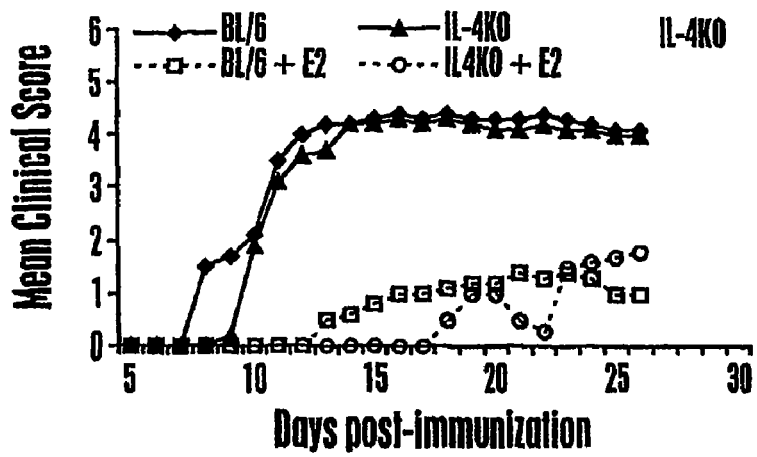
FIG. 17 shows the effect of 17β-estradiol on the severity of EAE in wildtype C57BL/6 and cytokine knockout mice.
Figure 17B:
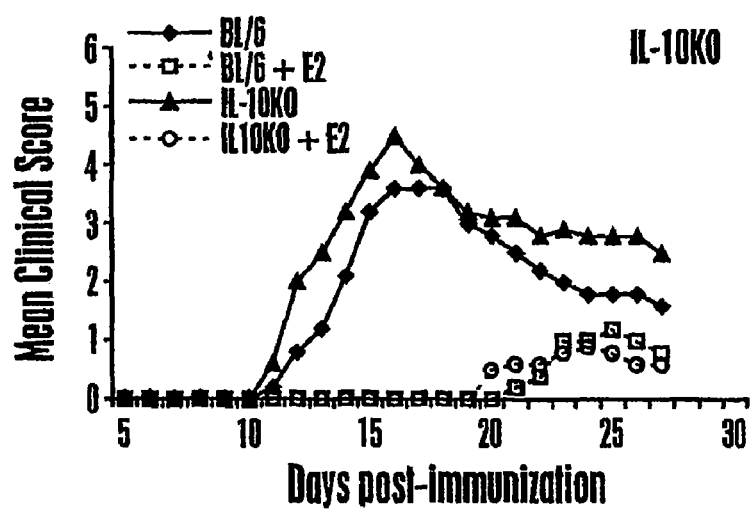
Figure 17C:
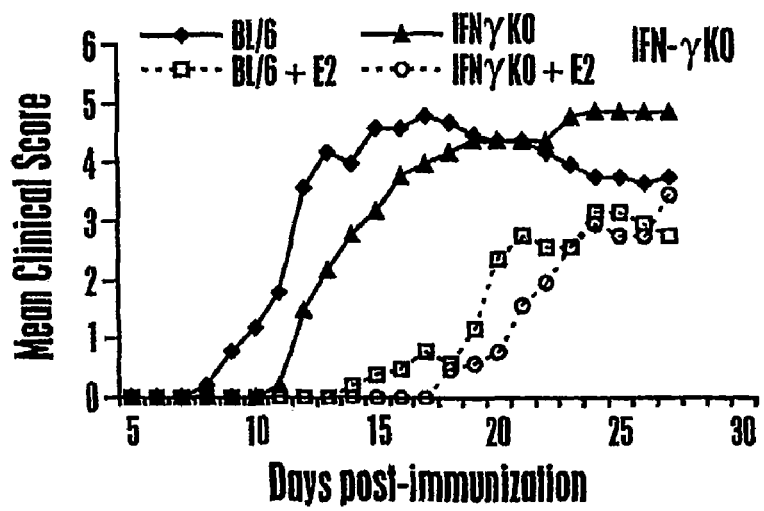
Figure 18A:
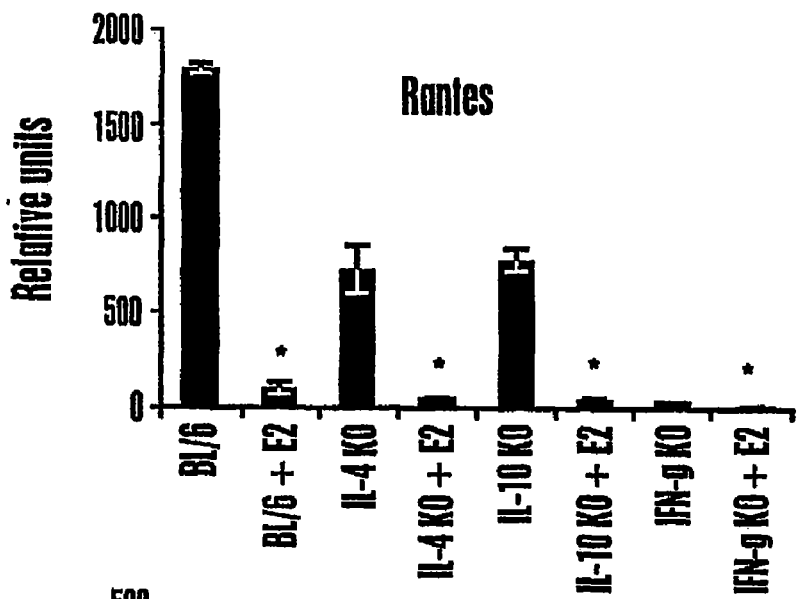
FIG. 18 shows data obtained from RPA analysis of chemokine and chemokine receptor mRNA expression in the spinal cords of untreated and estrogen treated wildtype and cytokine knockout mice with EAE.
Figure 18D:
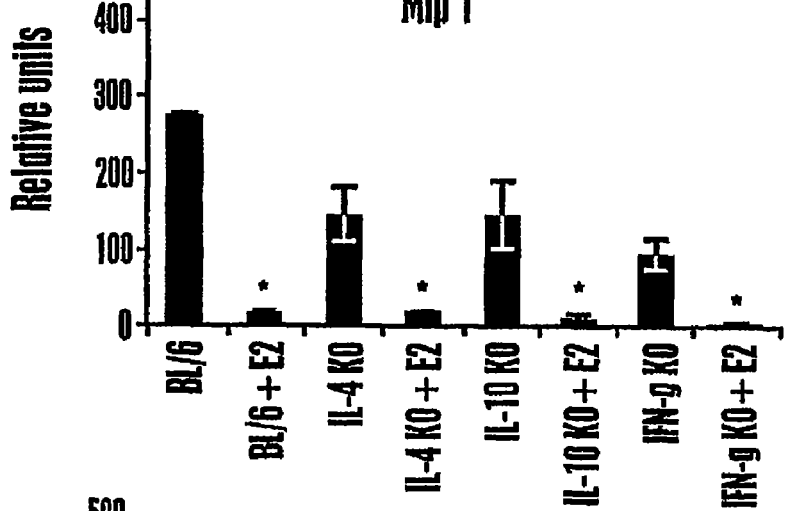
Figure 18G:
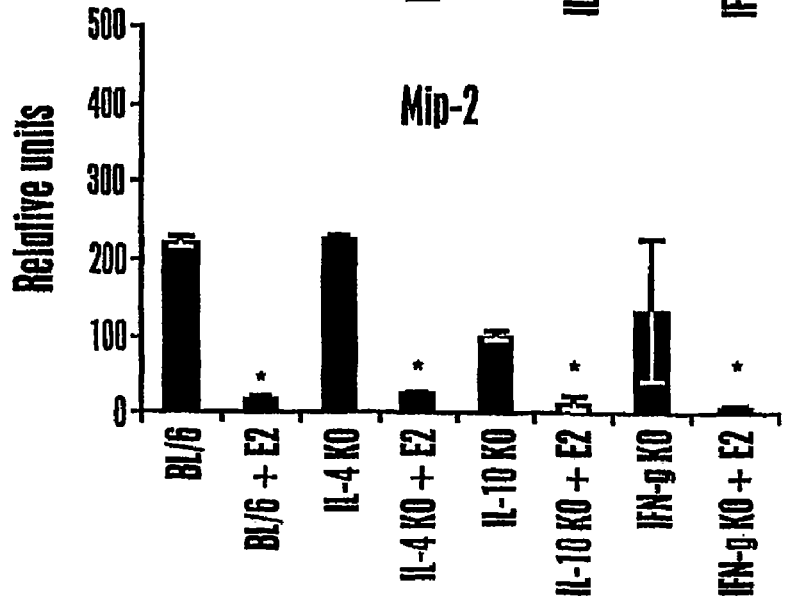
Figure 18B:
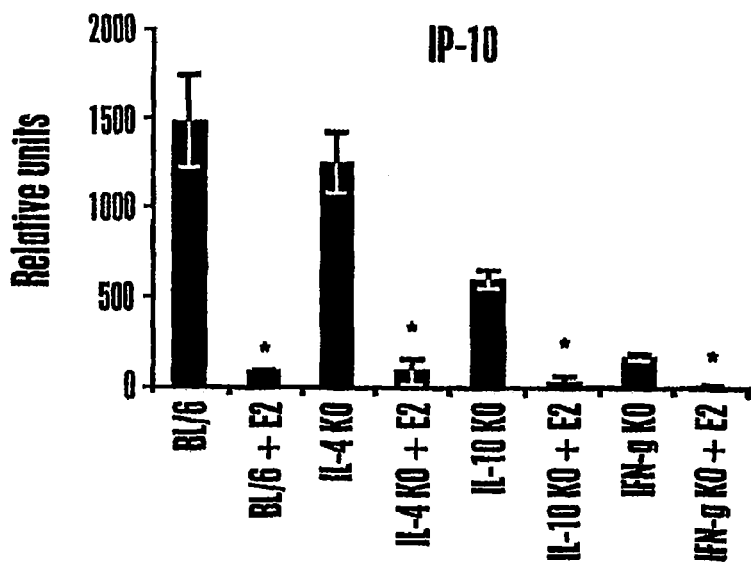
Figure 18E:
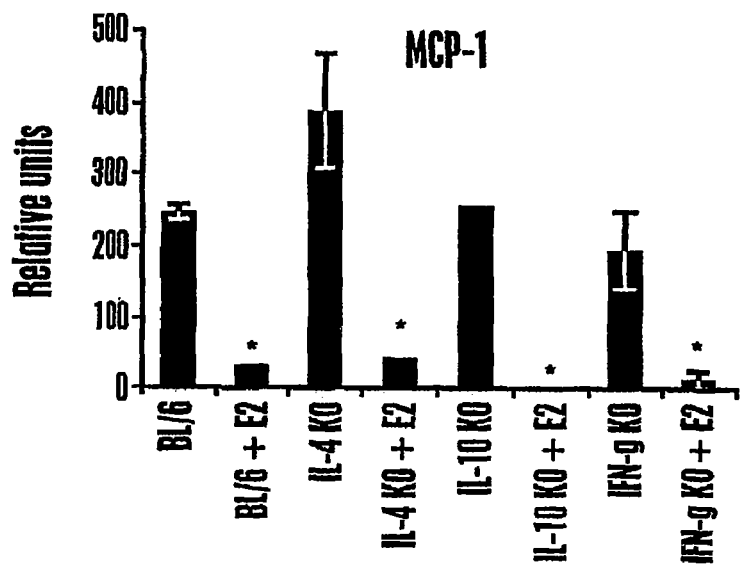
Figure 18H:
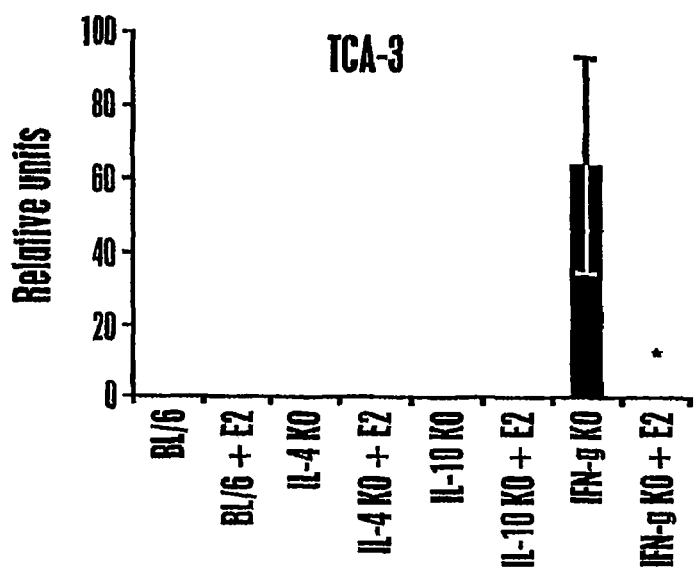
Figure 18C:
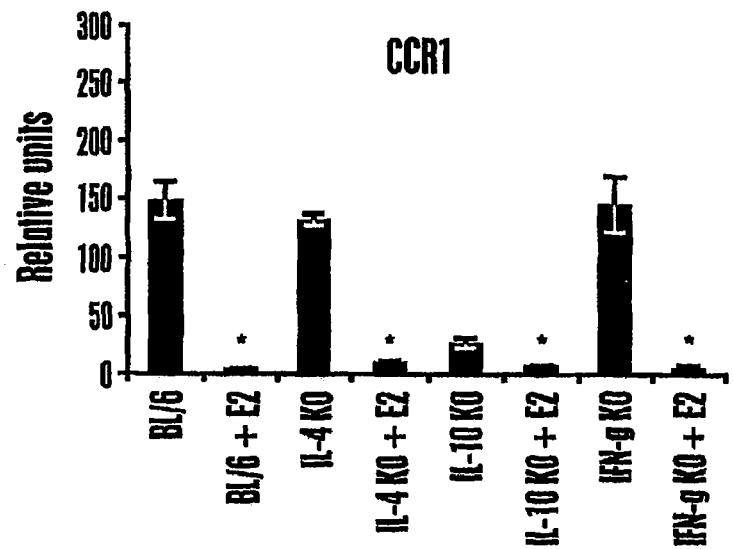
Figure 18F:
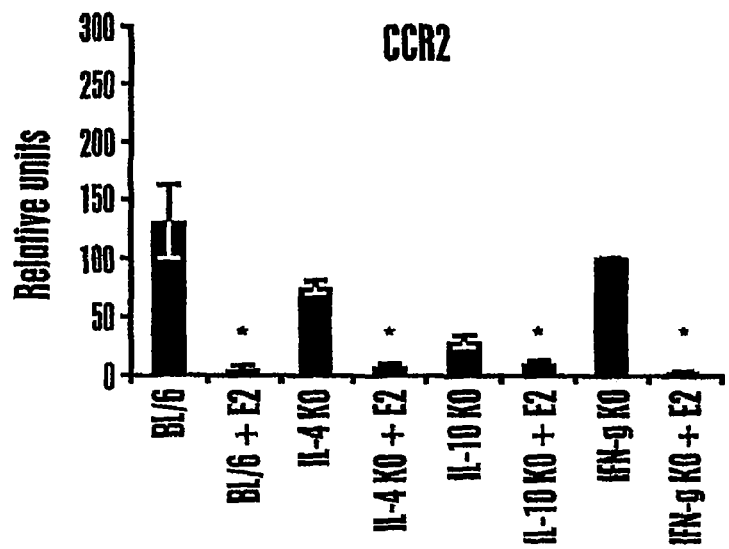
Figure 18I:
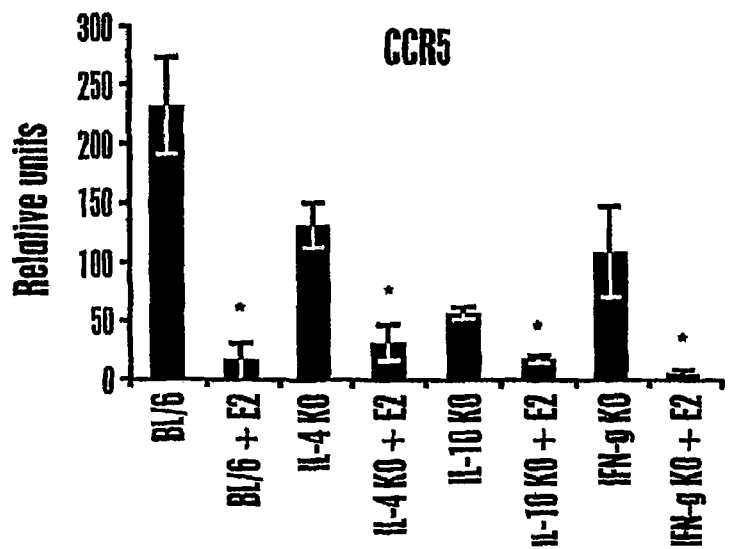

Estrogen treatment reduces the severity of EAE in C57BL/6 and cytokine deficient mice. The role of regulatory cytokines in estrogen-induced protection from EAE was examined using cytokine deficient mice. As described in Examples I-III, immunization with MOG 35-55 resulted in the induction of severe EAE in wild type (WT) C57BL/6 mice. No differences in disease severity were found in similarly immunized cytokine deficient mice (FIG. 17 and Table 16). C57BL/6 mice implanted with 17β-estradiol (E2)-containing pellets had a lower incidence of EAE, and developed disease much later than untreated mice. However, EAE that eventually developed in some E2-treated mice was essentially equivalent in severity to untreated animals, possibly due to early depletion of the E2 pellets. Nevertheless, treatment with E2 exerted a profound reduction in both the incidence and cumulative disease index (CDI) of EAE, and significantly delayed onset of symptoms in those mice that eventually developed disease. Estrogen treatment had similar effects on mice deficient in IL-4, IL-10 and IFN-γ (FIG. 17 and Table 16). No statistically significant differences in the ability of E2 to protect cytokine deficient mice were found (as determined by the Fisher exact test).

TABLE 16

|  | E2 | Incidence | Onset | Mortality | Peak Score | CDI |
|---|---|---|---|---|---|---|
| B6 | − | 29/31 | 10.9 ± 1.9 | 3/31 | 5.1 ± 0.9 | 64.7 ± 27.0 |
|  | + | 19/31 | 20.8 ± 3.7 | 0/31 | 4.2 ± 1.2 | 15.1 ± 17.0 |
|  |  | p = 0.005* | P < 0.0001 | p = 0.238 | P = 0.222 | P < 0.0001 |
| IL-4 KO | − | 11/11 | 11.5 ± 2.3 | 3/11 | 5.5 ± 0.4 | 76.7 ± 20.1 |
|  | + | 8/11 | 20.6 ± 4.9 | 0/11 | 4.4 ± 1.0 | 18.4 ± 22.2 |
|  |  | p = 0.214 | P < 0.0001 | p = 0.214 | P = 0.561 | P < 0.0001 |
| IL-10 KO | − | 15/16 | 12.3 ± 1.3 | 2/16 | 4.9 ± 1.1 | 53.0 ± 27.2 |
|  | + | 6/17 | 22.0 ± 4.3 | 0/17 | 4.2 ± 0.8 | 6.5 ± 10.9 |
|  |  | p = 0.001 | P < 0.0001 | p = 0.227 | P = 0.977 | P < 0.0001 |
| IFNγ KO | − | 11/11 | 13.6 ± 2.6 | 1/11 | 4.9 ± 1.1 | 58.6 ± 22.4 |
|  | + | 8/10 | 21.8 ± 2.7 | 1/10 | 4.5 ± 1.2 | 19.3 ± 15.9 |
|  |  | p = 0.214 | P < 0.0001 | p = 1.000 | P = 0.999 | P < 0.018 |

MOG 35-55 immunized C57BL/6 and cytokine deficient mice had numerous inflammatory and demyelinating lesions in the spinal cord at the peak of EAE, and no significant differences in the number and size of the lesions were observed. Healthy C57BL/6 and cytokine deficient mice that were treated with E2 before immunization did not have any detectable lesions in the spinal cord (Table 17). Thus, it is apparent from these data that E2 can suppress the development of both the clinical and histopathological manifestations of EAE in the absence of IL-4, IL-10, or IFN-γ.

TABLE 17

|  | Treatment with E2 | Inflammatory Foci/Section* |
|---|---|---|
| C57BL/6 | + | 0.0 ± 0.0 |
|  | − | 5.7 ± 1.7 |
| IFN-γKO | + | 0.0 ± 0.0 |
|  | − | 5.7 ± 4.1 |
| IL-4KO | + | 0.0 ± 0.0 |
|  | − | 7.0 ± 1.5 |
| IL-10KO | + | 0.0 ± 0.0 |
|  | − | 8.0 ± 1.9 |

Estrogen treatment reduces chemokine and chemokine receptor mRNA expression in the CNS. The egress of inflammatory cells into the CNS is a critical first step in the development of EAE. Chemokines are low molecular weight chemotactic molecules that are thought to play an important role in the migration and retention of immunocompetent cells in the CNS. The influence of E2 treatment on chemokine and chemokine receptor mRNA in the spinal cords of WT and cytokine deficient mice was measured using the RNAse protection assay (RPA). Total RNA was purified from spinal cords collected from mice at the peak of EAE (day 12-16 post-immunization) and chemokine/chemokine receptor specific mRNA was detected using radiolabeled riboprobes. mRNAs coding for many of the chemokine and receptor family members were detectable in the spinal cords of WT C57BL/6 mice with EAE (FIG. 18). RANTES and IP-10 were expressed at the highest levels, followed by MIP-1α, MIP-2 and MCP-1. The levels of TCA-3 mRNA were below the limits of detection for this assay. CCR5 was the most abundant chemokine receptor, followed by CCR1 and CCR2 (FIG. 18), whereas CCR1b, CCR3, and CCR4 were below the level of detection.

The expression of chemokine and chemokine receptor mRNA in cytokine deficient mice with EAE was often markedly different from that in WT mice (FIG. 18). IL-4 deficient mice had reduced expression of RANTES and MIP-1α, but increased expression of MCP-1, whereas IL-10 and IFN-γ deficient mice had reduced expression of all chemokines tested except MCP-1. Of interest, TCA-3 mRNA was only detectable in INF-γ deficient mice. The expression of CCR1, CCR2, and CCR5' was nearly absent in IL-10 deficient mice, but was only moderately altered in IL-4 and IFN-γ deficient mice. Thus, although distinct variations in the pattern of chemokine or chemokine receptor expression occurred in the different cytokine knockout mice, the development of EAE was not significantly changed. These preliminary data provide evidence of the complex interactions between chemokines and cytokines.

The expression of all chemokine and chemokine receptor mRNA was significantly diminished or absent in both WT and cytokine deficient mice treated with E2 (FIG. 18). This effect is likely the result of an E2-dependent decrease in the trafficking of inflammatory cells into the CNS, and possibly to its ability to inhibit the production of key inflammatory factors.

Figure 19A:
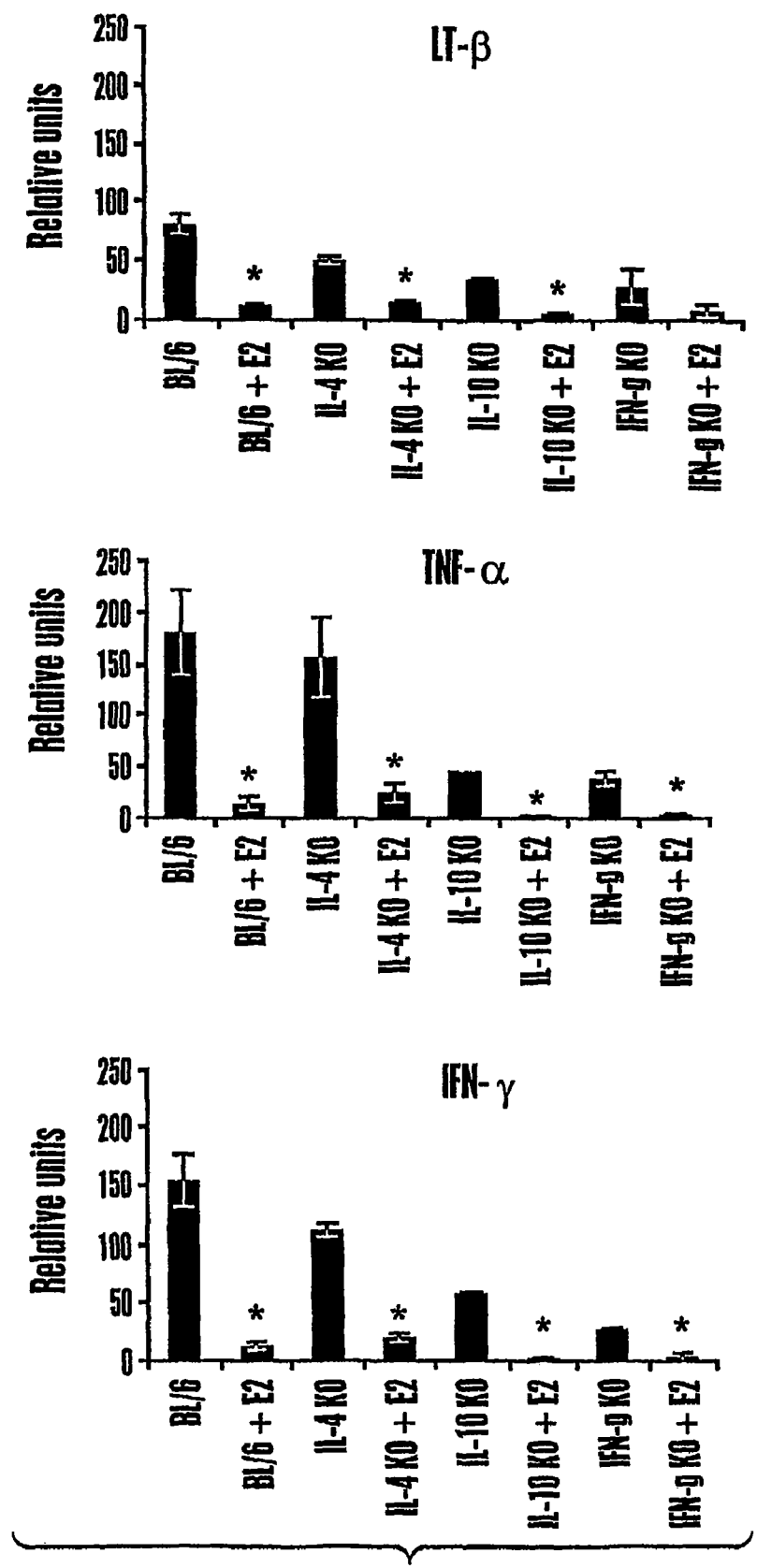
FIG. 19 shows cytokine production in the CNS of untreated and estrogen treated wildtype and cytokine knockout mice. Panel A shows data obtained from RPA analysis of total RNA from the spinal cords of mice at the peak of EAE. Panel B shows by FACS analysis the percentages of Vβ8.2+, MOG 35-55 stimulated T cells that express the indicated cytokines with or without 17β-estradiol treatment.

Estrogen treatment reduced cytokine production in the CNS. The expression of cytokine mRNA in the spinal cords of mice at the peak of EAE (day 12-16 post-immunization) was measured by RPA analysis. Messenger RNA encoding the pro-inflammatory cytokines IFN-γ, TNF-α, and LT-β were the most abundant (FIG. 19A). However, differences in the expression level of cytokine mRNA were apparent in the cytokine deficient mice. Messenger RNA for both TNF-α and IFN-γ were substantially lower in IL-10 knockout mice compared to WT, but no significant differences in LT-β levels were noted. Messenger RNA for all three cytokines was profoundly lower in IFN-γ knockout mice compared to WT mice.

Surprisingly, low levels of IFN-γ mRNA were detected in IFN-γ deficient mice. These mice were created by homologous recombination of the first exon (Dalton et al., Science 259:1739-1742 (1993), leaving the second exon intact. Although it has not been reported previously, it is possible that an mRNA product coding for the second exon is expressed and detected in our assay. Nevertheless, it is clear that lymphocytes from these mice fail to make a functional IFN-γ protein when measured by intracellular cytokine staining.

In all groups of mice, the levels of IL-4, IL-10, and TNF-β (LT-α) were below the limits of detection. The levels of LT-β, TNF-α, and IFN-γ mRNA in the spinal cords of E2 treated C57BL/6 and cytokine knockout mice were significantly reduced compared to untreated groups (FIG. 19A), with the exception of LT-β levels in IFN-γ deficient mice.

Figure 19B:
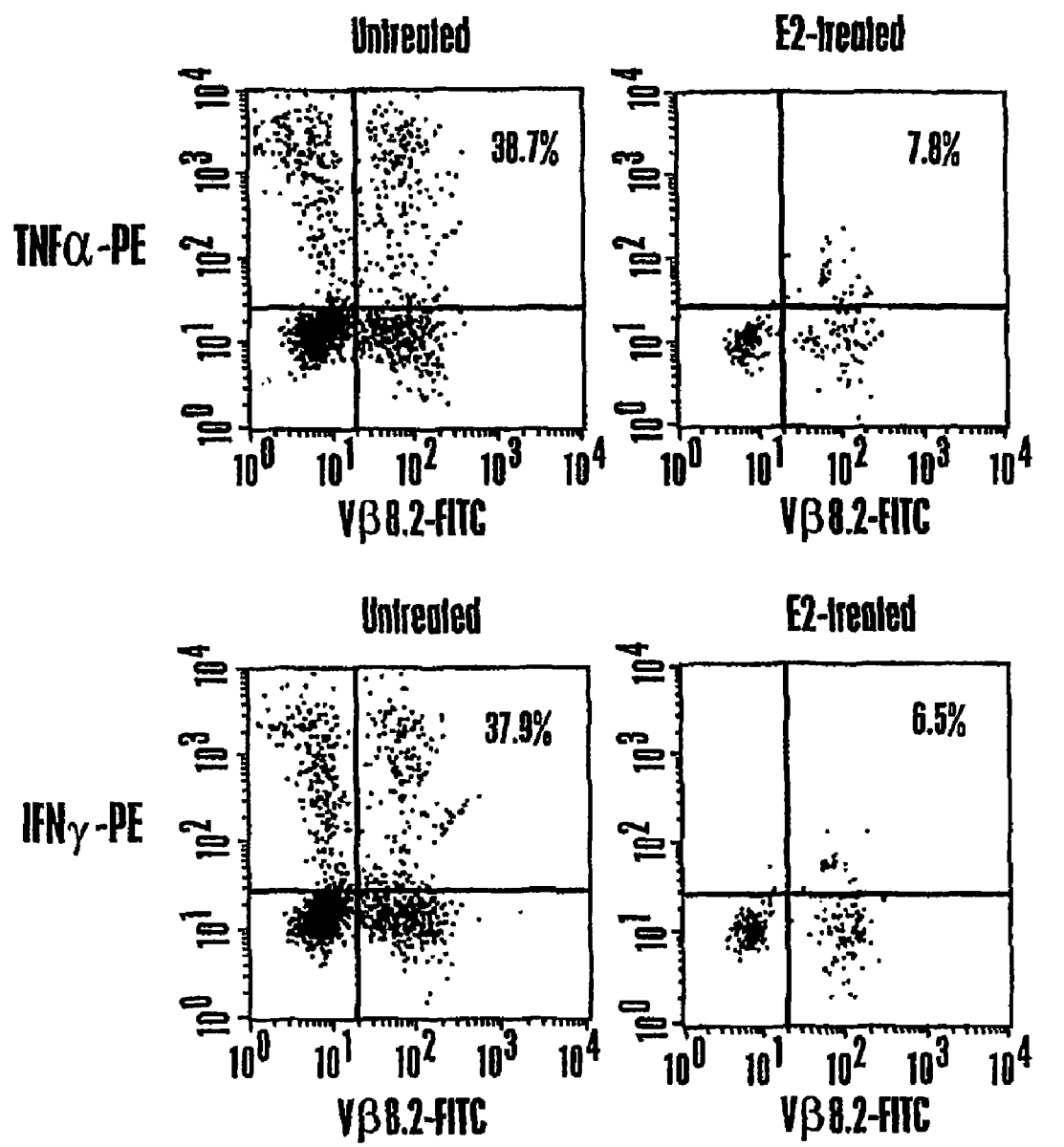
Figure 20A:
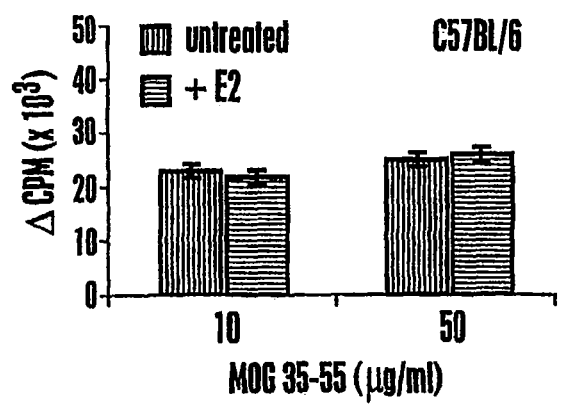
FIG. 20 shows the effect of estrogen treatment on MOG 35-55 stimulated T cell proliferation and the expression of cell adhesion and activation markers in wildtype and cytokine knockout mice.
Figure 20B:
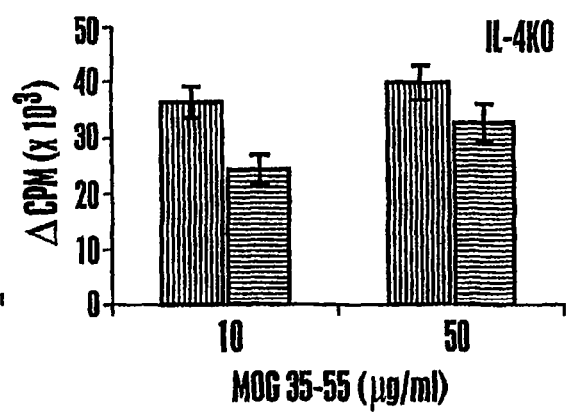
Figure 20C:
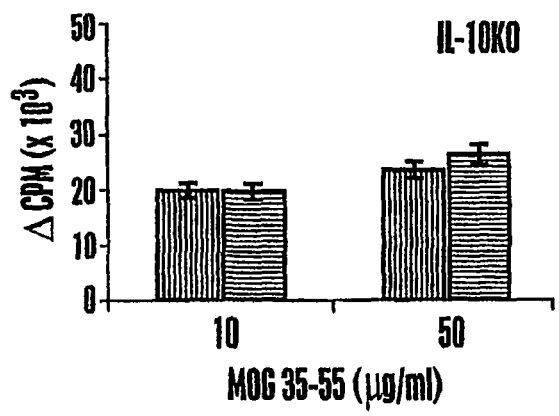
Figure 20D:
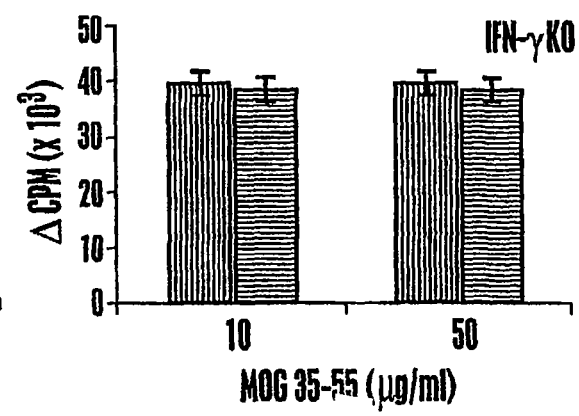

Intracellular staining of CNS mononuclear cells with anti-cytokine antibodies was also performed. Mononuclear cells were recovered from the brain and spinal cords of perfused mice at the peak of clinical disease. The total number of mononuclear cells recovered from the perfused CNS of untreated mice was 4-5 times higher than the number isolated from E2 treated mice. These cells were stained with anti-CD4 cytochrome labeled antibodies and the frequency of cytokine producing Vβ8.2+ helper T cells was measured by staining with anti-Vβ8.2-FITC and PE-labeled cytokine specific antibodies. As is shown in FIG. 19B, there was a dramatic reduction in the frequency and staining intensity (p<0.0001) of TNF-α and IFN-γ producing CD4+ T cells in the CNS of E2 treated mice. Based on total cell numbers recovered, E2 treatment caused a reduction of pro-inflammatory cytokine producing CD4+ Vβ8.2+ T cells in CNS from 29,000 cells/mouse to only 390 cells/mouse. A substantial reduction of pro-inflammatory cytokine producing CD4+, Vβ8.2– T cells was also observed (FIG. 19B). Taken together, these data confirm the RPA data presented above, and directly support the hypothesis that E2 treatment inhibits the activation and infiltration of pro-inflammatory cells into the CNS.

Estrogen treatment failed to alter T cell proliferation and the expression of cell surface adhesion and activation antigens. Proliferation of draining lymph node (LN) cells from either untreated or E2 treated mice was measured to determine if E2 could alter the ability of T lymphocytes to recognize and respond to the immunizing antigen. LN cells were isolated from three representative mice for each group and the cells pooled prior to stimulation with MOG 35-55 for 72 hr. The results shown in FIG. 20 illustrate that there was no effect of E2 treatment on the LN proliferation response to MOG 35-55 in WT and cytokine deficient mice. Similarly, E2 treatment did not alter the response to antigen of splenocytes. These results indicate that E2 treatment prevents the development of EAE without altering the ability of MOG 35-55 specific T cells to proliferate in response to antigen.

The regulation of cell adhesion molecules is another possible mechanism by which estrogen treatment controls the migration of inflammatory cells into the CNS. The expression of cell surface adhesion and activation/memory antigens was determined by staining with fluorochrome-labeled antibodies and flow cytometry. No significant differences in the expression of VLA-4, CD44, or CD62L were detected between LN cells from E2 versus control mice with EAE (Table 18). Furthermore, no differences in activation markers (CD69, CD25, FASL, CD40L, CD28) were seen.

ment promotes a shift towards Th2 immunity, the frequency of both pro- and anti-inflammatory cytokine producing cells in untreated and E2 treated mice was assessed, using the intracellular cytokine staining technique. Spleen cells were prepared from untreated and E2 treated mice at the peak of EAE (day 12-16 post-immunization) and stimulated with MOG 35-55 for 24 hr, the last 6 hr in the presence of Brefeldin A. The cells were stained with FITC labeled anti-Vβ8.1/8.2 TCR antibodies prior to fixation and permeabilization, and then were stained with the indicated phycoerythrin labeled anti-cytokine antibodies. Vβ8.1/8.2 TCR bearing T cells were focused on because they are thought to comprise a major population of the MOG-35-55 specific T cell responses in H-2b mice.

Figure 21A:
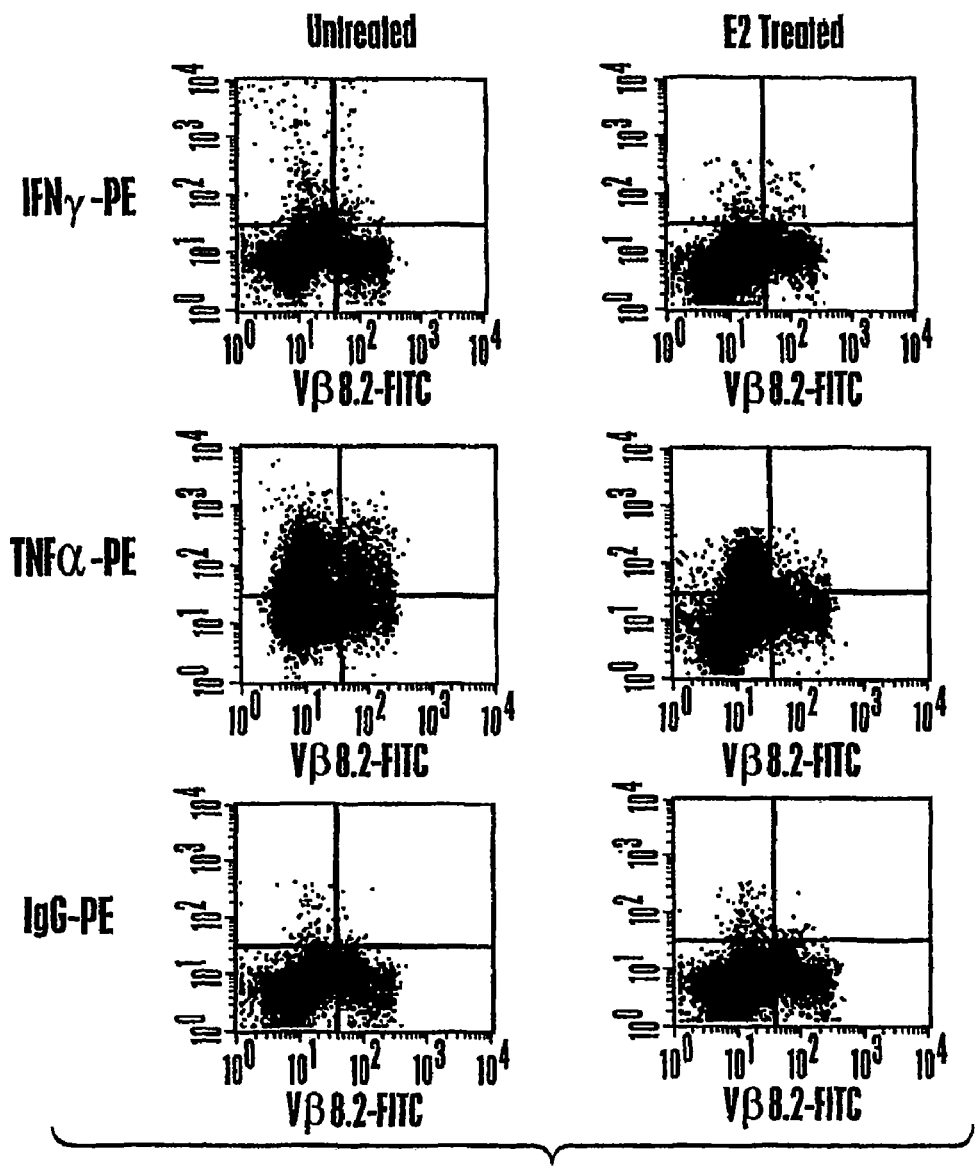
FIG. 21 shows the effect of estrogen treatment on the frequency of Vβ8.2 T cells expressing the indicated cytokines.
Figure 21B:
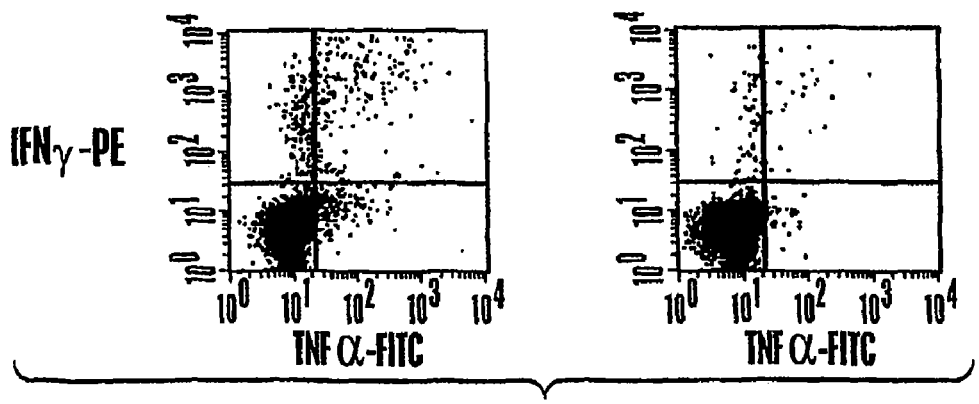
Figure 21C:
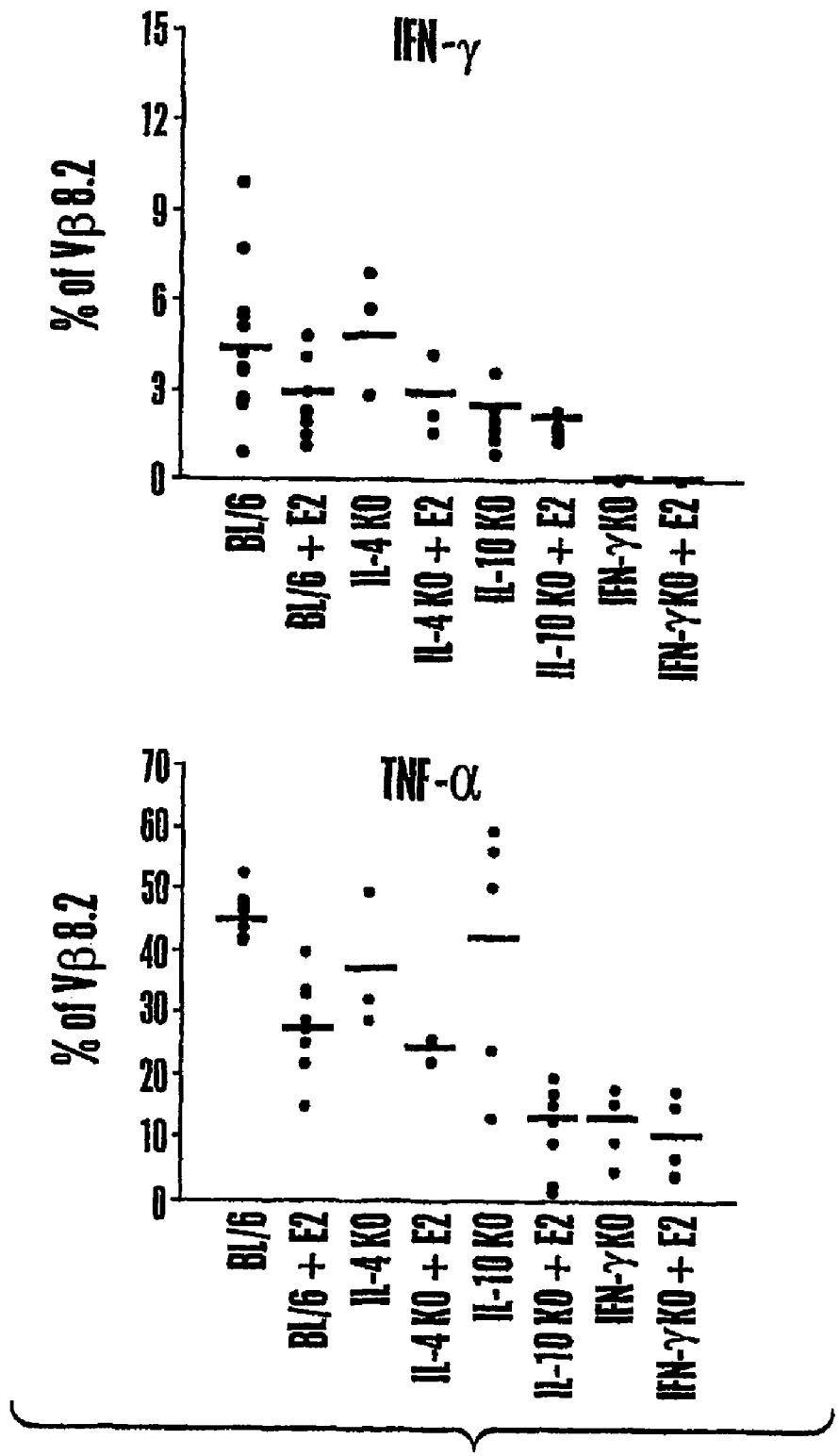

The frequency of IFN-γ and TNF-α producing Vβ8.1/8.2 TCR+ cells was similar in untreated C57BL/6, as well as IL-4 and IL-10 deficient mice with EAE. However, the frequency of TNF-α producing cells was significantly lower in IFN-γ knockout mice, and as expected, there were no detectable cells producing IFN-γ in these mice (FIG. 21 A-C). The frequency of TNF-α producing Vβ8.1/8.2 TCR+ cells was significantly diminished in C57BL/6 mice (p=0.004), in IL-4 knockout mice (p=0.06) and in IL-10 knockout mice (p=0.001) but no further reduction in the frequency of TNF-α producing cells was observed in E2 treated IFN-γ knockout mice (FIG. 21C). The diminution in staining intensity of cells from E2 treated mice also suggests that these cells also produce lower levels of TNF-α compared to the untreated mice. Since the number of Vβ8.1/8.2+ splenocytes recovered from the intact and cytokine knockout mice was quite similar, it can be concluded that the total number of TNF-α producing, MOG-reactive lymphocytes in the spleens of E2 treated mice was significantly reduced. The frequency of Vβ8.2-cells producing TNF-α was also reduced in all of the E2-treated mouse groups, suggesting that estrogen may influence cytokine production by encephalitogenic or recruited T cells expressing different V genes, as well as other inflammatory cells including macrophages.

The frequency of cells producing IFN-γ, IL-4, IL-10 and IL-12 was also measured. Although there was a trend for E2 treated mice to have a lower frequency of IFN-γ producing cells (FIGS. 212B and C), these values failed to attain statistical significance (p>0.05). Furthermore, the frequency of IL-4, IL-10 and IL-12 producing cells was always below the limits of detection for this assay. The failure to detect IL-4 and

TABLE 18

| | % of Vβ8.2+/CD4+ T CELLS | | | | | | | |
|---|---|---|---|---|---|---|---|---|
| | VLA-4 | CD44hi | CD69 | FASL | CD25 | CD40L | CD28 | CD62lo |
| untreated | | | | | | | | |
| Exp #1 | 69.4 | 41.6 | 12.2 | 2.1 | 5.4 | 0 | 3.6 | 32.4 |
| Exp #2 | 68.8 | 34.2 | 13.8 | 3.8 | 17.7 | nd | nd | nd |
| Exp #3 | 65.3 | 36.5 | nd | nd | nd | nd | nd | nd |
| mean | 67.8 ± 2.2 | 37.4 ± 3.8 | 13.1 ± 1.1 | 3.0 ± 1.2 | 11.6 ± 8.7 | | | |
| E2 treated | | | | | | | | |
| Exp #1 | 64.2 | 68.8 | 17.5 | 0.1 | 4.3 | 0 | 4.5 | 47.3 |
| Exp #2 | 58.7 | 41.2 | 25.7 | 3.1 | 10.4 | nd | nd | nd |
| Exp #3 | 49.6 | 57.3 | nd | nd | nd | nd | nd | nd |
| mean | 57.5 ± 7.4 | 55.8 ± 13.8 | 21.6 ± 5.8 | 1.6 ± 2.1 | 7.4 ± 4.3 | | | |
| P value | 0.126 | 0.141 | 0.274 | 0.534 | 0.622 | | | |

Estrogen treatment reduced the frequency of TNF-α secreting cells. In order to determine whether estrogen treat- IL-10 reactive cells suggests that E2 treatment did not significantly shift the cytokine response towards Th2 production.

EAE was suppressed in TNF-α deficient mice. The data presented above implicate TNF-α producing cells as probable contributors to induction of EAE. In order to further evaluate the pathogenic contribution of TNF-α in this model, the severity of EAE was compared in TNF-α deficient and WT control mice. Severe EAE developed in the majority of WT mice after immunization with MOG-35-55 peptide (Table 19). However, the incidence and severity of EAE in TNF-α deficient mice was greatly diminished. Not only did fewer mice develop disease, but the mean peak disease score and the cumulative disease index were also profoundly reduced (Table 19). These data demonstrate that TNF-α producing cells are major contributors to EAE induction, and their regulation by E2 provides an important new insight into the regulatory effects of estrogen.

TABLE 19

|  | Incidence | Onset | Mortality | Peak | CDI |
|---|---|---|---|---|---|
| BL6.129s | 8/8 | 11.8 ± 3.1 | 3/8 | 4.9 ± 1.5 | 78.3 ± 35.8 |
| TNF-α KO | 4/7 | 13.0 ± 0.8 | 0/7 | 0.6 ± 0.6 | 2.6 ± 4.6 |
| P value | 0.153* | 0.340 | 0.244 | <0.0001 | <0.0001 |

All journal article, reference and patent citations provided above, in parentheses or otherwise, are incorporated herein by reference in their entirety.

Although the invention has been described with reference to the examples provided above, it should be understood that various modifications can be made without departing from the spirit of the invention.

What is claimed is:

1. A method of ameliorating multiple sclerosis in a human subject, comprising
   selecting a human subject having multiple sclerosis; and
   administering a dose of estriol to the human subject sufficient to raise the serum concentration of estriol in the human subject to within the range from 30 pg/ml to 2,000 pg/ml,
   thereby ameliorating multiple sclerosis in said human subject.

2. The method of claim 1, wherein the human subject is female.

3. The method of claim 1, wherein the human subject is male.

4. The method of claim 1, wherein the dose of estriol raises the serum concentration of estriol to within the range from 30 pg/ml to 1,000 pg/ml.

5. The method of claim 1, wherein the dose of estriol raises the serum concentration of estriol in the human subject to within the range from 50 pg/ml to 500 pg/ml.

6. The method of claim 1, wherein the estriol is administered by a route selected from an oral, a transdermal, a respiratory, a subcutaneous and an intravenous route.

7. The method of claim 1, further comprising administering to the human subject a therapeutically effective amount of an immunotherapeutic agent.

8. The method of claim 1, further comprising administering to the human subject a therapeutically effective amount of an immunomodulatory agent.

9. A method of ameliorating multiple sclerosis in a human subject, comprising
   selecting a human subject with multiple sclerosis; and
   administering estriol to the human subject in an amount sufficient to raise the serum concentration of estriol in said human subject to within the range from 10 pg/ml to 2,000 pg/ml and
   thereby ameliorating multiple sclerosis in said human subject.

10. The method of claim 9, wherein said human subject is female.

11. The method of claim 9, wherein said human subject is male.

12. The method of claim 9, wherein said estriol is administered by a route selected from an oral, a transdermal, a respiratory, a subcutaneous and an intravenous route.

13. The method of claim 9, wherein said amelioration is apparent by magnetic resonance imaging.

14. The method of claim 9, comprising administering estriol to said human subject sufficient to raise the serum concentration of estriol in said human to within the range from 100 pg/ml to 2,000 pg/ml.

* * * * *

SEQUENCE LISTING

<160> NUMBER OF SEQ ID NOS: 127

<210> SEQ ID NO 1
<211> LENGTH: 20
<212> TYPE: PRT
<213> ORGANISM: Homo sapiens

<400> SEQUENCE: 1

Leu Gly Leu Arg Leu Ile Tyr Phe Ser Tyr Asp Val Lys Met Lys Glu
1               5                   10                  15

Lys Gly Asp Ile
            20

<210> SEQ ID NO 2
<211> LENGTH: 21
<212> TYPE: PRT
<213> ORGANISM: Homo sapiens

<400> SEQUENCE: 2

Ala Leu Gly Gln Gly Pro Gln Phe Ile Phe Gln Tyr Tyr Glu Glu Glu
1               5                   10                  15

Glu Arg Gln Arg Gly
            20

<210> SEQ ID NO 3
<211> LENGTH: 21
<212> TYPE: PRT
<213> ORGANISM: Homo sapiens

<400> SEQUENCE: 3

Ala Leu Gly Gln Gly Pro Gln Phe Ile Phe Gln Thr Tyr Glu Glu Glu
1               5                   10                  15

Glu Arg Gln Arg Gly
            20

<210> SEQ ID NO 4
<211> LENGTH: 21
<212> TYPE: PRT
<213> ORGANISM: Homo sapiens

<400> SEQUENCE: 4

Leu Gly Gln Gly Pro Glu Phe Leu Ile Tyr Phe Gln Gly Thr Gly Ala
1               5                   10                  15

Ala Asp Asp Ser Gly

```
<210> SEQ ID NO 5
<211> LENGTH: 20
<212> TYPE: PRT
<213> ORGANISM: Homo sapiens

<400> SEQUENCE: 5

Leu Gly Gln Gly Pro Glu Phe Leu Thr Tyr Phe Gln Asn Glu Ala Gln
1               5                   10                  15

Leu Glu Lys Ser
            20

<210> SEQ ID NO 6
<211> LENGTH: 19
<212> TYPE: PRT
<213> ORGANISM: Homo sapiens

<400> SEQUENCE: 6

Gly Leu Arg Leu Ile His Tyr Ser Val Gly Ala Gly Ile Thr Asp Gln
1               5                   10                  15

Gly Glu Val

<210> SEQ ID NO 7
<211> LENGTH: 17
<212> TYPE: PRT
<213> ORGANISM: Homo sapiens

<400> SEQUENCE: 7

Ser Met Asn Val Glu Val Thr Asp Lys Gly Asp Val Pro Glu Gly Tyr
1               5                   10                  15

Lys

<210> SEQ ID NO 8
<211> LENGTH: 17
<212> TYPE: PRT
<213> ORGANISM: Homo sapiens

<400> SEQUENCE: 8

Ser Gln Ile Val Asn Asp Phe Gln Lys Gly Asp Ile Ala Glu Gly Tyr
1               5                   10                  15

Ser

<210> SEQ ID NO 9
<211> LENGTH: 21
<212> TYPE: PRT
<213> ORGANISM: Homo sapiens

<400> SEQUENCE: 9

Ser Leu Asp Gln Gly Leu Gln Phe Leu Ile Gln Tyr Tyr Asn Gly Glu
1               5                   10                  15

Glu Arg Ala Lys Gly
            20

<210> SEQ ID NO 10
<211> LENGTH: 21
<212> TYPE: PRT
<213> ORGANISM: Homo sapiens

<400> SEQUENCE: 10

Ser Leu Asp Gln Gly Leu Gln Phe Leu Ile His Tyr Tyr Asn Gly Glu
1               5                   10                  15
```

Glu Arg Ala Lys Gly
            20

<210> SEQ ID NO 11
<211> LENGTH: 21
<212> TYPE: PRT
<213> ORGANISM: Homo sapiens

<400> SEQUENCE: 11

Phe Pro Lys Gln Ser Leu Met Leu Met Ala Thr Ser Asn Glu Gly Ser
1               5                   10                  15

Lys Ala Thr Tyr Glu
            20

<210> SEQ ID NO 12
<211> LENGTH: 21
<212> TYPE: PRT
<213> ORGANISM: Homo sapiens

<400> SEQUENCE: 12

Phe Pro Lys Lys Ser Leu Met Leu Met Ala Thr Ser Asn Glu Gly Ser
1               5                   10                  15

Lys Ala Thr Tyr Glu
            20

<210> SEQ ID NO 13
<211> LENGTH: 21
<212> TYPE: PRT
<213> ORGANISM: Homo sapiens

<400> SEQUENCE: 13

Phe Pro Lys Gln Ser Leu Met Leu Met Ala Thr Ser Asn Glu Gly Cys
1               5                   10                  15

Lys Ala Thr Tyr Glu
            20

<210> SEQ ID NO 14
<211> LENGTH: 21
<212> TYPE: PRT
<213> ORGANISM: Homo sapiens

<400> SEQUENCE: 14

Phe Pro Lys Lys Ser Leu Met Gln Ile Ala Thr Ser Asn Glu Gly Ser
1               5                   10                  15

Lys Ala Thr Tyr Glu
            20

<210> SEQ ID NO 15
<211> LENGTH: 21
<212> TYPE: PRT
<213> ORGANISM: Homo sapiens

<400> SEQUENCE: 15

Asp Pro Gly Leu Gly Leu Arg Leu Ile Tyr Phe Ser Tyr Asp Val Lys
1               5                   10                  15

Met Lys Glu Lys Gly
            20

<210> SEQ ID NO 16
<211> LENGTH: 21
<212> TYPE: PRT
<213> ORGANISM: Homo sapiens

```
<400> SEQUENCE: 16

Gln Pro Gly Gln Ser Leu Thr Leu Ile Ala Thr Ala Asn Gln Gly Ser
1               5                   10                  15

Glu Ala Thr Tyr Glu
            20

<210> SEQ ID NO 17
<211> LENGTH: 21
<212> TYPE: PRT
<213> ORGANISM: Homo sapiens

<400> SEQUENCE: 17

Thr Pro Gly Gln Gly Leu Gln Phe Leu Phe Glu Tyr Phe Ser Glu Thr
1               5                   10                  15

Gln Arg Asn Lys Gly
            20

<210> SEQ ID NO 18
<211> LENGTH: 21
<212> TYPE: PRT
<213> ORGANISM: Homo sapiens

<400> SEQUENCE: 18

Thr Leu Gly Gln Gly Leu Gln Phe Leu Phe Glu Tyr Phe Ser Glu Thr
1               5                   10                  15

Gln Arg Asn Lys Gly
            20

<210> SEQ ID NO 19
<211> LENGTH: 21
<212> TYPE: PRT
<213> ORGANISM: Homo sapiens

<400> SEQUENCE: 19

Ala Leu Gly Gln Gly Pro Gln Phe Ile Phe Gln Tyr Tyr Glu Glu Glu
1               5                   10                  15

Glu Arg Gln Arg Gly
            20

<210> SEQ ID NO 20
<211> LENGTH: 21
<212> TYPE: PRT
<213> ORGANISM: Homo sapiens

<400> SEQUENCE: 20

Val Leu Gly Gln Gly Pro Gln Phe Ile Phe Gln Tyr Tyr Glu Lys Glu
1               5                   10                  15

Glu Arg Gly Arg Gly
            20

<210> SEQ ID NO 21
<211> LENGTH: 21
<212> TYPE: PRT
<213> ORGANISM: Homo sapiens

<400> SEQUENCE: 21

Ala Leu Gly Leu Gly Leu Gln Leu Leu Leu Trp Tyr Asp Glu Gly Glu
1               5                   10                  15

Glu Arg Asn Arg Gly
            20
```

```
<210> SEQ ID NO 22
<211> LENGTH: 21
<212> TYPE: PRT
<213> ORGANISM: Homo sapiens

<400> SEQUENCE: 22

Ala Leu Gly Leu Gly Leu Gln Phe Leu Leu Trp Tyr Asp Glu Gly Glu
 1               5                  10                  15

Glu Arg Asn Arg Gly
            20

<210> SEQ ID NO 23
<211> LENGTH: 21
<212> TYPE: PRT
<213> ORGANISM: Homo sapiens

<400> SEQUENCE: 23

Ala Leu Gly Gln Gly Pro Gln Phe Ile Phe Gln Tyr Tyr Arg Glu Glu
 1               5                  10                  15

Glu Asn Gly Arg Gly
            20

<210> SEQ ID NO 24
<211> LENGTH: 21
<212> TYPE: PRT
<213> ORGANISM: Homo sapiens

<400> SEQUENCE: 24

Ser Leu Gly Gln Gly Pro Glu Phe Leu Ile Tyr Phe Gln Gly Thr Gly
 1               5                  10                  15

Ala Ala Asp Asp Ser
            20

<210> SEQ ID NO 25
<211> LENGTH: 21
<212> TYPE: PRT
<213> ORGANISM: Homo sapiens

<400> SEQUENCE: 25

Ser Leu Gly Gln Gly Pro Glu Leu Leu Ile Tyr Phe Gln Gly Thr Gly
 1               5                  10                  15

Ala Ala Asp Asp Ser
            20

<210> SEQ ID NO 26
<211> LENGTH: 21
<212> TYPE: PRT
<213> ORGANISM: Homo sapiens

<400> SEQUENCE: 26

Ala Leu Gly Gln Gly Pro Glu Phe Leu Thr Tyr Phe Gln Asn Glu Ala
 1               5                  10                  15

Gln Leu Asp Lys Ser
            20

<210> SEQ ID NO 27
<211> LENGTH: 21
<212> TYPE: PRT
<213> ORGANISM: Homo sapiens

<400> SEQUENCE: 27

Ala Leu Gly Gln Gly Pro Glu Phe Leu Thr Tyr Phe Asn Tyr Glu Ala
```

```
                1               5                  10                  15
Gln Gln Asp Lys Ser
            20

<210> SEQ ID NO 28
<211> LENGTH: 21
<212> TYPE: PRT
<213> ORGANISM: Homo sapiens

<400> SEQUENCE: 28

Thr Leu Gly Gln Gly Pro Glu Phe Leu Thr Tyr Phe Gln Asn Glu Ala
  1               5                  10                  15

Gln Leu Glu Lys Ser
            20

<210> SEQ ID NO 29
<211> LENGTH: 21
<212> TYPE: PRT
<213> ORGANISM: Homo sapiens

<400> SEQUENCE: 29

Asn Pro Gly Gln Gly Pro Glu Phe Leu Thr Tyr Phe Gln Asn Glu Ala
  1               5                  10                  15

Gln Leu Glu Lys Ser
            20

<210> SEQ ID NO 30
<211> LENGTH: 21
<212> TYPE: PRT
<213> ORGANISM: Homo sapiens

<400> SEQUENCE: 30

Ser Leu Gly Gln Gly Leu Glu Phe Leu Ile Tyr Phe Gln Gly Asn Ser
  1               5                  10                  15

Ala Pro Asp Lys Ser
            20

<210> SEQ ID NO 31
<211> LENGTH: 21
<212> TYPE: PRT
<213> ORGANISM: Homo sapiens

<400> SEQUENCE: 31

Ala Leu Gly Gln Gly Pro Glu Phe Leu Thr Tyr Phe Asn Tyr Glu Ala
  1               5                  10                  15

Gln Pro Asp Lys Ser
            20

<210> SEQ ID NO 32
<211> LENGTH: 21
<212> TYPE: PRT
<213> ORGANISM: Homo sapiens

<400> SEQUENCE: 32

Thr Leu Gly Gln Gly Ser Glu Val Leu Thr Tyr Ser Gln Ser Asp Ala
  1               5                  10                  15

Gln Arg Asp Lys Ser
            20

<210> SEQ ID NO 33
<211> LENGTH: 21
<212> TYPE: PRT
```

-continued

<213> ORGANISM: Homo sapiens

<400> SEQUENCE: 33

Lys Ala Lys Lys Pro Pro Glu Leu Met Phe Val Tyr Ser Tyr Glu Lys
1               5                   10                  15

Leu Ser Ile Asn Glu
            20

<210> SEQ ID NO 34
<211> LENGTH: 21
<212> TYPE: PRT
<213> ORGANISM: Homo sapiens

<400> SEQUENCE: 34

Ser Ala Lys Lys Pro Leu Glu Leu Met Phe Val Tyr Ser Leu Glu Glu
1               5                   10                  15

Arg Val Glu Asn Asn
            20

<210> SEQ ID NO 35
<211> LENGTH: 21
<212> TYPE: PRT
<213> ORGANISM: Homo sapiens

<400> SEQUENCE: 35

Ser Ala Lys Lys Pro Leu Glu Leu Met Phe Val Tyr Asn Phe Lys Glu
1               5                   10                  15

Gln Thr Glu Asn Asn
            20

<210> SEQ ID NO 36
<211> LENGTH: 21
<212> TYPE: PRT
<213> ORGANISM: Homo sapiens

<400> SEQUENCE: 36

Thr Met Met Arg Gly Leu Glu Leu Leu Ile Tyr Phe Asn Asn Asn Val
1               5                   10                  15

Pro Ile Asp Asp Ser
            20

<210> SEQ ID NO 37
<211> LENGTH: 21
<212> TYPE: PRT
<213> ORGANISM: Homo sapiens

<400> SEQUENCE: 37

Thr Met Met Gln Gly Leu Glu Leu Leu Ala Tyr Phe Arg Asn Arg Ala
1               5                   10                  15

Pro Leu Asp Asp Ser
            20

<210> SEQ ID NO 38
<211> LENGTH: 21
<212> TYPE: PRT
<213> ORGANISM: Homo sapiens

<400> SEQUENCE: 38

Asp Ser Lys Lys Phe Leu Lys Ile Met Phe Ser Tyr Asn Asn Lys Glu
1               5                   10                  15

Leu Ile Ile Asn Glu
            20

-continued

```
<210> SEQ ID NO 39
<211> LENGTH: 21
<212> TYPE: PRT
<213> ORGANISM: Homo sapiens

<400> SEQUENCE: 39

Lys Leu Glu Glu Glu Leu Lys Phe Leu Val Tyr Phe Gln Asn Glu Glu
 1               5                  10                  15

Leu Ile Gln Lys Ala
            20

<210> SEQ ID NO 40
<211> LENGTH: 21
<212> TYPE: PRT
<213> ORGANISM: Homo sapiens

<400> SEQUENCE: 40

Thr Leu Glu Glu Glu Leu Lys Phe Phe Ile Tyr Phe Gln Asn Glu Glu
 1               5                  10                  15

Ile Ile Gln Lys Ala
            20

<210> SEQ ID NO 41
<211> LENGTH: 21
<212> TYPE: PRT
<213> ORGANISM: Homo sapiens

<400> SEQUENCE: 41

Asp Pro Gly Met Glu Leu His Leu Ile His Tyr Ser Tyr Gly Val Asn
 1               5                  10                  15

Ser Thr Glu Lys Gly
            20

<210> SEQ ID NO 42
<211> LENGTH: 21
<212> TYPE: PRT
<213> ORGANISM: Homo sapiens

<400> SEQUENCE: 42

Asp Pro Gly His Gly Leu Arg Leu Ile His Tyr Ser Tyr Gly Val Lys
 1               5                  10                  15

Asp Thr Asp Lys Gly
            20

<210> SEQ ID NO 43
<211> LENGTH: 21
<212> TYPE: PRT
<213> ORGANISM: Homo sapiens

<400> SEQUENCE: 43

Asp Leu Gly His Gly Leu Arg Leu Ile His Tyr Ser Tyr Gly Val Gln
 1               5                  10                  15

Asp Thr Asn Lys Gly
            20

<210> SEQ ID NO 44
<211> LENGTH: 21
<212> TYPE: PRT
<213> ORGANISM: Homo sapiens

<400> SEQUENCE: 44
```

```
Asp Leu Gly His Gly Leu Arg Leu Ile His Tyr Ser Tyr Gly Val Lys
1               5                   10                  15

Asp Thr Asn Lys Gly
            20

<210> SEQ ID NO 45
<211> LENGTH: 21
<212> TYPE: PRT
<213> ORGANISM: Homo sapiens

<400> SEQUENCE: 45

Asp Leu Gly His Gly Leu Arg Leu Ile His Tyr Ser Tyr Gly Val His
1               5                   10                  15

Asp Thr Asn Lys Gly
            20

<210> SEQ ID NO 46
<211> LENGTH: 21
<212> TYPE: PRT
<213> ORGANISM: Homo sapiens

<400> SEQUENCE: 46

Asp Leu Gly His Gly Leu Arg Leu Ile Tyr Tyr Ser Ala Ala Ala Asp
1               5                   10                  15

Ile Thr Asp Lys Gly
            20

<210> SEQ ID NO 47
<211> LENGTH: 21
<212> TYPE: PRT
<213> ORGANISM: Homo sapiens

<400> SEQUENCE: 47

Asp Pro Gly Met Gly Leu Arg Leu Ile His Tyr Ser Val Gly Ala Gly
1               5                   10                  15

Ile Thr Asp Gln Gly
            20

<210> SEQ ID NO 48
<211> LENGTH: 21
<212> TYPE: PRT
<213> ORGANISM: Homo sapiens

<400> SEQUENCE: 48

Asp Pro Gly Met Gly Leu Arg Leu Ile His Tyr Ser Val Gly Glu Gly
1               5                   10                  15

Thr Thr Ala Lys Gly
            20

<210> SEQ ID NO 49
<211> LENGTH: 21
<212> TYPE: PRT
<213> ORGANISM: Homo sapiens

<400> SEQUENCE: 49

Asp Pro Gly Met Gly Leu Arg Leu Ile Tyr Tyr Ser Ala Ser Glu Gly
1               5                   10                  15

Thr Thr Asp Lys Gly
            20

<210> SEQ ID NO 50
<211> LENGTH: 21
```

```
<212> TYPE: PRT
<213> ORGANISM: Homo sapiens

<400> SEQUENCE: 50

Asp Pro Gly Met Gly Leu Arg Arg Ile His Tyr Ser Val Ala Ala Gly
 1               5                  10                  15

Ile Thr Asp Lys Gly
            20

<210> SEQ ID NO 51
<211> LENGTH: 21
<212> TYPE: PRT
<213> ORGANISM: Homo sapiens

<400> SEQUENCE: 51

Asp Leu Gly Leu Gly Leu Arg Leu Ile His Tyr Ser Asn Thr Ala Gly
 1               5                  10                  15

Thr Thr Gly Lys Gly
            20

<210> SEQ ID NO 52
<211> LENGTH: 21
<212> TYPE: PRT
<213> ORGANISM: Homo sapiens

<400> SEQUENCE: 52

Asp Pro Gly Met Gly Leu Lys Leu Ile Tyr Tyr Ser Val Gly Ala Gly
 1               5                  10                  15

Ile Thr Asp Lys Gly
            20

<210> SEQ ID NO 53
<211> LENGTH: 21
<212> TYPE: PRT
<213> ORGANISM: Homo sapiens

<400> SEQUENCE: 53

Asp Pro Gly Met Gly Leu Arg Leu Ile Tyr Tyr Ser Ala Ala Ala Gly
 1               5                  10                  15

Thr Thr Asp Lys Glu
            20

<210> SEQ ID NO 54
<211> LENGTH: 21
<212> TYPE: PRT
<213> ORGANISM: Homo sapiens

<400> SEQUENCE: 54

Asp Pro Gly Leu Gly Leu Arg Gln Ile Tyr Tyr Ser Met Asn Val Glu
 1               5                  10                  15

Val Thr Asp Lys Gly
            20

<210> SEQ ID NO 55
<211> LENGTH: 21
<212> TYPE: PRT
<213> ORGANISM: Homo sapiens

<400> SEQUENCE: 55

Asp Pro Gly Leu Gly Leu Arg Leu Ile Tyr Tyr Ser Phe Asp Val Lys
 1               5                  10                  15

Asp Ile Asn Lys Gly
```

-continued

20

<210> SEQ ID NO 56
<211> LENGTH: 21
<212> TYPE: PRT
<213> ORGANISM: Homo sapiens

<400> SEQUENCE: 56

Val Met Gly Lys Glu Ile Lys Phe Leu Leu His Phe Val Lys Glu Ser
1               5                   10                  15

Lys Gln Asp Glu Ser
            20

<210> SEQ ID NO 57
<211> LENGTH: 21
<212> TYPE: PRT
<213> ORGANISM: Homo sapiens

<400> SEQUENCE: 57

Asp Pro Gly Gln Gly Leu Arg Leu Ile Tyr Tyr Ser Gln Ile Val Asn
1               5                   10                  15

Asp Phe Gln Lys Gly
            20

<210> SEQ ID NO 58
<211> LENGTH: 21
<212> TYPE: PRT
<213> ORGANISM: Homo sapiens

<400> SEQUENCE: 58

Asp Pro Gly Gln Gly Leu Arg Leu Ile Tyr Tyr Ser His Ile Val Asn
1               5                   10                  15

Asp Phe Gln Lys Gly
            20

<210> SEQ ID NO 59
<211> LENGTH: 21
<212> TYPE: PRT
<213> ORGANISM: Homo sapiens

<400> SEQUENCE: 59

Leu Pro Glu Glu Gly Leu Lys Phe Met Val Tyr Leu Gln Lys Glu Asn
1               5                   10                  15

Ile Ile Asp Glu Ser
            20

<210> SEQ ID NO 60
<211> LENGTH: 21
<212> TYPE: PRT
<213> ORGANISM: Homo sapiens

<400> SEQUENCE: 60

Asn Gln Asn Lys Glu Phe Met Leu Leu Ile Ser Phe Gln Asn Glu Gln
1               5                   10                  15

Val Leu Gln Glu Thr
            20

<210> SEQ ID NO 61
<211> LENGTH: 21
<212> TYPE: PRT
<213> ORGANISM: Homo sapiens

<400> SEQUENCE: 61

```
Asn Gln Asn Lys Glu Phe Met Phe Leu Ile Ser Phe Gln Asn Glu Gln
 1               5                  10                  15

Val Leu Gln Glu Met
            20

<210> SEQ ID NO 62
<211> LENGTH: 21
<212> TYPE: PRT
<213> ORGANISM: Homo sapiens

<400> SEQUENCE: 62

Ala Ala Gly Arg Gly Leu Gln Leu Leu Phe Tyr Ser Val Gly Ile Gly
 1               5                  10                  15

Gln Ile Ser Ser Glu
            20

<210> SEQ ID NO 63
<211> LENGTH: 21
<212> TYPE: PRT
<213> ORGANISM: Homo sapiens

<400> SEQUENCE: 63

Ala Ala Gly Arg Gly Leu Gln Leu Leu Phe Tyr Ser Ile Gly Ile Asp
 1               5                  10                  15

Gln Ile Ser Ser Glu
            20

<210> SEQ ID NO 64
<211> LENGTH: 21
<212> TYPE: PRT
<213> ORGANISM: Homo sapiens

<400> SEQUENCE: 64

Ile Leu Gly Gln Gly Pro Glu Leu Leu Val Gln Phe Gln Asp Glu Ser
 1               5                  10                  15

Val Val Asp Asp Ser
            20

<210> SEQ ID NO 65
<211> LENGTH: 21
<212> TYPE: PRT
<213> ORGANISM: Homo sapiens

<400> SEQUENCE: 65

Asn Leu Gly Gln Gly Pro Glu Leu Leu Ile Arg Tyr Glu Asn Glu Glu
 1               5                  10                  15

Ala Val Asp Asp Ser
            20

<210> SEQ ID NO 66
<211> LENGTH: 21
<212> TYPE: PRT
<213> ORGANISM: Homo sapiens

<400> SEQUENCE: 66

Ile Leu Gly Gln Gly Pro Lys Leu Leu Ile Gln Phe Gln Asn Asn Gly
 1               5                  10                  15

Val Val Asp Asp Ser
            20

<210> SEQ ID NO 67
```

```
<211> LENGTH: 21
<212> TYPE: PRT
<213> ORGANISM: Homo sapiens

<400> SEQUENCE: 67

Ile Leu Gly Gln Lys Val Glu Phe Leu Val Ser Phe Tyr Asn Asn Glu
 1               5                  10                  15

Ile Ser Glu Lys Ser
            20

<210> SEQ ID NO 68
<211> LENGTH: 21
<212> TYPE: PRT
<213> ORGANISM: Homo sapiens

<400> SEQUENCE: 68

Gly Pro Gly Gln Asp Pro Gln Phe Phe Ile Ser Phe Tyr Glu Lys Met
 1               5                  10                  15

Gln Ser Asp Lys Gly
            20

<210> SEQ ID NO 69
<211> LENGTH: 21
<212> TYPE: PRT
<213> ORGANISM: Homo sapiens

<400> SEQUENCE: 69

Gly Pro Gly Gln Asp Pro Gln Phe Leu Ile Ser Phe Tyr Glu Lys Met
 1               5                  10                  15

Gln Ser Asp Lys Gly
            20

<210> SEQ ID NO 70
<211> LENGTH: 21
<212> TYPE: PRT
<213> ORGANISM: Homo sapiens

<400> SEQUENCE: 70

Lys Ser Ser Gln Ala Pro Lys Leu Leu Phe His Tyr Tyr Asn Lys Asp
 1               5                  10                  15

Phe Asn Asn Glu Ala
            20

<210> SEQ ID NO 71
<211> LENGTH: 21
<212> TYPE: PRT
<213> ORGANISM: Homo sapiens

<400> SEQUENCE: 71

Lys Ser Ser Gln Ala Pro Lys Leu Leu Phe His Tyr Tyr Asp Lys Asp
 1               5                  10                  15

Phe Asn Asn Glu Ala
            20

<210> SEQ ID NO 72
<211> LENGTH: 21
<212> TYPE: PRT
<213> ORGANISM: Homo sapiens

<400> SEQUENCE: 72

Val Leu Lys Asn Glu Phe Lys Phe Leu Ile Ser Phe Gln Asn Glu Asn
 1               5                  10                  15
```

```
Val Phe Asp Glu Thr
            20

<210> SEQ ID NO 73
<211> LENGTH: 21
<212> TYPE: PRT
<213> ORGANISM: Homo sapiens

<400> SEQUENCE: 73

Val Leu Lys Asn Glu Phe Lys Phe Leu Val Ser Phe Gln Asn Glu Asn
1               5                   10                  15

Val Phe Asp Glu Thr
            20

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77
<211> LENGTH: 21
<212> TYPE: PRT
<213> ORGANISM: Homo sapiens

<400> SEQUENCE: 77

Tyr Pro Gly Gln His Leu Gln Leu Leu Lys Tyr Phe Ser Gly Asp
1               5                   10                  15

Pro Leu Val Lys Gly
            20

<210> SEQ ID NO 78
<211> LENGTH: 21
<212> TYPE: PRT
<213> ORGANISM: Homo sapiens

<400> SEQUENCE: 78

Tyr Pro Asn Gln Gly Leu Gln Leu Leu Lys Tyr Thr Ser Ala Ala
1               5                   10                  15

Thr Leu Val Lys Gly
            20

<210> SEQ ID NO 79
<211> LENGTH: 21
<212> TYPE: PRT
<213> ORGANISM: Homo sapiens

<400> SEQUENCE: 79

Tyr Pro Asn Gln Gly Leu Gln Leu Leu Lys Tyr Thr Thr Gly Ala
1               5                   10                  15

Thr Leu Val Lys Gly
            20
```

```
<210> SEQ ID NO 80
<211> LENGTH: 21
<212> TYPE: PRT
<213> ORGANISM: Homo sapiens

<400> SEQUENCE: 80

Tyr Pro Asn Gln Gly Leu Gln Leu Leu Leu Lys Tyr Thr Ser Ala Ala
 1               5                  10                  15

Thr Leu Val Lys Gly
            20

<210> SEQ ID NO 81
<211> LENGTH: 21
<212> TYPE: PRT
<213> ORGANISM: Homo sapiens

<400> SEQUENCE: 81

Tyr Pro Asn Gln Gly Leu Gln Leu Leu Leu Lys Tyr Leu Ser Gly Ser
 1               5                  10                  15

Thr Leu Val Glu Ser
            20

<210> SEQ ID NO 82
<211> LENGTH: 21
<212> TYPE: PRT
<213> ORGANISM: Homo sapiens

<400> SEQUENCE: 82

Tyr Pro Asn Gln Gly Leu Gln Leu Leu Leu Lys Tyr Leu Ser Gly Ser
 1               5                  10                  15

Thr Leu Val Lys Gly
            20

<210> SEQ ID NO 83
<211> LENGTH: 21
<212> TYPE: PRT
<213> ORGANISM: Homo sapiens

<400> SEQUENCE: 83

Ser Pro Gly Gln Gly Leu Gln Leu Leu Leu Lys Tyr Phe Ser Gly Asp
 1               5                  10                  15

Thr Leu Val Gln Gly
            20

<210> SEQ ID NO 84
<211> LENGTH: 21
<212> TYPE: PRT
<213> ORGANISM: Homo sapiens

<400> SEQUENCE: 84

His Pro Asn Lys Gly Leu Gln Leu Leu Leu Lys Tyr Thr Ser Ala Ala
 1               5                  10                  15

Thr Leu Val Lys Gly
            20

<210> SEQ ID NO 85
<211> LENGTH: 21
<212> TYPE: PRT
<213> ORGANISM: Homo sapiens

<400> SEQUENCE: 85
```

Tyr Ser Gly Lys Ser Pro Glu Leu Ile Met Phe Ile Tyr Ser Asn Gly
1               5                   10                  15

Asp Lys Glu Asp Gly
            20

<210> SEQ ID NO 86
<211> LENGTH: 21
<212> TYPE: PRT
<213> ORGANISM: Homo sapiens

<400> SEQUENCE: 86

Tyr Ser Gly Lys Ser Pro Glu Leu Ile Met Ser Ile Tyr Ser Asn Gly
1               5                   10                  15

Asp Lys Glu Asp Gly
            20

<210> SEQ ID NO 87
<211> LENGTH: 21
<212> TYPE: PRT
<213> ORGANISM: Homo sapiens

<400> SEQUENCE: 87

Tyr Ser Arg Lys Gly Pro Glu Leu Leu Met Tyr Thr Tyr Ser Ser Gly
1               5                   10                  15

Asn Lys Glu Asp Gly
            20

<210> SEQ ID NO 88
<211> LENGTH: 21
<212> TYPE: PRT
<213> ORGANISM: Homo sapiens

<400> SEQUENCE: 88

Tyr Ser Arg Ile Gly Pro Glu Leu Leu Met Tyr Thr Tyr Ser Ser Gly
1               5                   10                  15

Asn Lys Glu Asp Gly
            20

<210> SEQ ID NO 89
<211> LENGTH: 21
<212> TYPE: PRT
<213> ORGANISM: Homo sapiens

<400> SEQUENCE: 89

Asp Cys Arg Lys Glu Pro Lys Leu Leu Met Ser Val Tyr Ser Ser Gly
1               5                   10                  15

Asn Glu Asp Gly Arg
            20

<210> SEQ ID NO 90
<211> LENGTH: 21
<212> TYPE: PRT
<213> ORGANISM: Homo sapiens

<400> SEQUENCE: 90

Asn Ser Gly Arg Gly Leu Val His Leu Ile Leu Ile Arg Ser Asn Glu
1               5                   10                  15

Arg Glu Lys His Ser
            20

<210> SEQ ID NO 91
<211> LENGTH: 21

```
<212> TYPE: PRT
<213> ORGANISM: Homo sapiens

<400> SEQUENCE: 91

Leu Pro Ser Gln Gly Pro Glu Tyr Val Ile His Gly Leu Thr Ser Asn
 1               5                  10                  15

Val Asn Asn Arg Met
            20

<210> SEQ ID NO 92
<211> LENGTH: 21
<212> TYPE: PRT
<213> ORGANISM: Homo sapiens

<400> SEQUENCE: 92

Ile His Ser Gln Gly Pro Gln Tyr Ile Ile His Gly Leu Lys Asn Asn
 1               5                  10                  15

Glu Thr Asn Glu Met
            20

<210> SEQ ID NO 93
<211> LENGTH: 21
<212> TYPE: PRT
<213> ORGANISM: Homo sapiens

<400> SEQUENCE: 93

Ile His Ser Gln Gly Pro Gln Asn Ile Ile His Gly Leu Lys Asn Asn
 1               5                  10                  15

Glu Thr Asn Glu Met
            20

<210> SEQ ID NO 94
<211> LENGTH: 21
<212> TYPE: PRT
<213> ORGANISM: Homo sapiens

<400> SEQUENCE: 94

Asp Pro Gly Arg Gly Pro Val Phe Leu Leu Leu Ile Arg Glu Asn Glu
 1               5                  10                  15

Lys Glu Lys Arg Lys
            20

<210> SEQ ID NO 95
<211> LENGTH: 21
<212> TYPE: PRT
<213> ORGANISM: Homo sapiens

<400> SEQUENCE: 95

Ser Ser Gly Glu Met Ile Phe Leu Ile Tyr Gln Gly Ser Tyr Asp Gln
 1               5                  10                  15

Gln Asn Ala Thr Glu
            20

<210> SEQ ID NO 96
<211> LENGTH: 21
<212> TYPE: PRT
<213> ORGANISM: Homo sapiens

<400> SEQUENCE: 96

Ser Ser Gly Glu Met Ile Phe Leu Ile Tyr Gln Gly Ser Tyr Asp Glu
 1               5                  10                  15

Gln Asn Ala Thr Glu
```

<210> SEQ ID NO 97
<211> LENGTH: 21
<212> TYPE: PRT
<213> ORGANISM: Homo sapiens

<400> SEQUENCE: 97

His Asp Gly Gly Ala Pro Thr Phe Leu Ser Tyr Asn Ala Leu Asp Gly
 1               5                  10                  15

Leu Glu Glu Thr Gly
            20

<210> SEQ ID NO 98
<211> LENGTH: 21
<212> TYPE: PRT
<213> ORGANISM: Homo sapiens

<400> SEQUENCE: 98

His Asp Gly Gly Ala Pro Thr Phe Leu Ser Tyr Asn Gly Leu Asp Gly
 1               5                  10                  15

Leu Glu Glu Thr Gly
            20

<210> SEQ ID NO 99
<211> LENGTH: 21
<212> TYPE: PRT
<213> ORGANISM: Homo sapiens

<400> SEQUENCE: 99

His Ala Gly Glu Ala Pro Thr Phe Leu Ser Tyr Asn Val Leu Asp Gly
 1               5                  10                  15

Leu Glu Glu Lys Gly
            20

<210> SEQ ID NO 100
<211> LENGTH: 21
<212> TYPE: PRT
<213> ORGANISM: Homo sapiens

<400> SEQUENCE: 100

Glu Leu Gly Lys Arg Pro Gln Leu Ile Ile Asp Ile Arg Ser Asn Val
 1               5                  10                  15

Gly Glu Lys Lys Asp
            20

<210> SEQ ID NO 101
<211> LENGTH: 21
<212> TYPE: PRT
<213> ORGANISM: Homo sapiens

<400> SEQUENCE: 101

Glu Leu Gly Lys Gly Pro Gln Leu Ile Ile Asp Ile Arg Ser Asn Val
 1               5                  10                  15

Gly Glu Lys Lys Asp
            20

<210> SEQ ID NO 102
<211> LENGTH: 21
<212> TYPE: PRT
<213> ORGANISM: Homo sapiens

<400> SEQUENCE: 102

```
Glu Ser Gly Lys Gly Pro Gln Phe Ile Ile Asp Ile Arg Ser Asn Met
1               5                   10                  15

Asp Lys Arg Gln Gly
            20

<210> SEQ ID NO 103
<211> LENGTH: 21
<212> TYPE: PRT
<213> ORGANISM: Homo sapiens

<400> SEQUENCE: 103

Tyr Ser Arg Gln Arg Leu Gln Leu Leu Arg His Ile Ser Arg Glu
1               5                   10                  15

Ser Ile Lys Gly Phe
            20

<210> SEQ ID NO 104
<211> LENGTH: 21
<212> TYPE: PRT
<213> ORGANISM: Homo sapiens

<400> SEQUENCE: 104

Glu Pro Gly Glu Gly Pro Val Leu Leu Val Thr Val Thr Gly Gly
1               5                   10                  15

Glu Val Lys Lys Leu
            20

<210> SEQ ID NO 105
<211> LENGTH: 21
<212> TYPE: PRT
<213> ORGANISM: Homo sapiens

<400> SEQUENCE: 105

Phe Pro Gly Cys Ala Pro Arg Leu Leu Val Lys Gly Ser Lys Pro Ser
1               5                   10                  15

Gln Gln Gly Arg Tyr
            20

<210> SEQ ID NO 106
<211> LENGTH: 21
<212> TYPE: PRT
<213> ORGANISM: Homo sapiens

<400> SEQUENCE: 106

Pro Pro Ser Gly Glu Leu Val Phe Leu Ile Arg Arg Asn Ser Phe Asp
1               5                   10                  15

Glu Gln Asn Glu Ile
            20

<210> SEQ ID NO 107
<211> LENGTH: 21
<212> TYPE: PRT
<213> ORGANISM: Homo sapiens

<400> SEQUENCE: 107

Asn Pro Trp Gly Gln Leu Ile Asn Leu Phe Tyr Ile Pro Ser Gly Thr
1               5                   10                  15

Lys Gln Asn Gly Arg
            20

<210> SEQ ID NO 108
```

```
<211> LENGTH: 21
<212> TYPE: PRT
<213> ORGANISM: Homo sapiens

<400> SEQUENCE: 108

Pro Pro Ser Arg Gln Met Ile Leu Val Ile Arg Gln Glu Ala Tyr Lys
1               5                   10                  15

Gln Gln Asn Ala Thr
            20

<210> SEQ ID NO 109
<211> LENGTH: 21
<212> TYPE: PRT
<213> ORGANISM: Homo sapiens

<400> SEQUENCE: 109

Glu Pro Gly Ala Gly Leu Gln Leu Leu Thr Tyr Ile Phe Ser Asn Met
1               5                   10                  15

Asp Met Lys Gln Asp
            20

<210> SEQ ID NO 110
<211> LENGTH: 21
<212> TYPE: PRT
<213> ORGANISM: Homo sapiens

<400> SEQUENCE: 110

Tyr Pro Asn Arg Gly Leu Gln Phe Leu Leu Lys Tyr Ile Thr Gly Asp
1               5                   10                  15

Asn Leu Val Lys Gly
            20

<210> SEQ ID NO 111
<211> LENGTH: 21
<212> TYPE: PRT
<213> ORGANISM: Homo sapiens

<400> SEQUENCE: 111

Phe Pro Gly Lys Gly Pro Ala Leu Leu Ile Ala Ile Arg Pro Asp Val
1               5                   10                  15

Ser Glu Lys Lys Glu
            20

<210> SEQ ID NO 112
<211> LENGTH: 21
<212> TYPE: PRT
<213> ORGANISM: Homo sapiens

<400> SEQUENCE: 112

Glu Thr Ala Lys Thr Pro Glu Ala Leu Phe Val Met Thr Leu Asn Gly
1               5                   10                  15

Asp Glu Lys Lys Lys
            20

<210> SEQ ID NO 113
<211> LENGTH: 21
<212> TYPE: PRT
<213> ORGANISM: Homo sapiens

<400> SEQUENCE: 113

His Pro Gly Gly Gly Ile Val Ser Leu Phe Met Leu Ser Ser Gly Lys
1               5                   10                  15
```

-continued

Lys Lys His Gly Arg
            20

<210> SEQ ID NO 114
<211> LENGTH: 21
<212> TYPE: PRT
<213> ORGANISM: Homo sapiens

<400> SEQUENCE: 114

Phe Pro Ser Gln Gly Pro Arg Phe Ile Ile Gln Gly Tyr Lys Thr Lys
1               5                   10                  15

Val Thr Asn Glu Val
            20

<210> SEQ ID NO 115
<211> LENGTH: 21
<212> TYPE: PRT
<213> ORGANISM: Homo sapiens

<400> SEQUENCE: 115

Tyr Pro Ala Glu Gly Pro Thr Phe Leu Ile Ser Ile Ser Ser Ile Lys
1               5                   10                  15

Asp Lys Asn Glu Asp
            20

<210> SEQ ID NO 116
<211> LENGTH: 21
<212> TYPE: PRT
<213> ORGANISM: Homo sapiens

<400> SEQUENCE: 116

Tyr Pro Gly Glu Gly Leu Gln Leu Leu Leu Lys Ala Thr Lys Ala Asp
1               5                   10                  15

Asp Lys Gly Ser Asn
            20

<210> SEQ ID NO 117
<211> LENGTH: 21
<212> TYPE: PRT
<213> ORGANISM: Homo sapiens

<400> SEQUENCE: 117

Asp Pro Gly Lys Gly Leu Thr Ser Leu Leu Leu Ile Gln Ser Ser Gln
1               5                   10                  15

Arg Glu Gln Thr Ser
            20

<210> SEQ ID NO 118
<211> LENGTH: 21
<212> TYPE: PRT
<213> ORGANISM: Homo sapiens

<400> SEQUENCE: 118

Asp Thr Gly Arg Gly Pro Val Ser Leu Thr Ile Met Thr Phe Ser Glu
1               5                   10                  15

Asn Thr Lys Ser Asn
            20

<210> SEQ ID NO 119
<211> LENGTH: 21
<212> TYPE: PRT
<213> ORGANISM: Homo sapiens -continued

<400> SEQUENCE: 119

Asp Pro Gly Glu Gly Pro Val Leu Leu Ile Ala Leu Tyr Lys Ala Gly
1               5                   10                  15

Glu Leu Thr Ser Asn
            20

<210> SEQ ID NO 120
<211> LENGTH: 21
<212> TYPE: PRT
<213> ORGANISM: Homo sapiens

<400> SEQUENCE: 120

Lys Tyr Gly Glu Gly Leu Ile Phe Leu Met Met Leu Gln Lys Gly Gly
1               5                   10                  15

Glu Glu Lys Ser His
            20

<210> SEQ ID NO 121
<211> LENGTH: 21
<212> TYPE: PRT
<213> ORGANISM: Homo sapiens

<400> SEQUENCE: 121

Asp Pro Gly Lys Ser Leu Glu Ser Leu Phe Val Leu Leu Ser Asn Gly
1               5                   10                  15

Ala Val Lys Gln Glu
            20

<210> SEQ ID NO 122
<211> LENGTH: 21
<212> TYPE: PRT
<213> ORGANISM: Homo sapiens

<400> SEQUENCE: 122

Gln Glu Lys Lys Ala Pro Thr Phe Leu Phe Met Leu Thr Ser Ser Gly
1               5                   10                  15

Ile Glu Lys Lys Ser
            20

<210> SEQ ID NO 123
<211> LENGTH: 21
<212> TYPE: PRT
<213> ORGANISM: Homo sapiens

<400> SEQUENCE: 123

Lys His Gly Glu Ala Pro Val Phe Leu Met Ile Leu Leu Lys Gly Gly
1               5                   10                  15

Glu Gln Met Arg Arg
            20

<210> SEQ ID NO 124
<211> LENGTH: 21
<212> TYPE: PRT
<213> ORGANISM: Homo sapiens

<400> SEQUENCE: 124

Lys His Gly Glu Ala Pro Val Phe Leu Met Ile Leu Leu Lys Gly Gly
1               5                   10                  15

Glu Gln Lys Gly His
            20

-continued

```
<210> SEQ ID NO 125
<211> LENGTH: 21
<212> TYPE: PRT
<213> ORGANISM: Homo sapiens

<400> SEQUENCE: 125

Asp Pro Gly Lys Gly Pro Glu Phe Leu Phe Thr Leu Tyr Ser Ala Gly
1               5                   10                  15

Glu Glu Lys Glu Lys
            20

<210> SEQ ID NO 126
<211> LENGTH: 21
<212> TYPE: PRT
<213> ORGANISM: Homo sapiens

<400> SEQUENCE: 126

Tyr Pro Ser Lys Pro Leu Gln Leu Leu Gln Arg Glu Thr Met Glu Asn
1               5                   10                  15

Ser Lys Asn Phe Gly
            20

<210> SEQ ID NO 127
<211> LENGTH: 21
<212> TYPE: PRT
<213> ORGANISM: Homo sapiens

<400> SEQUENCE: 127

Arg Pro Gly Gly His Pro Val Phe Leu Ile Gln Leu Val Lys Ser Gly
1               5                   10                  15

Glu Val Lys Lys Gln
            20
```